(12) United States Patent
Ohsuye et al.

(10) Patent No.: US 6,602,681 B1
(45) Date of Patent: Aug. 5, 2003

(54) ENZYMATIC PRODUCTION OF A C-TERMINAL α-AMIDATED PEPTIDE OR PROTEIN

(75) Inventors: Kazuhiro Ohsuye, Ibaraki (JP); Katsuhiko Kitano, Ikeda (JP); Shoji Tanaka, Ashiya (JP); Hisayuki Matsuo, 6653 Ooaza Kihara, Kiyotake-cho, Miyazaki-gun, Miyazaki (JP); Kensaku Mizuno, Miyazaki (JP)

(73) Assignees: Hisayuki Matsuo, Miyazaki (JP); Daiichi Suntory Pharma Co., Ltd., Tokyo (JP)

( * ) Notice: Subject to any disclaimer, the term of this patent is extended or adjusted under 35 U.S.C. 154(b) by 0 days.

(21) Appl. No.: 08/845,381

(22) Filed: Apr. 25, 1997

Related U.S. Application Data

(62) Division of application No. 07/509,583, filed on Apr. 16, 1990, now Pat. No. 6,245,887, which is a division of application No. 07/219,375, filed on Jul. 15, 1988, now Pat. No. 6,262,232.

(30) Foreign Application Priority Data

Jul. 17, 1987 (JP) ............................. 62-177184
Dec. 5, 1987 (JP) ............................. 62-306867

(51) Int. Cl.[7] ................................................. C12P 12/06
(52) U.S. Cl. ....................................................... 435/68.1
(58) Field of Search ............................... 435/129, 68.1, 435/189

(56) References Cited

U.S. PATENT DOCUMENTS 4,708,934 A  11/1987  Gilligan et al. ............ 435/68.1
4,921,797 A  * 5/1990  Matsuo et al. ............... 435/129

OTHER PUBLICATIONS

A.F. Bradbury et al., *Nature*, 298: 686–88 (1982).
A.F. Bradbury et al., *Eur. J. Biochem.*, 169: 579–84 (1987).
B.A. Eipper et al., *Pro. Natl. Acad. Sci.*, 80: 5144–48 (1983).
C. Mollay et al., *FEBS*, 202: 251–54 (1986).
M.M. Bendig, *J.B.C.*, 261: 11935–37 (1986).
K. Mizuno et al., *B.B.R.C.*, 137: 984–91 (1986).
K. Mizuno et al., *B.B.R.C.*, 148: 546–52 (1987).
K. Ohsuye et al., *B.B.R.C.*, 150: 1275–81 (1988).
J. Sakata et al., *B.B.R.C.*, 140: 230–36 (1986).
B.A. Eipper et al., *Mol. Endo.*, 1: 777–90 (1987).
V. May et al., *J.B.C.*, 263: 7550–54 (1988).
B.A. Eipper, *J.B.C.*, 263: 8371–79 (1988).
A.G. Katapodis et al., *B.B.R.C.*, 151: 499–05 (1988).
J.S. Kizer et al., *Proc. Natl. Acad. Sci.*, 81: 3228–32 (1984).
H. Vaeroy et al., *B.B.R.C.*, 148: 24–30 (1987).
N.H. Mehta et al., *A.B.B.*, 261: 44–54 (1988).
J.S. Gale, *Biochem J.*, 251: 251–59 (1988).
L. Ouafik et al., *Proc. Natl. Acad. Sci.*, 84: 261–64 (1987).

* cited by examiner

*Primary Examiner*—Rebecca E. Prouty
*Assistant Examiner*—David Steadman
(74) *Attorney, Agent, or Firm*—Burns, Doane, Swecker & Mathis, L.L.P.

(57) ABSTRACT

A C-terminal α-amidating enzyme of *Xenopus laevis* and precursor thereof produced by a recombinant DNA technique; a DNA coding for the enzyme or precursor thereof; a plasmid containing the DNA; a host organism transformed with the plasmid; a process for production of the enzyme using the transformant; and a process for production of a C-terminal α-amidated peptide using the enzyme.

1 Claim, 48 Drawing Sheets

```
                ACCATTCAGTTGTGGGTGATCAGCAGTGTGC  -235

CAGCATCTAAAGGAACCAAATCATTGCAACTTGTACCCT  -196

GATCAGGCACCTTATACTGGACGCAAGTGCACTTCTTCC  -157

CTCAAGAAGATCATATCCCGGGAAGAATGTGTATTTCTG  -118

GTTACCTGCGGGGCTAGCACTGATGGAGTAGGGGGGATT   -79

TATCTGGTTTCCTAATTACCAGGATTACAACTTGCCTTT   -40

AATTTACTCCTGCAGTAAGGCACAGACCACAGGGTGGAC    -1
```

```
ATG GCC AGC CTC AGT AGC AGC TTT CTT GTG    30
Met Ala Ser Leu Ser Ser Ser Phe Leu Val
-37                                      -28
CTC TTT CTC TTA TTT CAG AAC AGC TGC TAC    60
Leu Phe Leu Leu Phe Gln Asn Ser Cys Tyr
                                         -18
TGT TTC AGG AGT CCC CTC TCT GTC TTT AAG    90
Cys Phe Arg Ser Pro Leu Ser Val Phe Lys
                                          -8
AGG TAT GAG GAA TCT ACC AGA TCA CTT TCC   120
Arg Tyr Glu Glu Ser Thr Arg Ser Leu Ser
                         -1   1       3
AAT GAC TGC TTG GGA ACC ACG CGG CCC GTT   150
Asn Asp Cys Leu Gly Thr Thr Arg Pro Val
                                          13
ATG TCT CCA GGC TCA TCA GAT TAT ACT CTA   180
Met Ser Pro Gly Ser Ser Asp Tyr Thr Leu
                                          23
GAT ATC CGC ATG CCA GGA GTA ACT CCG ACA   210
Asp Ile Arg Met Pro Gly Val Thr Pro Thr
                                          33
GAG TCG GAC ACA TAT TTG TGC AAG TCT TAC   240
Glu Ser Asp Thr Tyr Leu Cys Lys Ser Tyr
                                          43
CGG CTG CCA GTG GAT GAT GAA GCC TAT GTA   270
Arg Leu Pro Val Asp Asp Glu Ala Tyr Val
                                          53
```

FIG.1A

```
GTT GAC TTC AGA CCA CAT GCC AAT ATG GAT    300
Val Asp Phe Arg Pro His Ala Asn Met Asp
                                        63
ACT GCA CAT CAC ATG CTT CTA TTT GGA TGC    330
Thr Ala His His Met Leu Leu Phe GLY Cys
                                        73
AAT ATA CCT TCT TCC ACT GAT GAT TAC TGG    360
Asn Ile Pro Ser Ser Thr Asp Asp Tyr Trp
                                        83
GAC TGT AGT GCG GGA ACT TGC ATG GAC AAA    390
Asp Cys Ser Ala Gly Thr Cys Met Asp Lys
                                        93
TCC AGT ATA ATG TAT GCC TGG GCA AAG AAT    420
Ser Ser Ile Met Tyr Ala Trp Ala Lys Asn
                                       103
GCA CCA CCC ACC AAA CTT CCA GAA GGA GTT    450
Ala Pro Pro Thr Lys Leu Pro Glu Gly Val
                                       113
GGC TTT CGT GTT GGA GGG AAA TCA GGC AGT    480
Gly Phe Arg Val Gly Gly Lys Ser Gly Ser
                                       123
AGA TAT TTT GTG CTT CAA GTT CAC TAT GGA    510
Arg Tyr Phe Val Leu Gln Val His Tyr Gly
                                       133
AAT GTG AAA GCA TTC CAG GAT AAA CAT AAA    540
Asn Val Lys Ala Phe Gln Asp Lys His Lys
                                       143
GAT TGC ACG GGG GTG ACA GTA CGA GTA ACA    570
Asp Cys Thr Gly Val Thr Val Arg Val Thr
                                       153
CCT GAA AAA CAA CCG CPA ATT GCA GGC ATT    600
Pro Glu Lys Gln Pro Gln Ile Ala Gly Ile
                                       163
TAT CTT TCA ATG TCT GTG GAC ACT GTT ATT    630
Tyr Leu Ser Met Ser Val Asp Thr Val Ile
                                       173
CCA CCT GGG GAA GAG GCA GTT AAT TCT GAT    660
Pro Pro Gly Glu Glu Ala Val Asn Ser Asp
                                       183
ATC GCC TGC CTC TAC AAC AGG CCG ACA ATA    690
Ile Ala Cys Leu Tvr Asn Arg Pro Thr Ile
                                       193
```

FIG.1B

```
CAC CCA TTT GCC TAC AGA GTC CAC ACT CAT    720
His Pro Phe Ala Tyr Arg Val His Thr His
                                    203
CAG TTG GGG CAG GTC GTA AGT GGA TTT AGA    750
Gln Leu Gly Gln Val Val Ser Gly Phe Arg
                                    213
GTG AGA CAT GGC AAG TGG TCT TTA ATT GGT    780
Val Arg His Gly Lys Trp Ser Leu Ile Gly
                                    223
AGA CAA AGC CCA CAG CTG CCA CAG GCA TTT    810
Arg Gln Ser Pro Gln Leu Pro Gln Ala Phe
                                    233
TAC CCT GTA GAG CAT CCA GTA GAG ATT AGC    840
Tyr Pro Val Glu His Pro Val Glu Ile Ser
                                    243
CCT GGG GAT ATT ATA GCA ACC AGG TGT CTG    870
Pro Gly Asp Ile Ile Ala Thr Arg Cys Leu
                                    253
TTC ACT GGT AAA GGC AGG ACG TCA GCA ACA    900
Phe Thr Gly Lys Gly Arg Thr Ser Ala Thr
                                    263
TAT ATT GGT GGC ACA TCT AAC GAT GAA ATG    930
Tyr Ile Gly Gly Thr Ser Asn Asp Glu Met
                                    273
TGT AAT TTA TAC ATC ATG TAT TAC ATG GAT    960
Cys Asn Leu Tyr Ile Met Tyr Tyr Met Asp
                                    283
GCG GCC CAT GCT ACG TCA TAC ATG ACC TGT    990
Ala Ala His Ala Thr Ser Tyr Met Thr Cys
                                    293
GTA CAG ACG GGT GAA CCA AAG TTA TTT CAA   1020
Val Gln Thr Gly Glu Pro Lys Leu Phe Gln
                                    303
AAC ATC CCT GAG ATT GCA AAT GTT CCC ATT   1050
Asn Ile Pro Glu Ile Ala Asn Val Pro Ile
                                    313
CCT GTA AGC CCT GAC ATG ATG ATG ATG ATG   1080
Pro Val Ser Pro Asp Met Met Met Met Met
                                    323
GGA CAT GGT CAC CAC CAT ACA GAA GCT GAG   1110
Gly His Gly His His His Thr Glu Ala Glu
                                    333
```

FIG.1C

```
CCT GAG AAG AAT ACA GGA CTT CAG CAG CCT  1140
Pro Glu Lys Asn Thr Gly Leu Gln Gln Pro
                                    343
AAA CGG GAG GAG GAA GAA GTA TTA GAT CAG  1170
Lys Arg Glu Glu Glu Glu Val Leu Asp Gln
                                    353
GGT CTC ATT ACC TTA GGG GAT AGC GCA GTG  1200
Gly Leu Ile Thr Leu Gly Asp Ser Ala Val
                                    363
TGA TGGAGGAGGACATGATCCCTATACCGTTGAAGGGG  1238
***
ATGACCCAATCATTTTAAAGAACGTTCTTTTAAACATGA  1277

GAGACCACATCCAGGAGACATAAATCCACAAATTGTATA  1316

AGTTGTGTGTATACATCACCCTTTTATGACAAAGATCCA  1355

TAATATAATACGTTATCACTGACCCTTCTGCAACATCCT  1394

TAATCCAGGATTTGCTCACTCTCCATTGCTGTCATACAG  1433

ATGTTCACTTATGGGCAACAAAATACTTTTCTCCTAATT  1472

CAGGTCCAGTTTTTCTCATTGAAGTGCATCTGGCTCAAT  1511

TGACAAATCTAAAATTGATTTAGGAAATCAGCTTTTTCC  1550

CCATCAAATTGAAGCTGGCCCAAAAGTTACTCTTAAAAG  1589

AAGGTGACAGTCAAGTCTCAACTTTTGCCCACTGAGTTA  1628

GTGATACCAATTCTGTGTAGGGGAATTAAGTAGCTTTTC  1667

TTAAAGGGTTGGTTCACCTTTAAGTCAACTTTTAGTATG  1706
```

FIG.1D

```
TTATAGAATGACTAATTCATAAATAAATAAATAAAAGCA   1745

GCTTTTCAATTGGTCTTCATTATTTATTTTGTATAGTTT   1784

TTTTATTATTTGTCTTTTTCATCTGACTTTTCCAGCTT    1823

TCAAATGGGGGTCACTGACCCCATCTAAAAAAACAAATG   1862

CTCTGTAAGACTACAAATTTATTGTTACTGCTTTTAATT   1901

AGTAATGTTTCTATTCAGGCCCTCCCCTATTCATATTCA   1940

AGCCTTTTATTCCAATCAGTGCATGGTTGCTAGGGTAAT   1979

TGGTACCCTAGCAACCAGATCACTAAAACTGCAAACTGG   2018

AGAACTGCTGAATAAAAAGCTAAATAACAAAAAAAACAC   2057

AAATAATAAAAAATGTAAACCAACTGCAAATTGTCAGAA   2096

TATCACCCTGTACAATCTACATCACACTAAAAGTTAATT   2135

TAAAGGTGAACAACCCCATAAGGAAGACATACAATTTGT   2174

GGATACACACTACAGACACTACAACCTAGATGGCTCA     2213

TTAAGGAATATGATTTACATTTTATTTATTAAAAATGAA   2252

ATGATTTAACTGTTGATTTTGAATTGATTATGTTGATTC   2291

TAATGTTGAATTGTTATTGGGTGCTGAAAACTGATCATA   2330

GGGTGGAATGTATAC                           2345
```

FIG. 1E

```
TCA CTT TCC AAT GAC TGC TTG GGA ACC ACG  30
Ser Leu Ser Asn Asp Cys Leu Gly Thr Thr
                                     10
CGG CCC GTT ATG TCT CCA GGC TCA TCA GAT  60
Arg Pro Val Met Ser Pro Gly Ser Ser Asp
                                     20
TAT ACT CTA GAT ATC CGC ATG CCA GGA GTA  90
Tyr Thr Leu Asp Ile Arg Met Pro Gly Val
                                     30
ACT CCG ACA GAG TCG GAC ACA TAT TTG TGC 120
Thr Pro Thr Glu Ser Asp Thr Tyr Leu Cys
                                     40
AAG TCT TAC CGG CTG CCA GTG GAT GAT GAA 150
Lys Ser Tyr Arg Leu Pro Val Asp Asp Glu
                                     50
GCC TAT GTA GTT GAC TTC AGA CCA CAT GCC 180
Ala Tyr Val Val Asp Phe Arg Pro His Ala
                                     60
AAT ATG GAT ACT GCA CAT CAC ATG CTT CTA 210
Asn Met Asp Thr Ala His His Met Leu Leu
                                     70
TTT GGA TGC AAT ATA CCT TCT TCC ACT GAT 240
Phe Gly Cys Asn Ile Pro Ser Ser Thr Asp
                                     80
GAT TAC TGG GAC TGT AGT GCG GGA ACT TGC 270
Asp Tyr Trp Asp Cys Ser Ala Gly Thr Cys
                                     90
ATG GAC AAA TCC AGT ATA ATG TAT GCC TGG 300
Met Asp Lys Ser Ser Ile Met Tyr Ala Trp
                                    100
GCA AAG AAT GCA CCA CCC ACC AAA CTT CCA 330
Ala Lys Asn Ala Pro Pro Thr Lys Leu Pro
                                    110
GAA GGA GTT GGC TTT CGT GTT GGA GGG AAA 360
Glu Gly Val Gly Phe Arg Val Gly Gly Lys
                                    120
TCA GGC AGT AGA TAT TTT GTG CTT CAA GTT 390
Ser Gly Ser Arg Tyr Phe Val Leu Gln Val
                                    130
CAC TAT GGA AAT GTG AAA GCA TTC CAG GAT 420
His Tyr Gly Asn Val Lys Ala Phe Gln Asp
                                    140
```

FIG.2A

```
AAA CAT AAA GAT TGC ACG GGG GTG ACA GTA 450
Lys His Lys Asp Cys Thr Gly Val Thr Val
                                    150
CGA GTA ACA CCT GAA AAA CAA CCG CAA ATT 480
Arg Val Thr Pro Glu Lys Gln Pro Gln Ile
                                    160
GCA GGC ATT TAT CTT TCA ATG TCT GTG GAC 510
Ala Gly Ile Tyr Leu Ser Met Ser Val Asp
                                    170
ACT GTT ATT CCA CCT GGG GAA GAG GCA GTT 540
Thr Val Ile Pro Pro Gly Glu Glu Ala Val
                                    180
AAT TCT GAT ATC GCC TGC CTC TAC AAC AGG 570
Asn Ser Asp Ile Ala Cys Leu Tyr Asn Arg
                                    190
CCG ACA ATA CAC CCA TTT GCC TAC AGA GTC 600
Pro Thr Ile His Pro Phe Ala Tyr Arg Val
                                    200
CAC ACT CAT CAG TTG GGG CAG GTC GTA AGT 630
His Thr His Gln Leu Gly Gln Val Val Ser
                                    210
GGA TTT AGA GTG AGA CAT GGC AAG TGG TCT 660
Gly Phe Arg Val Arg His Gly Lys Trp Ser
                                    220
TTA ATT GGT AGA CAA AGC CCA CAG CTG CCA 690
Leu Ile Gly Arg Gln Ser Pro Gln Leu Pro
                                    230
CAG GCA TTT TAC CCT GTA GAG CAT CCA GTA 720
Gln Ala Phe Tyr Pro Val Glu His Pro Val
                                    240
GAG ATT AGC CCT GGG GAT ATT ATA GCA ACC 750
Glu Ile Ser Pro Gly Asp Ile Ile Ala Thr
                                    250
AGG TGT CTG TTC ACT GGT AAA GGC AGG ACG 780
Arg Cys Leu Phe Thr Gly Lys Gly Arg Thr
                                    260
TCA GCA ACA TAT ATT GGT GGC ACA TCT AAC 810
Ser Ala Thr Tyr Ile Gly Gly Thr Ser Asn
                                    270
GAT GAA ATG TGT AAT TTA TAC ATC ATG TAT 840
Asp Glu Met Cys Asn Leu Tyr Ile Met Tyr
                                    280
```

FIG.2B

```
TAC ATG GAT GCG GCC CAT GCT ACG TCA TAC   870
Tyr Met Asp Ala Ala His Ala Thr Ser Tyr
                                    290
ATG ACC TGT GTA CAG ACG GGT GAA CCA AAG   900
Met Thr Cys Val Gln Thr Gly Glu Pro Lys
                                    300
TTA TTT CAA AAC ATC CCT GAG ATT GCA AAT   930
Leu Phe Gln Asn Ile Pro Glu Ile Ala Asn
                                    310
GTT CCC ATT CCT GTA AGC CCT GAC ATG ATG   960
Val Pro Ile Pro Val Ser Pro Asp Met Met
                                    320
ATG ATG ATG GGA CAT GGT CAC CAC CAT ACA   990
Met Met Met Gly His Gly His His His Thr
                                    330
GAA GCT GAG CCT GAG AAG AAT ACA GGA CTT  1020
Glu Ala Glu Pro Glu Lys Asn Thr Gly Leu
                                    340
CAG CAG CCT AAA                          1032
Gln Gln Pro Lys
            344
```

FIG.2C

```
TCA CTT TCC AAT GAC TGC TTG GGA ACC ACG  30
Ser Leu Ser Asn Asp Cys Leu Gly Thr Thr
                                      10
CGG CCC GTT ATG TCT CCA GGC TCA TCA GAT  60
Arg Pro Val Met Ser Pro Gly Ser Ser Asp
                                      20
TAT ACT CTA GAT ATC CGC ATG CCA GGA GTA  90
Tyr Thr Leu Asp Ile Arg Met Pro Gly Val
                                      30
ACT CCG ACA GAG TCG GAC ACA TAT TTG TGC 120
Thr Pro Thr Glu Ser Asp Thr Tyr Leu Cys
                                      40
AAG TCT TAC CGG CTG CCA GTG GAT GAT GAA 150
Lys Ser Tyr Arg Leu Pro Val Asp Asp Glu
                                      50
GCC TAT GTA GTT GAC TTC AGA CCA CAT GCC 180
Ala Tyr Val Val Asp Phe Arg Pro His Ala
                                      60
AAT ATG GAT ACT GCA CAT CAC ATG CTT CTA 210
Asn Met Asp Thr Ala His His Met Leu Leu
                                      70
TTT GGA TGC AAT AlA CCT TCT TCC ACT GAT 240
Phe Gly Cys Asn Ile Pro Ser Ser Thr Asp
                                      80
GAT TAC TGG GAC TCT AGT GCG GGA ACT TGC 270
Asp Tyr Trp Asp Ser Ser Ala Gly Thr Cys
                                      90
ATG GAC AAA TCC AGT ATA ATG TAT GCC TGG 300
Met Asp Lys Ser Ser Ile Met Tyr Ala Trp
                                     100
GCA AAG AAT GCA CLA CCC ACC AAA CTT CCA 330
Ala Lys Asn Ala Pro Pro Thr Lys Leu Pro
                                     110
GAA GGA GTT GGC TPT CGT GTT GGA GGG AAA 360
Glu Gly Val Gly Phe Arg Val Gly Gly Lys
                                     120
TCA GGC AGT AGA TAT TTT GTG CTT CAA GTT 390
Ser Gly Ser Arg Tyr Phe Val Leu Gln Val
                                     130
CAC TAT GGA AAT GTG AAA GCA TTC CAG GAT 420
His Tyr Gly Asn Val Lys Ala Phe Gln Asp
                                     140
AAA CAT AAA GAT TGC ACG GGG GTG ACA GTA 450
Lys His Lys Asp Cys Thr Gly Val Thr Val
                                     150
CGA GTA ACA CCT GAA AAA CAA CCG CAA ATT 480
Arg Val Thr Pro Glu Lys Gln Pro Gln Ile
                                     160
GCA GGC ATT TAT CTT TCA ATG TCT GTG GAC 510
Ala Gly Ile Tyr Leu Ser Met Ser Val Asp
                                     170
```

FIG.3A

```
ACT GTT ATT CCA CCT GGG GAA GAG GCA GTT  540
Thr Val Ile Pro Pro Gly Glu Glu Ala Val
                                    180
AAT TCT GAT ATC GCC TGC CTC TAC AAC AGG  570
Asn Ser Asp Ile Ala Cys Leu Tyr Asn Arg
                                    190
CCG ACA ATA CAC CCA TTT GCC TAC AGA GTC  600
Pro Thr Ile His Pro Phe Ala Tyr Arg Val
                                    200
CAC ACT CAT CAG TTG GGG CAG GTC GTA AGT  630
His Thr His Gln Leu Gly Gln Val Val Ser
                                    210
GGA TTT AGA GTG AGA CAT GGC AAG TGG TCT  660
Gly Phe Arg Val Arg His Gly Lys Trp Ser
                                    220
TTA ATT GGT AGA CAA AGC CCA CAG CTG CCA  690
Leu Ile Gly Arg Gln Ser Pro Gln Leu Pro
                                    230
CAG GCA TTT TAC CCT GTA GAG CAT CCA GTA  720
Gln Ala Phe Tyr Pro Val Glu His Pro Val
                                    240
GAG ATT AGC CCT GGG GAT ATT ATA GCA ACC  750
Glu Ile Ser Pro Gly Asp Ile Ile Ala Thr
                                    250
AGG TGT CTG TTC ACT GGT AAA GGC AGG ACG  780
Arg Cys Leu Phe Thr Gly Lys Gly Arg Thr
                                    260
TCA GCA ACA TAT ATT GGT GGC ACA TCT AAC  810
Ser Ala Thr Tyr Ile Gly Gly Thr Ser Asn
                                    270
GAT GAA ATG TGT AAT TTA TAC ATC ATG TAT  840
Asp Glu Met Cys Asn Leu Tyr Ile Met Tyr
                                    280
TAC ATG GAT GCG GCC CAT GCT ACG TCA TAC  870
Tyr Met Asp Ala Ala His Ala Thr Ser Tyr
                                    290
ATG ACC TGT GTA CAG ACG GGT GAA CCA AAG  900
Met Thr Cys Val Gln Thr Gly Glu Pro Lys
                                    300
TTA TTT CAA AAC ATC CCT GAG ATT GCA AAT  930
Leu Phe Gln Asn Ile Pro Glu Ile Ala Asn
                                    310
GTT CCC ATT CCT GTA AGC CCT GAC ATG ATG  960
Val Pro Ile Pro Val Ser Pro Asp Met Met
                                    320
ATG ATG ATG GGA CAT GGT CAC CAC CAT ACA  990
Met Met Met Gly His Gly His His His Thr
                                    330
```

FIG.3B

```
GAA GCT GAC CCT GAG AAG AAT ACA GGA CTT 1022
Glu Ala Glu Pro Glu Lys Asn Thr Gly Leu
                                     340
CAG CAG CCT AAA CGG GAG GAG GAA GAA GTA 1050
Gln Gln Pro Lys Arg Glu Glu Glu Glu Val
                                     350
TTA GAT CAG GGT CTC ATT ACC TTA GGG GAT 1080
Leu Asp Gln Gly Leu Ile Thr Leu Gly Asp
                                     360
AGC GCA GTG 1089
Ser Ala Val
        363
```

FIG.3C

| | |
|---|---|
| ATG GCC AGC CTC AGT AGC AGC TTT CTT GTG<br>Met Ala Ser Leu Ser Ser Ser Phe Leu Val<br>10 | 30 |
| CTC TTT CTC TTA TTT CAG AAC AGC TGC TAC<br>Leu Phe Leu Leu Phe Gln Asn Ser Cys Tyr<br>20 | 60 |
| TGT TTC AGG AGT CCC CTC TCT GTC TTT AAG<br>Cys Phe Arg Ser Pro Leu Ser Val Phe Lys<br>30 | 90 |
| AGG TAT GAG GAA TCT ACC AGA TCA CTT TCC<br>Arg Tyr Glu Glu Ser Thr Arg Ser Leu Ser<br>40 | 120 |
| AAT GAC TGC TTG GGA ACC ACG CGG CCC GTT<br>Asn Asp Cys Leu Gly Thr Thr Arg Pro Val<br>50 | 150 |
| ATG TCT CCA GGC TCA TCA GAT TAT ACT CTA<br>Met Ser Pro Gly Ser Ser Asp Tyr Thr Leu<br>60 | 180 |
| GAT ATC CGC ATG CCA GGA GTA ACT CCG ACA<br>Asp Ile Arg Met Pro Gly Val Thr Pro Thr<br>70 | 210 |
| GAG TCG GAC ACA TAT TTG TGC AAG TCT TAC<br>Glu Ser Asp Thr Tyr Leu Cys Lys Ser Tyr<br>80 | 240 |
| CGG CTG CCA GTG GAT GAT GAA GCC TAT GTA<br>Arg Leu Pro Val Asp Asp Glu Ala Tyr Val<br>90 | 270 |
| GTT GAC TTC AGA CCA CAT GCC AAT ATG GAT<br>Val Asp Phe Arg Pro His Ala Asn Met Asp<br>100 | 300 |
| ACT GCA CAT CAC ATG CTT CTA TTT GGA TGC<br>Thr Ala His His Met Leu Leu Phe Gly Cys<br>110 | 330 |
| AAT ATA CCT TCT TCC ACT GAT GAT TAC TGG<br>Asn Ile Pro Ser Ser Thr Asp Asp Tyr Trp<br>120 | 360 |
| GAC TGT AGT GCG GGA ACT TGC ATG GAC AAA<br>Asp Cys Ser Ala Gly Thr Cys Met Asp Lys<br>130 | 390 |
| TCC AGT ATA ATG TAT GCC TGG GCA AAG AAT<br>Ser Ser Ile Met Tyr Ala Trp Ala Lys Asn<br>140 | 420 |

FIG.4A

```
GCA CCA CCC ACC AAA CTT CCA GAA GGA GTT    450
Ala Pro Pro Thr Lys Leu Pro Glu Gly Val
                                    150
GGC TTT CGT GTT GGA GGG AAA TCA GGC AGT    480
Gly Phe Arg Val Gly Gly Lys Ser Gly Ser
                                    160
AGA TAT TTT GTG CTT CAA GTT CAC TAT GGA    510
Arg Tyr Phe Val Leu Gln Val His Tyr Gly
                                    170
AAT GTG AAA GCA TTC CAG GAT AAA CAT AAA    540
Asn Val Lys Ala Phe Gln Asp Lys His Lys
                                    180
GAT TGC ACG GGG GTG ACA GTA CGA GTA ACA    570
Asp Cys Thr Gly Val Thr Val Arg Val Thr
                                    190
CCT GAA AAA CAA CCG CPA ATT GCA GGC ATT    600
Pro Glu Lys Gln Pro Gln Ile Ala Gly Ile
                                    200
TAT CTT TCA ATG TCT GTG GAC ACT GTT ATT    630
Tyr Leu Ser Met Ser Val Asp Thr Val Ile
                                    210
CCA CCT GGG GAA GAG GCA GTT AAT TCT GAT    660
Pro Pro Gly Glu Glu Ala Val Asn Ser Asp
                                    220
ATC GCC TGC CTC TAC AAC AGG CCG ACA ATA    690
Ile Ala Cys Leu Tvr Asn Arg Pro Thr Ile
                                    230
CAC CCA TTT GCC TAC AGA GTC CAC ACT CAT    720
His Pro Phe Ala Tyr Arg Val His Thr His
                                    240
CAG TTG GGG CAG GTC GTA AGT GGA TTT AGA    750
Gln Leu Gly Gln Val Val Ser Gly Phe Arg
                                    250
GTG AGA CAT GGC AAG TGG TCT TTA ATT GGT    780
Val Arg His Gly Lys Trp Ser Leu Ile Gly
                                    260
AGA CAA AGC CCA CAG CTG CCA CAG GCA TTT    810
Arg Gln Ser Pro Gln Leu Pro Gln Ala Phe
                                    270
TAC CCT GTA GAG CAT CCA GTA GAG ATT AGC    840
Tyr Pro Val Glu His Pro Val Glu Ile Ser
                                    280
```

FIG.4B

```
CCT GGG GAT ATT ATA GCA ACC AGG TGT CTG   870
Pro Gly Asp Ile Ile Ala Thr Arg Cys Leu
                                    290
TTC ACT GGT AAA GGC AGG ACG TCA GCA ACA   900
Phe Thr Gly Lys Gly Arg Thr Ser Ala Thr
                                    300
TAT ATT GGT GGC ACA TCT AAC GAT GAA ATG   930
Tyr Ile Gly Gly Thr Ser Asn Asp Glu Met
                                    310
TGT AAT TTA TAC ATC ATG TAT TAC ATG GAT   960
Cys Asn Leu Tyr Ile Met Tyr Tyr Met Asp
                                    320
GCG GCC CAT GCT ACG TCA TAC ATG ACC TGT   990
Ala Ala His Ala Thr Ser Tyr Met Thr Cys
                                    330
GTA CAG ACG GGT GAA CCA AAG TTA TTT CAA  1020
Val Gln Thr Gly Glu Pro Lys Leu Phe Gln
                                    340
AAC ATC CCT GAG ATT GCA AAT GTT CCC ATT  1050
Asn Ile Pro Glu Ile Ala Asn Val Pro Ile
                                    350
CCT GTA AGC CCT GAC ATG ATG ATG ATG ATG  1080
Pro Val Ser Pro Asp Met Met Met Met Met
                                    360
GGA CAT GGT CAC CAC CAT ACA GAA GCT GAG  1110
Gly His Gly His His His Thr Glu Ala Glu
                                    370
CCT GAG AAG AAT ACA GGA CTT CAG CAG CCT  1140
Pro Glu Lys Asn Thr Gly Leu Gln Gln Pro
                                    380
AAA CGG GAG GAG GAA GAA GTA TTA GAT CAG  1170
Lys Arg Glu Glu Glu Glu Val Leu Asp Gln
                                    390
GGT CTC ATT ACC TTA GGG GAT AGC GCA GTG  1200
Gly Leu Ile Thr Leu Gly Asp Ser Ala Val
                                    400
```

FIG.4C

```
CCT GAG AAG AAT ACA GGA CTT CAG CAG CCT   1140
Pro Glu Lys Asn Thr Gly Leu Gln Gln Pro
                                    380
AAA CGG GAG GAG GAA GAA GTA TTA GAT CAG   1170
Lys Arg Glu Glu Glu Glu Val Leu Asp Gln
                                    390
GGT CTC ATT ACC TTA GGG GAT AGC GCA GTG   1200
Gly Leu Ile Thr Leu Gly Asp Ser Ala Val
                                    400
```

FIG.4D

T-4 Val-Thr-Pro-Glu-Lys

T-6 Ala-Plie-Gln-Asp-Lys

T-8 Met-Gly-His-Gly-His-His-His-Thr-Glu-Ala-Glu-Pro-Glu-Lys

T-11 Met-Met-Gly-His-Gly-His-His-His-Thr-Glu-Ala-Glu-Pro-Glu-Lys

T-9 Asn-Thr-Gly-Leu-Gln-Gln-Pro-Lys

T-10 Trp-Ala-Lys

T-18 Leu-Pro-Glu-Gly-Val-Gly-Phe-Arg

T-22 Val-His-Thr-His-Gln-Leu-Gly-Gln-Val-Val-Ser-Gly-Phe-Arg

T-23 Pro-Val-Met-Ser-Pro-Gly-Ser-Ser-Asp-Tyr-Thr-Leu-Asp-Ile-Arg

T-24 Trp-Ser-Leu-Ile-Gly-Arg

T-30 Leu-Pro-Val-Asp-Asp-Glu-Ala-Tyr-Val-Val-Asp-Phe-Arg-Pro -----

T-35 Ala-Phe-Tyr-Pro-Val-Glu-His-Pro-Val-Glu-Ile-Ser-Pro-
    Gly-Asp-Ile-Ile-Ala-Thr-Arg

T-39 Gln-Ser-Pro-Gln-Leu-Pro-Gln-Ala-Phe-Tyr-Pro-Val-Glu-
    His-Pro-Val-Glu-Ile-Ser-Pro-Gly-X-Ile -----

T-45 Met-Pro-Gly-Val-Thr-Pro-Thr-Glu-Ser-Asp-Thr-Tyr-Leu-
    X-Lys

N-Term.  Ser-Leu-Ser-Asn-Asp-X-Leu-Gly-Thr-Thr-Arg-Pro-Val-
         Met-Ser -----

FIG.5

```
DNA MIXED PROBE              --- Asp - Asp - Glu - Ala - Tyr - Val ---
T-30                         5' GAU  GAU  GAA  GCU  UAU  GUU  3'
                                  C    C    G    C    C    C
mRNA                  YS012                     A    A    A
                                                G    G    G cDNA                  YS013  3' CTA  CTA  CTT  CGA  ATA  CA  5'
                                  G    G    C    C    G

T-11                         3' CTA  CTA  CTT  CGT  ATA  CA  5'
                                  G    G    C    C    G

MET - MET - GLY - HIS - GLY - HIS ---
mRNA                  YS015  5' AUG  AUG  GGU  CAU  GGU  CAU  3'
                                           C    C    C    C
                                           A    G    A    G
                                           G    T    G    T
                                                C         C cDNA                         3' TAC  TAC  CCA  GTA  CCA  GT  5'
                                           G    G    G
                                           T         T
                                           C         C
```

FIG.6

```
5' GGGGGGCCCTCAAGAAGATCGTATCCCAACAAGGAT                          -121

GTGTATTTCTGGCTACCTGTGGGGCAAGCACTAATGGAGTAGGGGGATTGATCCAGCTTC     -61

CTATTACCAGGATTACAACCCTGCCTTTAATTTCTCCTGAAGTAAGGCACAGACCATATT      -1

ATGGATATGGCCAGCCTCATTAGCAGCTTGCTTGTGCTCTTTCTCATATTTCAGAACAGC      60
MetAspMetAlaSerLeuIleSerSerLeuLeuValLeuPheLeuIlePheGlnAsnSer
                                                           -20

TGTTACTGTTTCAGAAGTCCCCTCTCTGTCTTTAAGAGGTATGAGGAATCAACCAGATCA     120
CysTyrCysPheArgSerProLeuSerValPheLysArgTyrGluGluSerThrArgSer
                                                         -1  1

CTTTCCAATGACTGCTTGGGAACCACACGGCCCGTTATGTCTCCAGGCTCATCAGATTAT     180
LeuSerAsnAspCysLeuGlyThrThrArgProValMetSerProGlySerSerAspTyr
                                                            21

ACTTTAGATATCCGAATGCCAGGAGTAACTCCGACAGAGTCGGACACGTATCTTTGCAAG     240
ThrLeuAspIleArgMetProGlyValThrProThrGluSerAspThrTyrLeuCysLys
                                                            41

TCTTACCGGCTGCCAGTGGATGATGAAGCCTACGTAGTTGACTACAGACCACATGCCAAT     300
SerTyrArgLeuProValAspAspGluAlaTyrValValAspTyrArgProHisAlaAsn
                                                            61

ATGGATACTGCACATCACATGCTCCTATTTGGATGCAATGTGCCTTCTTCCACTGATGAT     360
MetAspThrAlaHisHisMetLeuLeuPheGlyCysAsnValProSerSerThrAspAsp
                                                            81

TACTGGGACTGCAGTGCAGGAACTTGTAATGACAAATCTAGTATAATGTATGCCTGGGCA     420
TyrTrpAspCysSerAlaGlyThrCysAsnAspLysSerSerIleMetTyrAlaTrpAla
                                                           101

AAGAATGCACCACCCACCAAACTACCAGAAGGAGTTGGATTTCAAGTTGGAGGGAAATCG     480
LysAsnAlaProProThrLysLeuProGluGlyValGlyPheGlnValGlyGlyLysSer
                                                           121
```

FIG.16A

```
GGCAGTAGATATTTTGTTCTTCAAGTTCACTATGGTGATGTGAAAGCATTCCAGGATAAA      540
GlySerArgTyrPheValLeuGlnValHisTyrGlyAspValLysAlaPheGlnAspLys
                                                          141

CATAAAGATTGCACAGGGGTGACTGTACGGATAACACCTGAAAAACAACCATTAATTGCA      600
HisLysAspCysThrGlyValThrValArgIleThrProGluLysGlnProLeuIleAla
                                                          161

GGCATTTATCTTTCAATGTCTCTCAACACTGTTGTTCCACCTGGGCAAGAGGTAGTTAAT      660
GlyIleTyrLeuSerMetSerLeuAsnThrValValProProGlyGlnGluValValAsn
                                                          181

TCTGATATTGCCTGCCTCTACAACAGACCAACGATACACCCATTTGCCTACAGAGTCCAT      720
SerAspIleAlaCysLeuTyrAsnArgProThrIleHisProPheAlaTyrArgValHis
                                                          201

ACTCATCAGTTAGGGCAGGTGGTGAGCGGCTTTAGAGTCAGACATGGCAAATGGACTTTA      780
ThrHisGlnLeuGlyGlnValValSerGlyPheArgValArgHisGlyLysTrpThrLeu
                                                          221

ATTGGCAGACAAAGCCCACAGCTGCCACAGGCGTTTTACCCTGTAGAGCATCCATTAGAG      840
IleGlyArgGlnSerProGlnLeuProGlnAlaPheTyrProValGluHisProLeuGlu
                                                          241

ATTAGCCCTGGAGATATTATAGCAACCAGGTGTCTGTTCACTGCTAAAGGAAGGATGTCG      900
IleSerProGlyAspIleIleAlaThrArgCysLeuPheThrGlyLysGlyArgMetSer
                                                          261

GCGACATATATTGGGGGCACAGCTAAAGATGAAATGTGTAATTTATACATCATGTATTAC      960
AlaThrTyrIleGlyGlyThrAlaLysAspGluMetCysAsnLeuTyrIleMetTyrTyr
                                                          281

ATGGATGCTGCCCATGCTACTTCATACATGACCTGTGTACAGACAGGTAACCCAAAGCTA     1020
MetAspAlaAlaHisAlaThrSerTyrMetThrCysValGlnThrGlyAsnProLysLeu
                                                          301
```

FIG.16B

```
TTTGAAAACATCCCTGAGATTGCAAATGTTCCGATTCCTGTAAGCCCTGACATGATGATG         1080
PheGluAsnIleProGluIleAlaAsnValProIleProValSerProAspMetMetMet
                                                          321

ATGATGATGATGGGACATGGTCACCACCATACAGAAGCTGAGGCTGAGACGAATACAGCA         1140
MetMetMetMetGlyHisGlyHisHisHisThrGluAlaGluAlaGluThrAsnThrAla
                                                          341

CTTCAGCAGCCTAAACGGGAGGAGGAAGAAGAAGTATTAAATCAGGATGTCCATCTAGAA         1200
LeuGlnGlnProLysArgGluGluGluGluGluValLeuAsnGlnAspValHisLeuGluGlu
                                                          361

GATACAGACTGGCCGGGAGTGAACCTCAAAGTGGGACAAGTGTCTGGTTTAGCGCTGGAT         1260
AspThrAspTrpProGlyValAsnLeuLysValGlyGlnValSerGlyLeuAlaLeuAsp
                                                          381

CCCAAGAATAATTTGGTTATTTTCCACAGGGGGGATCATGTCTGGGATGAAAACTCATTT      1320
ProLysAsnAsnLeuValIlePheHisArgGlyAspHisValTrpAspGluAsnSerPhe
                                                          401

GATAGGAATTTTGTTTATCAACAAAGAGGAATCGGACCAATCCAGGAAAGCACCATTCTC         1380
AspArgAsnPheValTyrGlnGlnArgGlyIleGlyProIleGlnGluSerThrIleLeu
                                                          421

GTTGTTGATCCGAACACTTCTAAAGTCCTCAAGTCAACAGGGCAGAATTTGTTTTTTTTG         1440
ValValAspProAsnThrSerLysValLeuLysSerThrGlyGlnAsnLeuPhePheLeu
                                                          441

CCCCATGGCCTGACTATAGACAGAGATGGGAATTATTGGGTCACAGATGTAGCCCTTCAT         1500
ProHisGlyLeuThrIleAspArgAspGlyAsnTyrTrpValThrAspValAlaLeuHis
                                                          461

CAGGTTTTCAAAGTGGGAGCTGAAAAAGAAACGCCGCTGCTTGTATTAGGGAGGGCATTT         1560
GlnValPheLysValGlyAlaGluLysGluThrProLeuLeuValLeuGlyArgAlaPhe
                                                          481
```

FIG.16C

```
CAGCCTGGGAGCGATCGGAAGCATTTCTGTCAGCCAACTGATGTTGCAGTCGACCCCATT          1620
GlnProGlySerAspArgLysHisPheCysGlnProThrAspValAlaValAspProIle
                                                         501

ACTGGCAACTTCTTTGTGGCGGATGGCTACTGCAACAGTCGCATCATGCAATTCTCACCT          1680
ThrGlyAsnPhePheValAlaAspGlyTyrCysAsnSerArgIleMetGlnPheSerPro
                                                         521

AATGGAATGTTCATCATGCAGTGGGGAGAAGAAACATCCTCAAACCTCCCCCGACCTGGT          1740
AsnGlyMetProIleMetGlnTrpGlyGluGluThrSerSerAsnLeuProArgProGly
                                                         541

CAGTTCCGCATTCCACACAGTCTGACCATGATATCTGACCAAGGACAGCTGTGTGTGGCC          1800
GlnPheArgIleProHisSerLeuThrMetIleSerAspGlnGlyGlnLeuCysValAla
                                                         561

GACAGAGAGAACGGCCGGATTCAGTGCTTCCATGCTAAAACGGGGGAATTTGTAAAGCAA          1860
AspArgGluAsnGlyArgIleGlnCysPheHisAlaLysThrGlyGluPheValLysGln
                                                         581

ATCAAACATCAGGAATTTGGAAGAGAGGTGTTTGCTGTCTCATATGCACCAGGTGGAGTG          1920
IleLysHisGlnGluPheGlyArgGluValPheAlaValSerTyrAlaProGlyGlyVal
                                                         601

TTGTACGCTGTTAATGGAAAGCCGTACTATGGAGATTCCACCCCTGTACAAGGCTTTATG          1980
LeuTyrAlaValAsnGlyLysProTyrTyrGlyAspSerThrProValGlnGlyPheMet
                                                         621

CTGAATTTCTCCAATGGGGATATTCTAGATACATTCATTCCTGCTAGAAAGAATTTTGAA          2040
LeuAsnPheSerAsnGlyAspIleLeuAspThrPheIleProAlaArgLysAsnPheGlu
                                                         641
```

FIG.16D

```
ATGCCCCATGATATTGCTGCAGGAGATGATGGAACGGTGTATGTTGGGGATGCACATGCC     2100
MetProHisAspIleAlaAlaglyAspAspGlyThrValTyrValGlyAspAlaHisAla
                                                          661

AACGCTGTATGGAAGTTCTCCCCTTCAAAGGCAGAGCATCGATCTGTCAAAAAAGCTGGA     2160
AsnAlaValTrpLysPheSerProSerLysAlaGluHisArgSerValLysLysAlaGly
                                                          681

ATAGAGGTAGAAGAAATAACAGAAACCGAGATCTTCGAGACCCATATGAGAAGCAGACCA     2220
IleGluValGluGluIleThrGluThrGluIlePheGluThrHisMetArgSerArgPro
                                                          701

AAGACCAATGAAAGTGTTGGGCAGCAAACACAGGAGAAACCGAGTGTTGTACAAGAAAGC     2200
LysThrAsnGluSerValGlyGlnGlnThrGlnGluLysProSerValValGlnGluSer
                                                          721

AGCGCCGGCGTCTCTTTCGTTCTCATCATCACTCTTCTAATCATTCCTGTTGTGGTTCTC     2340
SerAlaGlyValSerPheValLeuIleIleThrLeuLeuIleIleProValValValLeu
                                                          741

ATCGCTATTGCAATCTTCATTCGTTGGAGGAAAGTTAGGATGTATGGAGGTGACATTGGC     2400
IleAlaIleAlaIlePheIleArgTrpArgLysValArgMetTyrGlyGlyAspIleGly
                                                          761

CACAAATCAGAATCCAGTTCAGGGGGCATCTTGGGAAAACTTCGAGGGAAGGGCAGTGGA     2460
HisLysSerGluSerSerSerGlyGlyIleLeuGlyLysLeuArgGlyLysGlySerGly
                                                          781

GGCCTTAATCTGGGAACATTCTTTGCAACGCATAAAGGATATAGTAGAAAAGGCTTTGAC     2520
GlyLeuAsnLeuGlyThrPhePheAlaThrHisLysGlyTyrSerArgLysGlyPheAsp
                                                          801

AGGCTGAGTACAGAAGGAAGCGACCAAGAGAAAGATGATGATGATGATGGCTCAGACTCT     2580
ArgLeuSerThrGluGlySerAspGlnGluLysAspAspAspAspAspGlySerAspSer
                                                          821
```

FIG.16E

```
GAAGAAGAGTATTCTGCCCCGCCTATTCCACCAGTATCTTCCTCCTGAAACAGTTGACTT      2640
GluGluGluThrSerAlaProProIleProProValSerSerSer***
                                              836

CTTCCGTACAACCTTTTGCTCCATTAGCACGTTTAAAATGGTGTATTTAAATGTTACTGT      2700

ACTAGTCTGTGGACTGTACAATCGTCATAGCTTTTATTTTTATTTGAAGTGCTGTTGTAG      2760

CCTTTATATGAACATTCAGAATAATTCTATTTGGTCAATGACTTTGGCTTTTCCAGTGTT      2820

TGATGGCCTTCCTCTGCTTCACCAAGAGCACTTTAACTGCCAATTATTTTCAAGCCTTTA      2880

ACTGAAATCGAATCGCATTACAAGGATACGTGCCACATAAATGCAAAGCTGCTAAATCTC      2940

TTCTATTTTTTTAAATTAACAACACGATGTCGCGCTCAAGAAAGGAAACGATAAAGACAT      3000

AATATTTAATGTTTCTTATTTCTTTCTATTTTTTTTTCATTGTTTTTGGTGTTCTTGGGG      3060

TGTGTAATAAAGTGTTCGCAGCCCCCCCCCCCCCCCCCCCTGCAG  3'                 3159
```

FIG. 16F

```
                 -37             -30             -20             -10              -1              10              20              30
pXA 457          MASLSSSFLVLFLLLFWNSCYCFRSPLSVFKRYEESTRSLSNDCLGTTRPVMSPGSSDYTLDIRMPGV
                     *       *                *
pXA 799      MDMASLISSLLVLFLIFQNSCYCFRSPLSVFKRYEESTRSLSNDCLGTTRPVMSPGSSDYTLDIRMPGV 40              50              60              70              80              90
pXA 457       TPTESDTYLCKSYRLPVDDEAYVVDFRPHANMDTAHHMLLFGCNIPSSTDDYWDCSAGTCMDKSSIMY
pXA 799       TPTESDTYLCKSYRLPVDDEAYVVDYRPHANMDTAHHMLLFGCNVPSSTDDYWDCSAGTCNDKSSIMY 100             110             120             130             140             150             160
pXA 457       AWAKNAPPTKLPEGVGFRVGGKSGSRYFVLQVHYGNVKAFQDKHKDCTGVTVRVTPEKQPQIAGIYLS
                                                  *                                *
pXA 799       AWAKNAPPTKLPEGVGFQVGGKSGSRYFVLQVHYGDVKAFQDKHKDCTGVTVRITPEKQPLIAGIYLS 170             180             190             200             210             220             230
pXA 457       MSVDTVIPPGEEAVNSDIACLYNRPTIHPFAYRVHTHQLGQVVSGFRVRHGKWSLIGRQSPQLPQAFY
              **    *      **                                              *
pXA 799       MSLNTVVPPGQEVVNSDIACLYNRPTIHPFAYRVHTHQLGQVVSGFRVRHGKWTLIGRQSPQLPQAFY
```

FIG. 19A

```
         240        250        260        270        280        290        300
pXA457   PVEHPVEISPGDIIATRCLFTGKGRTSATYIGGTSNDEMCNLYIMYYMDAAHATSYMTCVQTGEPKLF
             *                             **                             *
pXA799   PVEHPLEISPGDIIATRCLFTGKGRMSATYIGGTAKDEMCNLYIMYYMDAAHATSYMTCVQTGNPKLF 310        320        330        340        350        360
pXA457   QNIPEIANVPIPVSPDMMMM--GHGHHHTEAEPEKNTGLQQPKREEEVLDQGLITLGDSAV
          *                 **                * * *           **********
pXA799   ENIPEIANVPIPVSPDMMMMMMGHGHHHTEAEAETNTALQQPKREEEVLNQDVHLEEDTDW------
```

FIG. 19B

DNA (I)

5' GTCATTGGAAAGTGACATGAATTCTTCCTCAT
ACCTCTT 3'

ENZYMATIC PRODUCTION OF A C-TERMINAL α-AMIDATED PEPTIDE OR PROTEIN

This application is a divisional, of application Ser. No. 07/509,583, filed Apr. 16, 1990, now U.S. Pat. No. 6,245,387 which is a divisional of application Ser. No. 07/219,375, filed Jul. 15, 1988 now U.S. Pat. No. 6,262,232.

BACKGROUND OF THE INVENTION

1. Field of the Invention

The present invention relates to recombinant C-terminal α-amidated enzymes of *Xenopus laevis* origin and precursors thereof, DNAs coding for these poly-peptides, plasmids containing the DNA, host cells transformed with the plasmid, a process for the production of the enzyme or precursor thereof using the transformed cells, and a process for the production of a C-terminal α-amidated peptide or protein using the enzyme.

2. Related Art

It is generally known that, in eukaryotic cells, some kinds of peptides or proteins are, after translation from a messenger RNA (mRNA), modified by an intracelular enzyme to mature to a natural-type peptide or protein (post-translational modification). But, since prokaryotic hosts such as *E. coli*, which are widely used to produce peptides or proteins of eukaryote origin, cannot carry out a post-translational modification of an expressed peptide or protein, it is sometimes difficult to directly produce a eukaryotic peptide or protein by a recombinant DNA technique using prokaryotic host cells.

One of this post-translational modification characteristic of eukaryotic cells of peptides or proteins is a modification reaction wherein an α-position of a carboxy terminal (C-terminal) of a peptide or protein is amidated, i.e., —COOH is converted to —CONH$_2$, and it is known that many physiologically active peptides or proteins have been subjected to such modification. For example, as C-terminal α-amidated peptides (SEQ ID NOS:1 & 2), TRH(pGlu-His-Pro-NH$_2$) and

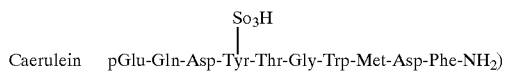

have been isolated, and a partial structure of precursors of these peptide determined from an analysis of the CDNA thereof. A general biosynthesis mechanism of such amidated peptides is understood to be that in which RNA is translated to a precursor of an amidated peptide, which is then amidated at the α-position of the C-terminal thereof by a C-terminal α-amidating enzyme. Note, in the above-mentioned reaction, the precursor of the C-terminal α-amidated peptide as a substrate for a C-terminal α-amidating enzyme is a peptide or protein represented by a general formula R—X-Gly, wherein R represents an amino acid sequence of the N-terminal side of the peptide or protein, X represents an amino acid residue which is to be α-amidated at the C-terminal thereof, and Gly represents a glycine residue.

It is known that, in some cases, the above-mentioned modification of peptide or protein is essential to the physiological activity thereof. For example, a conversion of the proline amide residue at the C-terminal of natural-type human calcitonin to proline residue decreases the physiological activity thereof to ¹⁄₁,₆₀₀ of the original activity.

Because of the importance of clarifying the mechanism of a-amide formation in tissues, and the promising usefulness of the enzyme for the production of C-terminal α-amidated peptides using, for example, recombinant DNA techniques, many attempts to purify the enzyme have been made but the enzyme has not so far been obtained in a pure state. In porcine pituitary, Bradburg, A. F. et al, *Nature* 298, 686–688, 1982, first characterized the α-amidating activity converting a synthetic substrate D-Tyr-Val-Gly to D-Tyr-Val-NH$_2$, and demonstrated that the C-terminal glycine in the substrate serves as a nitrogen-donor for α-amidation. Eipper et al, *Proc. Natl. Acad. Sci. US*, 80, 5144–5148, 1983, reported that the α-amidated enzyme derived from the pituitary gland requires copper cation and ascorbate for its activity. Husain, I. et al, *FEBS Lett.*, 152 227–281, 1983; and Kizer, J. S. et al, *Proc. Natl. Acad. Sci. US*, 81, 3228–3232, 1984, also reported a C-terminal α-amidating enzyme, but did not report a purified enzyme. Recently, Murthy A. S. N. et al, *J. Biol. Chem.*, 261, 1815–1822, 1986, partially purified a C-terminal α-amidating enzyme from the pituitary gland of cattle, and showed that several types of enzymes having different molecular weights and electric charges are present. Nevertheless, no type of enzyme has been homogeneously purified.

Recently, Mizuno et al. succeeded in isolating a C-terminal α-amidating enzyme in a homogeneous and pure form from a skin of *Xenopus laevis*; see Mizuno, K et al, *Biochem. Biophys. Res. Commun.* 137, 984–991, 1988, and Japanese Patent Application No. 61-131089.

Nevertheless, the amount of the C-terminal α-amidating enzyme isolated from a skin of *Xenopus laevis* is limited, and not sufficient for use in the industrial production of C-terminal α-amidated peptides or proteins.

SUMMARY OF THE INVENTION

Accordingly, the present invention provides a recombinant DNA technique for the production of a C-terminal α-amidating enzyme and the large amount of thus-produced enzyme, as well as the use of the enzyme for the production of C-terminal α-amidated peptides or protein.

More specifically, the present invention provides a C-terminal α-amidated enzyme of *Xenopus laevis* and precursors thereof produced by a recombinant DNA technique.

The present invention also provides a DNA coding for a C-terminal α-amidating enzyme of *Xenopus laevis* or precursor thereof.

Further, the present invention provides a plasmid containing a DNA coding for a C-terminal α-amidating enzyme of *Xenopus laevis* or precursor thereof.

Moreover, the present invention provides host organisms transformed with a plasmid containing the DNA coding for a C-terminal α-amidated enzyme of *Xenopus laevis* or precursor thereof.

Still further the present invention provides a process for the production of a C-terminal α-amidating enzyme of *Xenopus laevis* and precursor thereof comprising the steps of, culturing a host organism transformed with a plasmid containing a DNA coding for the enzyme or precursor thereof to produce the enzyme or precursor thereof, and recovering the enzyme or precursor thereof.

Also, the present invention provides a process for the production of a C-terminal α-amidated peptide or protein characterized by reacting the above-mentioned enzyme with a peptide or protein having a glycine residue at the C-terminal thereof.

BRIEF EXPLANATION OF THE DRAWINGS

FIGS. 1A to 1E (SEQ ID NO:34) show an entire nucleotide sequence of CDNA in a plasmid pXA457 and an amino acid sequence encoded by the cDNA, which nucleotide sequence contains a nucleotide sequence coding for an amino acid sequence of a first type of prepro-C-terminal α-amidating enzyme as well as a 5'-terminal and 3'-terminal non-coding sequences;

FIGS. 2A to 2C (SEQ ID NO:35) show an amino acid sequence of a C-terminal α-amidating enzyme which corresponds to the first amino acid to the 344th amino acid in FIGS. 1A–1D, and a corresponding nucleotide sequence;

FIGS. 3A to 3C (SEQ ID NO:36) show an amino acid sequence of a pre-C-terminal α-amidating enzyme which corresponds to the first amino acid to the 363th amino acid in FIGS. 1A–1D, and a corresponding nucleotide sequence;

FIGS. 4A to 4D (SEQ ID NO:37) show an amino acid sequence of a prepro-C-terminal α-amidating enzyme which corresponds to the −37th amino acid to the 363th amino acid in FIGS. 1A–1D, and a corresponding nucleotide sequence;

FIG. 5 (SEQ ID NOS:38–51) shows an N-terminal amino acid sequence (T-Term) of a native C-terminal α-amidating enzyme isolated from a skin of *Xenopus laevis*, and amino acid sequences of tryptic fragments (T-numbers) of the native enzyme;

FIG. 6 (SEQ ID NOS:52–58) shows a design of mixed probes YSO12, YSO13, and YSO15 used for isolation of a cDNA coding for a C-terminal α-amidating enzyme derived from *Xenopus laevis*, on the basis of amino acid sequences of the tryptic fragments T-11 and T-30;

FIGS. 16A to 16F (SEQ ID NO:62) show a nucleotide sequence of cDNA in a plasmid pXA799, and an amino acid sequence coded by the cDNA. The cDNA contains a nucleotide sequence coding for a second type of C-terminal α-amidating enzyme;

FIGS. 19A to 19B (SEQ ID NOS:63–64) shows a comparison of primary amino acid sequences of proteins coded by cDNA's in plasmids pXA457 and pXA799;

DESCRIPTION OF THE PREFERRED EMBODIMENTS

Figure 7A:
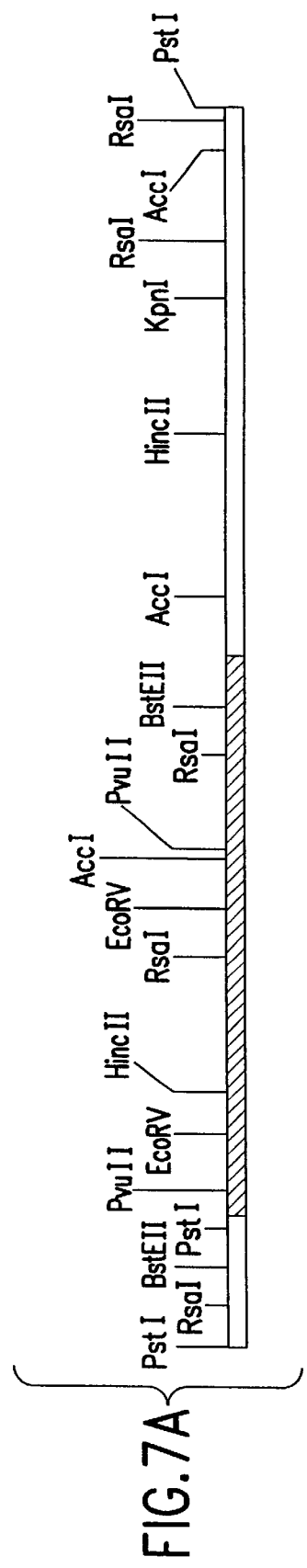
FIGS. 7A and 7B shows a restriction enzyme cleavage map (7A) of cDNA in the plasmid pXA457, and a strategy used to determine a nucleotide sequence of the cDNA (7B)

The present inventors isolated a C-terminal α-amidating enzyme in homogeneous pure form from a skin of *Xenopus laevis*, and determined partial amino acid sequences of the enzyme. Next, DNA probes were prepared on the basis of the partial amino acid sequences, and the probes were used to screen a cDNA library derived from a skin of *Xenopus laevis* to obtain a single clone containing a CDNA coding for a C-terminal α-amidating enzyme.

Moreover, the entire primary amino acid sequence of a C-terminal α-amidating enzyme (see FIGS. 2-1 to 2-3) and precursors thereof, i.e., pre-enzyme (FIGS. 3-1 to 3-3) and prepro-enzyme (FIGS. 4-1 to 4-3), were determined on the basis of the nucleotide sequence of the cDNA. Next, the cDNA was tailored and introduced into a plasmid to construct an expression plasmid, which was then transformed into *E. coli* cells to economically produce a large amount of the C-terminal α-amidating enzyme.

As mentioned above, although it was known that a skin of *Xenopus laevis* contains at least TRH and caerulein as C-terminal α-amidated peptides, it was not clear whether these C-terminal α-amidated peptide were synthesized only by the above-mentioned C-terminal α-amidated enzyme. In other words, there was a possibility that other enzymes having an activity similar to that of the above-mentioned enzyme present in a skin of *Xenopus laevis* and different C-terminal α-amidated peptides or proteins were biosynthesized by a different C-terminal α-amidating enzyme. Accordingly, the present inventor again attempted to screen a cDNA library derived from a skin of *Xenopus laevis* using the above-mentioned cDNA as a probe, and as a result, the present inventor identified another cDNA coding for an enzyme which has an activity similar to that of the above-mentioned C-terminal α-amidating enzyme but has an amino acid sequence different from that of the above-mentioned enzyme, and further, succeeded in expressing the second enzyme.

Moreover, the present inventors developed a process for the production of a C-terminal α-amidated peptide or protein from a substrate peptide or protein having a glycine residue at the C-terminal thereof.

In the present invention, a C-terminal α-amidating enzyme is an enzyme which converts a peptide or protein represented by the formula R—X-Gly, wherein R represents an amino acid sequence of the N-terminal side of the peptide or protein, X represents an amino acid residue which is to be α-amidated at the C-terminal thereof, and Gly represents a glycine residue to a peptide or protein represented by the formula R—X—$NH_2$, wherein R and X have the same meanings as defined above.

A C-terminal α-amidating enzyme of *Xenopus laevis* origin includes an enzyme which is present in a skin of *Xenopus laevis* and has the above-mentioned enzyme activity, and modified proteins wherein at least one amino acid of a native enzyme is deleted, or replaced with another amino acid(s), or at least one amino acid is added to the native enzyme.

The present invention is now described in more detail.

(1) Purification of a C-terminal α-Amidating Enzyme and Determination of a Partial Amino Acid Sequence of the Enzyme A C-terminal α-amidated enzyme is purified in a homogeneous form from a skin of *Xenopus laevis* according to a method disclosed by Mizuno et al., in *Biochem. Biophys. Res. Commun.* 137, 984–991, 1986. Hereinafter, this enzyme is referred to as a "native enzyme". More specifically, a skin of *Xenopus laevis* is washed with an appropriate buffer and disrupted by a physical means, to elute the enzyme, and the enzyme is recovered and purified from the resulting eluate.

Next, the enzyme is hydrolyzed with trypsin to generate peptide fragments (tryptic fragments) which are then fractionated and purified by reverse phase high performance liquid chromatography (HPLC). An amino acid sequence of each tryptic fragment is determined by a protein sequencer. On the other hand, an N-terminal amino acid sequence of the native enzyme is determined from the native enzyme by a protein sequencer. (See FIG. 5)

(2) Isolation of cDNA of C-terminal α-Amidating Enzyme

A total RNA mixture is prepared from a skin of *Xenopus laevis* according to a conventional procedure, and poly (A) RNA is prepared from the total RNA using an oligo (dT) cellulose column. Next, cDNA is prepared from the thus-prepared poly (A) RNA according to a method of Gubler, V. and Hoffman, B. J., *Gene* 25, 263, 1983, and the cDNA is transfected into an *E. coli* K12-derived strain DH1 to construct a cDNA library of *Xenopus laevis* origin. To isolate a cDNA coding for a target C-terminal α-amidating enzyme from the cDNA library, oligonucleotide probe mixtures, for example, YS012, YS013, YS015 and the like (see FIG. 6) are prepared on the basis of partial amino acid sequences such as T-11, T-30, and the like (see FIG. 5).

Next, each probe mixture is labeled at the 5'-terminal thereof using [γ-$^{32}$P]ATP and $T_4$ poly-nucleotide kinase, and the labeled probe mixtures are then used to screen the cDNA library in an *E. coli* K12-derived strain DH1 to obtain a single cDNA clone, such as *E. coli* DH1/pXA457, coding for a C-terminal α-amidating enzyme of *Xenopus laevis*.

Further, a DNA probe is prepared by radio-labeling a cDNA fragment coding for a part of a C-terminal α-amidating enzyme, for example, a PvuII cDNA fragment from the 54th nucleotide C to the 795th nucleotide G in the plasmid pXA457 shown in FIGS. 1-1 to 1-2, through nick-translation using [α-$^{32}$P]CTP. The probe thus prepared is used to screen the cDNA library in an *E. coli* R12-derived strain DH1 to obtain another single clone, for example *E. coli* DH1/pXA799, containing CDNA coding for a C-terminal α-amidating enzyme different from the above-mentioned enzyme.

(3) Analysis of cDNA Coding for C-Terminal α-Amidated Enzyme

Figure 7B:
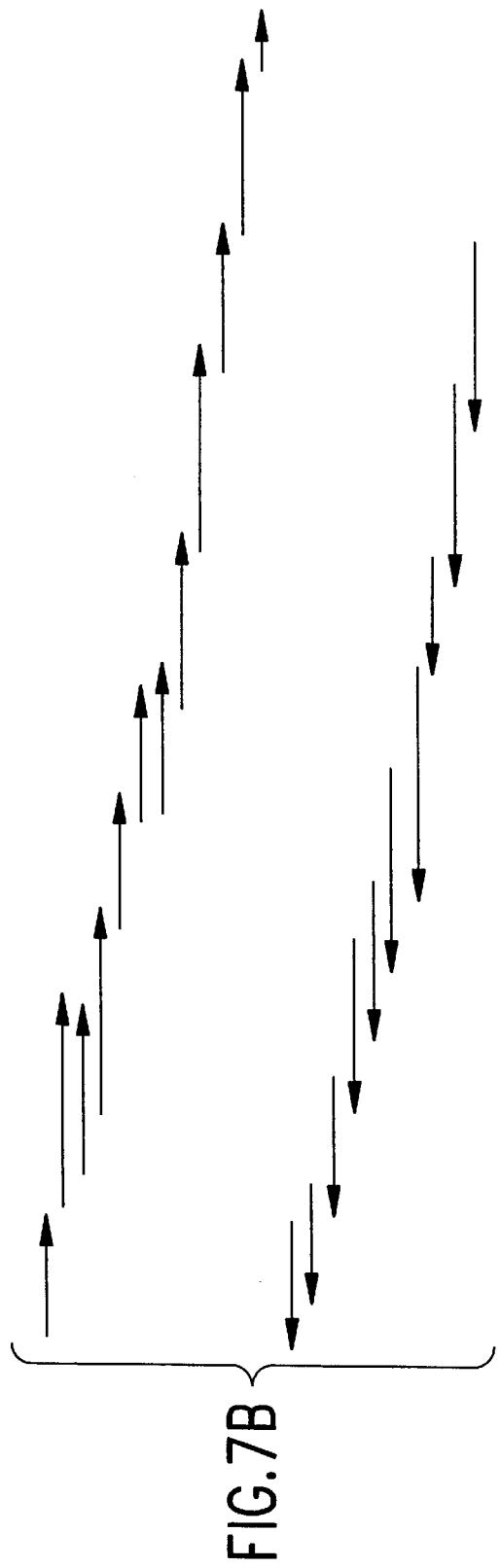

According to a conventional procedure, a plasmid such as pXA457 is isolated from the above-mentioned single clone, and the plasmid is cleaved with various kinds of restriction enzymes to make a restriction enzyme cleavage map of the cDNA (see FIG. 7(a)). Next, each cDNA fragment generated by restriction enzymes is sub-cloned into M13 phage, and a nucleotide sequence of a cDNA insert in each clone is determined by a method of Sanger F. et al., *Proc. Natl. Acad. Sci. USA*, 34, 5463–5467 (1977) (see FIG. 7(b)).

An analysis of a nucleotide sequence of the cDNA in the plasmid pXA457 revealed that:

1) the cDNA contains a long open reading frame starting with the first nucleotide and terminating at the 1200th nucleotide in FIGS. 1-1 to 1-3;
2) a primary amino acid sequence expected from this open reading frame consists of 400 amino acid residues starting with the N-terminal Met-Ala-Ser- and ending at the C-terminal -Ser-Ala-Val; and
3) this primary amino acid sequence contains all of the above-mentioned partial amino acid sequences (amino acid sequences of tryptic fragments shown in FIG. 5) of the native enzyme. The above-mentioned analysis shows that the plasmid pXA457 contains a cDNA coding for an entire amino acid sequence of the target enzyme.

The N-terminal amino acid sequence of the native enzyme has ralready been determined from an analysis of protein (SEQ ID NO:3) level as Ser-Leu-Ser-Asn-Asp-(FIG. 5). This amino acid sequence corresponds to an amino acid sequence starting with Ser (1) in an amino acid sequence expected from the nucleotide sequence of cDNA, as shown in FIG. 1-1, and therefore, an amino acid sequence portion from Met (−37) to Arg (−1) underlined in FIG. 1-1 in the amino acid sequence expected from the nucleotide sequence is assumed to be a signal sequence necessary for a secretion of protein. The presence and function of a signal sequence has been already clarified in many other secretion proteins, and accordingly, it is expected that a the native enzyme is first synthesized from Met (−37), and the peptide portion from Met (−37) to Arg (−1) is removed by a signal peptidase or other processing enzyme to produce the native enzyme.

Although the C-terminal amino acid sequence of native enzyme expected from cDNA analysis is -Ser-Ala-Val-OH, the C-terminal amino acid sequence at protein level has not yet been determined. Accordingly, to determine the C-terminal structure of the native enzyme, the present inventor carried out the following experiments.

First, since the N-terminal amino acid sequence has been determined as Ser-Leu-Ser-, if the C-terminal amino acid sequence is Ser-Ala-Val-OH, as assumed from the cDNA, a theoretical molecular weight of the native enzyme calculated from an amino acid sequence expected from the cDNA is 40114, which is larger than a molecular weight of about 39000 obtained from a native enzyme purified from *Xenopus laevis* by SDS-PAGE analysis.

Moreover, in a comparison between an amino acid composition of native enzyme which has been determined by amino acid analysis and set forth in Table 1, and a theoretical amino acid composition calculated from an amino acid sequence expected from cDNA, it was found that the number of glutamic acid residues and the number of leucine residues determined by amino acid analysis are lower than those calculated from the nucleotide sequence, by 4 to 5, and 3 respectively. On the other hand, the amino acid sequence expected from the cDNA contains a sequence Lys (344)-Arg (345) at a position near the C-terminal, and it is known that this amino acid sequence is a recognizing site for a processing enzyme (protease) in precursors of many physiologically active peptides, and that this site is cleaved to convert the precursors to physiologically active mature peptides. Therefore, in the case of the present C-terminal α-amidated enzyme, it is likely that a peptide linkage between Lys (344)-Arg (345) is cleaved to convert a precursor peptide to the native enzyme. This speculation conforms to the facts that:

1) an amino acid composition calculated for an amino acid sequence from Ser (1) to Lys (344) is similar to an amino acid sequence determined from the native enzyme;
2) a theoretical molecular weight calculated from the amino acid sequence from Ser (1) to Lys (344) is similar to a molecular weight determined from a native enzyme; and
3) the amino acid sequence: H-Asn-Thr-Gly-Leu-Gln-Gln-Pro-Lys-OH of the tryptic fragment T-9 corresponds to an amino acid sequence: Asn(337)-Thr(338)-Gly(339)-Leu(340)-Gln(341)-Gln(342)-Pro(343)-Lys (344) expected from the cDNA.

Accordingly, to prove the above-mentioned possibility, the present inventors carried out the following experiments: (1) expression of cDNA portions of nucleotides 112 to 1200, and of nucleotides 112 to 1143 (the nucleotide numbers correspond to those in FIGS. 1-1 to 1-4), in *E. coli*; (2) comparison of molecular weights of two proteins expressed in *E. coli* as above and the native enzyme by SDS-PAGE; and (3) separation of the proteins expressed in *E. coli* by SDS-PAGE and isolation of the target proteins from the gel, determination of the amino acid compositions of these proteins, and comparison of the amino acid compositions with that of the native enzyme. As a result, it was strongly suggested that a primary amino acid sequence of the native enzyme is identical to a primary amino acid sequence coded by a cDNA portion (112–1143) in pXA457 (see Table 1 and FIG. 14(*b*)).

According to the same procedure as described above for the first plasmid pXA457, another plasmid pXA799 is isolated from a second single clone selected from a cDNA library using the first cDNA as a probe. Next, a restriction enzyme cleavage map of cDNA in the plasmid pXA799 is made, and a nucleotide sequence of the cDNA is determined. The result is shown in FIGS. 16-1 to 16-3. An analysis of the result revealed the following:

1) The cDNA contains a long open reading frame starting with the nucleotide and terminating at 2625 of the nucleotide in FIGS. 16-1 to 16-3, and coding a protein consisting of 875 amino acid residues. Note, since a translation stop codon TAA is present at position-18 to -16 in FIG. 16-1, methionine coded by nucleotides No. 1 to 3 in FIG. 16-1 is a translation start codon of this protein.
2) As shown in FIGS. 19-1 to 19-2, in a comparison of a primary amino acid sequence of a protein coded by the cDNA in pXA799 and a primary amino acid sequence of a prepro-C-terminal α-amidating enzyme coded by cDNA in pXA457, an N-terminal side (amino acid No. -37 to 350) of the protein coded by the cDNA in pXA799 is very similar to that for pXA457. Note, the similarity between the above-mentioned two primary amino acid sequences is conserved at processing sites, i.e., N-terminal site and C-terminal site, of precursor proteins.
3) Nevertheless, the C-terminal side of the protein coded by cDNA in pXA799 is completely different from that of pXA457. Namely, the open reading frame in the cDNA in pX7799 is largely extended to the 3'-terminal.
4) The extended portion contains a three Asn-X-Ser sequence wherein X represents any amino acid residue, corresponding to an amino acid number 426–428, 623–625, and 704–706 in FIGS. 16-2–16-3. The sequence Asn-X-Ser is known to be a N-glycosylation site in many glycoproteins, and therefore, a protein coded by the cDNA in pXA799 is also likely to be N-glycosylated.
5) The protein coded by the cDNA in pXA799 contains a region from the amino acid number 727 to 748 comprising hydrophobic amino acids, as well as basic amino acids, i.e., arginine and lysine immediately after the hydrophobic region. Since a similar structure has been identified in many membrane proteins at the transmembrane domain thereof, the protein coded by the cDNA in pXA799 is likely to be present as a membrane protein.

From the above-mentioned analysis of cDNA in pXA799, and of a primary amino acid sequence coded by the cDNA, the protein coded by the cDNA in pXA799 is completely different from the C-terminal α-amidating enzyme coded by the cDNA in pXA457. But, so far, a protein expected from the cDNA in pXA799 has not been isolated and purified from *Xenopus laevis*. Therefore, the mechanism of biosynthesis of a protein expected from the cDNA in pXA799 (cleavage of N-terminal and C-terminal, presence or absence of glycosylation, etc.), the location in vivo of the protein, as well as the function of the protein (presence or absence of C-terminal α-amidating activity) are not clear. Therefore, to clarify these questions, the present inventors used the cDNA in pXA799 to express in *E. coli* a protein coded by the cDNA and protein derivatives thereof, and the C-terminal α-amidating activities of these proteins were measured.

From a comparison of the cDNA in pXA457, the cDNA in pXA799, and the N-terminal amino acid sequence of the native enzyme, it is considered that a peptide portion from amino acid number -39 to -1 in FIG. 16-1 is a signal peptide necessary for secretion of the protein, and a peptide bond between amino acid -1 and amino acid 1 is cleaved during biosynthesis of a mature protein. Therefore, a mature protein corresponding to a protein coded by the cDNA in pXA799 starts with the amino acid 1 in FIG. 16-1, and has an N-terminal amino acid sequence (SEQ ID NO:4): H-Ser-Leu-Ser-Asn-Asp- - - -.

Figure 20:
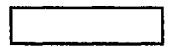
FIG. 20 (SEQ ID NOS:65–68) shows a protein coded by cDNA in pXA799 and derivatives thereof, as well as corresponding plasmids.

But, with regard to a mechanism for a biosyn-thesis of a C-terminal portion, the glycosylation, post-translation modification such as a cleavage of the C-terminal portion, and the relationship between the C-terminal structure and C-terminal α-amidating activity, have not been known. To clarify these points, a full length peptide starting from amino acid 1 and terminated at amino acid 836, i.e., having an amino acid sequence (SEQ ID NOS:4 & 5) H-Ser(1)-Leu-Ser-Asn-Asp- - - - -Pro-Pro-Val-Ser-Ser-Ser-OH(836), and various peptides starting from amino acid 1 and having a shortened C-terminal terminated at different sites, are expressed in *E. coli*, and the enzyme activity of each protein is determined. FIG. 20 schematically shows structures of these proteins, names of the plasmids used for the expression of these proteins, and the enzyme activity. Note, in some cases, since a multi-cloning site is introduced into an expression plasmid during construction of the plasmid, the protein has a C-terminal amino acid sequence different from the amino acid sequence of pXA799 origin. In such a case, the different amino acid sequence is shown in FIG. 20 for each protein.

(4) Expression of C-terminal α-amidating Enzyme in Host Cells

To express a C-terminal α-amidating enzyme coded by cDNA derived from pXA457 in host cells such as *E. coli*, expression vectors such as ptrpXAST8 and ptrpXDAST8 are constructed. These expression vectors are designed to express cDNA under the control of an appropriate expression control sequence, for example, a tryptophan operon functional in host cells such as *E. coli* (promoter, operator, and Shine-Dalgarno sequence of tryptophan leader peptide). Next, the expression vector is used to transform host cells such as *E. coli* W3110 to obtain transformatns such as *E. coli* W3110/ptrpXAST8 and *E. coli* W3110/ptrpXDAST8.

On the other hand, to express a terminal α-amidating enzyme coded by cDNA derived from pXA799, expression vectors such as $pUCP_LCI799Dra$ I, $pUCP_LCI799Bgl$ II, $pUCP_LCI799R$ V, $pUCP_LCI799Sal$ I, $pUCP_LCI799BstE$ $II^L$, $pUCP_LCI799BstE$ $II^S$, ptrpΔ799, ptrp799-457Δ, and the like are constructed. These expression vectors are designed to express a protein coded by the cDNA in pXA799, or shortened protein derivatives under an appropriate expression control sequence such as λ phage $P_L$ promoter for $pUCP_LCI$ series plasmids, or an *E. coli* tryptophan promoter for ptrp series plasmids. Next, these vectors are used to transform host cells such as *E. coli* W3110, to obtain transformants for expression, such as *E. coli* W3110/$pUCP_LCI799Dra$ I, *E. coli* W3110/$pUCP_LCI799Bgl$ II, *E. coli* W3110/$pUCP_LCI799R$ V, *E. coli* W3110/$pUCP_LCI799Sal$ I, *E. coli* W3110/$pUCP_LCI799BstE$ $II^S$, *E. coli* W3110/$pUCP_LCI799$-BstE $II^L$, *E. coli* W3110/ptrp 799 and *E. coli* W3110/ptrp799-457Δ).

Next, these transformants and the control *E. coli* W3110 are separately cultured, cultured cells are collected, and the whole protein in the cultured cells is analyzed by SDS-acrylamide gel electrophoresis (SDS-PAGE). As a result, it was found that *E. coli* W3110/ptrpXAST8 and *E. coli* W3110/ptrpXDAST8 produced specific proteins having molecular weights of about 40 K and about 38 K, compared to total protein produced by a control *E. coli* W3110. Other transformants are also confirmed to produce target proteins.

Most of the portion of a protein thus expressed is recovered in a precipitation fraction in a conventional cell disruption process, such as ultra-sonication or French press disruption.

(5) Assay of Enzyme Activity

A C-terminal α-amidating enzyme activity is assayed to confirm that a protein expressed in a transformant host is a C-terminal α-amidating enzyme, and that when a C-terminal α-amidating enzyme acts on the substrate thereof, an amidated peptide or protein is produced. For an assay of an expression of an enzyme in *E. coli*, *E. coli* cells are disrupted and the disruptant is centrifuged to obtain a precipitate containing a major portion of the expression product, the precipitate is solubilized with 6 M guanidine hydrochloride, and the solution thus obtained is dialyzed to obtain an assay sample.

Enzyme activity is assayed by using a reaction wherein a substrate generally represented by R—X-Gly is converted to R—X—$NH_2$, for example, a reaction wherein a synthetic substrate [$^{125}I$] -Ac-Tyr-Phe-Gly is converted to [$^{125}I$] -Ac-Tyr-Phe-$NH_2$.

Namely, first a labeled substrate (labeled R—X-Gly) is subjected to a reaction with a test enzyme solution in Tris-HCl buffer, to this reaction mixture are added Tris-HCl buffer and ethyl acetate, and after mixing, the whole is centrifuged to separate an organic phase and an aqueous phase. Since a major portion of the unreacted labeled substrate (labeled R—X-Gly) transfers to an aqueous phase, and an amidated labeled products (labeled R—X—$NH_2$) transfers to an organic phase, the substrate and the product can be easily separated.

In examples of the present invention, a C-terminal α-amidating enzyme of the present invention was assayed using synthetic peptide [$^{125}I$] -Ac-Tyr-Phe-Gly as a substrate according to the following procedure. [$^{125}I$] -Ac-Tyr-Phe-Gly (1 pmole, 70,000–150,000 cpm) was incubated with an enzyme preparation, in a final volume of 250 μl containing 0.2 M Tris-HCl buffer (pH 7.0), 2 μM $CuSO_4$, 0.25 mM ascorbic acid, 25 μg catalase (Boehringer), 0.1% Lubrol (PX type, Nakarai Chemicals). The reaction mixture was kept at 37° C. for 1 to 4 hours, and then 0.75 ml of 1 M Tris-HCl buffer (pH 7.0) and 2 ml of the organic phase of an ethyl acetate/water mixture was added. The two phases were mixed vigorously in a Vortex mixer, and after centrifugation at 3000 rpm for 3 mins, the organic phase thus separated was transferred to another test tube. The radioactivity in the organic and aqueous layers was measured by a gamma scintillation counter. Under the conditions described above, over 98% of the radioactivity of the authentic [$^{125}I$] -Ac-Tyr-Phe-Gly was retained in an aqueous phase and over 98% of the radioactivity of the authentic [$^{125}I$] -Ac-Tyr-Phe-$NH_2$ was transferred to an organic phase.

The yield of conversion is calculated from the ratio of the radioactivity in an organic phase such as an ethyl acetate phase to the total radioactivity. In this assay, one unit is defined as the enzyme activity that gives fifty percent conversion of 1 p mole substrate, such as [$^{125}I$] -Ac-Try-Phe-Gly, to [$^{125}I$] -Ac-Tyr-Phe-$NH_2$.

Where a crude extract from the skin of *Xenopus laevis* is assayed, the above-mentioned ethyl acetate layer is purified by reserve-phase HPLC using a μBondapak C-18 column, (Waters) before measurement of the radioactivity. Elution is carried out with a linear gradient of $CH_3CN$ concentration from 10 to 50% in 10 mM ammonium formate (pH 4.0) at a flow rate of, for example, 2.0 ml/min. A peak of radioactivity appears at the same position on that of an authentic peptide having the formula R—X—$NH_2$, under the same condition. This means that the labeled R—X-Gly is converted to the labeled R—X—$NH_2$, and therefore, the expressed protein has a C-terminal α-amidating activity.

(6) Process for α-Amidation of Peptide

The present enzyme products can be used to α-amidate a peptide. In this process, a substrate peptide having a glycine residue at the C-terminal thereof is incubated with one of the present enzyme products in an aqueous reaction medium, preferably in an aqueous buffer such as Tris-HCl, at a pH of about 6 to 7, and at a temperature of about 37° C., for a time sufficient to convert a substantial amount of the starting peptide to a corresponding C-terminal α-amidated peptide.

Although the present invention is directed to a C-terminal α-amidating enzyme of the skin of *Xenopus laevis*, other various kinds of animal tissue have been known to contain a similar enzyme activity. The properties of these enzymes are similar to those of the enzyme of the present invention, in that they require Cu ion for their activity; they are inhibited by a thiol compound such as dithiothreitol; the enzyme activity is lowered in the absence of ascorbic acid; and they require molecular oxygen. Therefore, it is presumed that the amino acid sequences of active domains of these enzymes are conserved, and accordingly, the cDNA of the present invention could be used as a probe to screen the mRNA or cDNA of other animals, to identify an mRNA or cDNA coding for enzymes similar to the present enzyme.

Although the present invention discloses in detail a process for the production of a C-terminal α-amidating enzyme using the cDNA in an *E. coli* host, the present cDNA can be used to express the target enzyme in another host, such as yeast or animal cells. Moreover, since various kinds of derivatives of the enzyme can be prepared by the present invention, it is expected that other modified proteins, such as proteins wherein one or more than one amino acid is added, proteins wherein one or more than one amino acid is deleted, and proteins wherein one or more than one amino acid is replaced by another amino acid(s), would exhibit a C-terminal α-amidating activity. Accordingly, the present enzymes include, in addition to the enzymes coded by the cDNA of *Xenopus laevis*, modified proteins having a C-terminal α-amidated activity.

As described above, the present inventors isolated the cDNA coding for a C-terminal α-amidating enzyme from the skin of *Xenopus laevis*, clarified the structure of the cDNA, and provided a process for the production of the above-mentioned enzyme. The cDNA can be used not only in a bacterial host such as *E. coli* but also in a eukaryotic host such as yeast or animal cells, to produce a large amount of the target enzyme. Moreover, the present enzyme can be used to produce physiologically active peptides having a C-terminal α-amide from precursor peptides having glycine at the C-terminal thereof, which precursor peptide may be produced by a recombinant DNA technique, chemical methods, or isolated from a natural source.

EXAMPLES

The present invention will now be further illustrated by, but is no means limited to, the following examples.

Example 1

Amino Acid Composition and Partial Amino Acid Sequence of C-terminal α-Amidating Enzyme (Native Enzyme) Derived From Skin of *Xenopus laevis*

A C-terminal α-amidated enzyme of the skin of *Xenopus laevis* was purified according to a method of Mizuno, K. et al, Biochem. Biophs. Res. Commun. 137, 984–991, 1986. Namely, Frog skins dissected out from *Xenopus laevis* were homogenised with a Polytron homogenizer in 10 mM Tris-HCL buffer (pH 7.0). After centrifugation, the resulting pellets were reextracted with the same buffer and centrifuged. To the combined supernatant solution, solid ammonium sulfate was added to a final concentration of 70% saturation. The resulting precipitate was resuspended in 2 mM sodium phosphate buffer (pH 8.6) and dialyzate against the same buffer. The dialyzate was applied to a column of DEAE-cellulose (DE-52) and eluted with a linear gradient from 2 mM to 250 mM sodium phosphate. The enzyme active fractions were pooled, precipitated with ammonium sulfate and dialyzed. The dialyzate was applied to a column of Affi-Gel Blue (Bio Rad) and eluted with a linear gradient from 0 to 1M NaCl. The major active fractions were pooled and concentrated by ultrafiltration with a YM-10 membrane (Amicon). The concentrate was applied to a column of Sephacryl S-300 and eluted with 0.1M NaCl. The enzyme active fractions were pooled, concentrated with a YM-10 membrane and applied to a hydroxylapatite column and then eluted with a linear gradient from 10 mM to 400 mM potassium phospate. On this hydroxylapatite chromatography, two enzyme activities were separated (designated as AE-I and AE-II). The major active fraction (AE-I) was further purified by high-performance hydroxylapatite (HPHT) chromatograhy. Final purification was carried out by gel-filtration on a column of Seperose 12.

Although this enzyme was designated as AE-1 in the above-mentioned reference, it is designated as a native enzyme in the present invention.

(1) Determination of N-terminal Amino Acid Sequence of Native Enzyme

12 μg of the native enzyme was applied to a Protein Sequencer 470A (Applied Biosystems) for automatic Edman degradation, and as a result, the native enzyme (SEQ ID NO:6) was sequenced at the N-terminal thereof as Ser-Leu-Ser-Asn-Asp-X-Leu-Gly-Thr-Arg-Pro-Val-Met-Ser- (FIG. 5). Note, since X could not be detected as a phenylthiohydration derivative, it was predicted as a Cys residue.

(2) Determination of Amino Acid Sequences of Tryptic Fragments of Native Enzyme

40 μg of the native enzyme was dissolved in 20 μl of 50 mM Tris-HCl(pH 8.0)–2 mM $CaCl_2$, 0.5 μg of trypsin was added to the solution, and the reaction mixture was incubated at 37° C. for 2 hours. Then, 0.5 μg of trypsin was again added to the mixture, which was then incubated at 37° C. for 20 hours to hydrolyze the native enzyme. Next, the reaction mixture was subjected to high performance liquid chromatography (HPLC) using a Chemcosorb 3 ODS-H column (Chemco, 8.0×75 mm), and tryptic fragments produced by the trypsin treatment were eluted by a $CH_3CN$ concentration linear gradient using 0.1% TFA and 0.1% TFA/60% $CH_3CN$ to separate each fragment. Among these fragments, amino acid sequences of 14 tryptic fragments T-4, T-6, T-8, T-11, T-9, T-10, T-18, T-22, T-23, T-24, T-30, T-35, T-39, and T-45 were determined by the same procedure as described for the N-terminal sequencing of the native enzyme (FIG. 5).

(3) Amino acid Composition of Native Enzyme

About 10 μg of the native enzyme was hydrolyzed with 6N hydrochloric acid at 110° C. for 24 hours, and the reaction mixture was analyzed using a Hitachi 835-50 type amino acid analyzer. The results are shown in Table 1.

Example 2

Preoaration of Total RNA From Skin of *Xenopus laevis*

(1) Preparation of Whole RNA

Frog skins (wet weight 2 g) dissected out from *Xenopus leavis* were homogenized with a Polytron homogenizer in 10 ml of PC9 [phenol/chloroform/isoamyl alcohol=24:24:1, saturated with 10 mM Tris-HCL (pH 9.0), 0.1MNaCl and 5 mMEDTA) and 10 mM of NETS solution [100 mM Tris-HCL (pH 9.0), 100 mM NaCl, 10 mM EDTA, 5% SDS]. Next, the homogenate was centrifuged at 3000 rpm for 30 minutes at a room temperature to obtain an aqueous solution, to which the same volume of CIAA (chloroform/isoamyl alcohol=49:1) was added, and the hole was mixed and centrifuged at 3000 rpm for 30 minutes at a room temperature. An aqueous phase was obtained and again treated with CIAA, and to the aqueous solution thus obtained was added two volumes of ethanol, and ethanol precipitation was carried out at −20° C. overnight. After centrifugation at 3000 rpm and 4° C. for 30 minutes, the supernatant was eliminated, and the precipitate was washed with 80% ethanol and dried under a vacuum. The precipitate was then dissolved in 2 ml of 4.2 M guanidine thiocyanate, 0.1 M sodium acetate, 5 mM EDTA (pH 5.0). To a SW40TI centrifugation tube 4 ml of 5 M CsCl, 0.1 M sodium acetate, 5 mM EDTA (pH 5.0) was added, the guanidine thiocyanate solution was overlaid, and the whole was centrifuged at 33,000 rpm and at 25° C. for 15 hours. After centrifugation, an RNA fraction was obtained in the bottom of the tube. The precipitate was washed with 80% ethanol, and dissolved in 500 μl of ETS solution (10 mM Tris-HCl, pH 7.5, 10 mM EDTA and 0.5% SDS). To the solution was added 400 µl of phenol saturated with 0.1 M Tris-HCl, pH 8.0, and after stirring, the whole was centrifuged at 10,000 rpm for 5 minutes. The aqueous phase was obtained, and the same volume of ethyl ether was added to the aqueous phase, and the whole was centrifuged at 3000 rpm for 1 minute to eliminate the ether layer. To the aqueous phase were added 1/10 volume of 2 M sodium acetate (pH 5.0), and two volumes of ethanol, and ethanol precipitation was carried out at −80° C. for 30 minutes. The mixture was centrifuged at 13,000 rpm and 4° C. for 10 minutes, and after eliminating the supernatant, the precipitate was washed with 80% ethanol. The precipitate was dried and dissolved in an appropriate volume of sterilized water. The above-mentioned procedure was repeated, and from 64 g of the skin of *Xenopus laevis*, 16.5 mg of total RNA was prepared.

(2) Preparation of Poly (A) RNA 0.5 g of oligo (dT) cellulose (Cellaborative Research Inc.) was filled in a column, and the column was washed with 10 ml of sterilized water, 10 ml of 0.1 M NaOH/5 mM EDTA, and then with sterile distilled water until a pH value of effluent from the column was lowered to less than 7.0. The column was equilibrated with 10 ml of 1×loading buffer (20 mM Tris-HCl, pH 7.6, 0.5 M NaCl, 1 mM EDTA, 0.1% SDS).

On the other hand, the whole RNA preparation prepared in Example 2.(1) was adjusted to a volume of 3 ml by adding sterilized water to make a whole RNA concentration of 3 µg/ml, and the whole was incubated at 65° C. for 5 minutes, and immediately put into water to cool to a room temperature. To the mixture was added 3 ml of 2×loading buffer (40 mM Tris-HCl, pH 7.6, 1.0 M NaCl, 2 mM EDTA, 0.2% SDS) to make a total volume of 6 ml.

This mixture was applied to the above-prepared oligo (dT) cellulose column. A flow-through fraction was again incubated at 65° C. for 5 minutes, and applied to the column. Then the column was washed with 4 ml of 1×loading buffer and 4 ml of 1×loading buffer (0.1 M NaCl), and poly (A) RNA was eluted with 4 ml of an elution buffer (10 mM Tris-HCl, pH 7.5, 1 mM EDTA, 0.05% SDS). Ethanol precipitation was carried out by adding 1/10 volume of 2 M sodium acetate and 2 volumes of ethanol to the elute fraction to recover poly (A) RNA, and from 9 mg of the total RNA, 74 µg of poly (A) RNA was obtained.

Example 3

Preparation of cDNA Library (1) Preparation of cDNA

Double stranded cDNA was prepared from 7 µg of the poly (A) RNA derived from the skin of *Xenopus laevis*, prepared as described above, using a cONA synthesis system kit (Amersham). To a final reaction mixture from the cDNA synthesis system kit were added 10 µl of 0.25 M EDTA (pH 8.0) and 10 µl of 10% SDS, followed by 120 µl of PC9, and after stirring, the mixture was centrifuged at 10,000 rpm and at a room temperature for 5 minutes to recover an aqueous layer. Ethanol precipitation was carried out by adding 120 µl of 4 M ammonium acetate and 480 µl of ethanol to 120 µl of the aqueous layer, and incubating the whole at −80° C. for 30 minutes. After centrifugation, the resulting ethanol precipitate was washed with 80% ethanol, dried in vacuum, and dissolved in 10 µl of sterilized water. To the solution, were added 2 µl of 10× cacodylate solution (1.4 M sodium cacodylate, 0.3 M Tris-HCl, pH 6.8), 2 µl of 1 mM dCTP, 2 µl of 1 mM DTT and 2 µl of 10 mM $CoCl_2$ as well as 10 units of terminal deoxitransferase (Pharmacia), and the reaction was carried out at 37° C. for 10 minutes. To the reaction mixture, were added 2 µl of 0.25 M EDTA (pH 8.0) and 1 µl of 10% SDS, followed by 23 µl of PC9, and after stirring, the whole was centrifuged at 13,000 rpm for 5 minutes to recover an aqueous layer. A PC9 layer was reextracted with 10 µl of 1×TE (100 mM Tris-HCl, pH 7.5, 1 mM EDTA). Ethanol precipitation was carried out by adding 32 µl of 4 M sodium acetate and 128 µl of ethanol to 32 µl of the above-obtained aqueous layer, and incubating the mixture at −80° C. for 30 minutes. After centrifugation at 13,000 rpm and at 4° C. for 15 minutes, and elimination of the upper layer, 50 µl of 1×TE was added to the ethanol precipitate to dissolve same. Ethanol precipitation was carried out by adding 50 µl of 4 M ammonium acetate and 200 µl of ethanol to the TE solution, and keeping the mixture at −80° C. overnight. After centrifugation at 13,000 rpm and at 4° C. for 15 minutes, the ethanol precipitate was washed with 80% ethanol, and after drying, dissolved in 40 µl of sterilized water. To this solution were added 120 µl of 5×annealing buffer (0.5 M NaCl, 50 mM Tris-HCl, pH 7.5, 1 mM EDTA), 0.6 µg of dG-tailed pBR322 (Bethesda Research Laboratories: dG-tailed pBR322, PstI cut), and 437 µl of sterilized water, and annealing with a pBR322 vector was carried out at 65° C. for 5 minutes, at 44° C. for 2 hours, and then in a water bath overnight.

(2) Transformation of *E. Coli* DH1

A DH1 strain (F⁻, recAl, and Al, gyrA96, thi-1, hsdR17, supE44, relA13, $\lambda^{-1}$) derived from *E. coli* K12 was treated according to the RbCl method (*Saibo Kogaku*, 2, No. 3, p 97, 1983) to prepare competent cells. 20 µl of the annealing mixture prepared as described above was added to 200 µl of the competent cells, and the whole was allowed to stand in ice for 30 minutes, then incubated at 37° C. for 2 minutes, and immediately put into ice. To the transformation mixture was added 800 µl of o medium (Bacto Yeast Extract 5 g, Tryptone 20 g, $MgSO_4$ 5 g in 1 l, pH 7.6), and culturing was carried out at 37° C. for 60 minutes. After culturing, 1 ml of 80% glycerol was added to the culture, which was then frozen at −80° C. to store cultured cells. According to the above-mentioned procedure, an Xenoous laevis skin cDNA library consisting of $7.5 \times 10^5$ clones was prepared.

Example 4

Isolation of cDNA Coding for C-terminal α-amidating Enzyme (1) Preparation of DNA Probe To isolate a cDNA coding for a C-terminal α-amidating enzyme from the cDNA library, mixed DNA probes designated as YS012, YS013, and YS015 corresponding to a partial amino acid sequence of the tryptic fragments $T_{30}$ and $T_{11}$ of the native enzyme were synthesized (see FIG. 6). Next, 1 pmole of each mixed DNA probe was treated with [−³²P] ATP and $T_4$ polynucleotidekinase to introduce [³²P] to 5' hydroxyl of each DNA probe.

(2) Colony Hybridization

The cDNA library stored at −80° C. was thawed, and plated on a nutrient agar plate containing 5 µg/ml tetracycline, and cultured at 37° C. overnight. A nitrocellulose filter (Schleicher & Schuell) was put on the colonies and maintained for 5 minutes. The nitro-cellulose filter was put on a fresh nutrient agar plate containing 5 µg/ml tetracycline in such a manner that the colonies on the filter were upward, and culturing was carried out at 37° C. for 8 hours. Next, this nitrocellulose filter was put on a different fresh nutrient agar plate containing 170 µg/ml chloramphenicol in such a manner that the colonies on the filter were upward, and incubated at 37° C. overnight. Next the nitrocellulose was put on an alkaline denaturation solution (0.1 M NaOH, 1.5 M NaCl)

for 10 minutes, and then on a neutralizing solution (0.5 M Tris-HCl, pH 7.5, 1.5 M NaCl) for 10 minutes. After that, the nitrocellulose was rinsed with 2×SSC solution (20×SSC: NaCl 175.3 g, trisodium citrate 88.2 g in 1 l) and dried in air. The filter was heated at 80° C. for 120 minutes under a reduced pressure, and colony hybridization was carried out according to a method of W.I. Wood, *Pro. Aatl. Acad. Sci. USA*, 82, 1583–1588, 1985. Namely, the nitrocellulose filter was packed in a vinyl sack, and to the sack were added 5 ml of hybridization solution (3×SSC, 50 mM sodium phosphate, pH 6.8, 5×Denhart solution (1×Denhart solution: albumin, polyvinyl pyrrolidone, Ficoll, each 0.2 mg/ml), salmon sperm DNA 0.1 mg/ml), and prehybridization was carried out at 37° C. for 3 hours.

Next, a one million cpm/filter of the above-mentioned mixed DNA probe was added, and hybridization was carried out at 37° C. overnight. The filter was washed twice with 3×SSC at 4° C., and after an addition of a tetramethylammonium chloride solution (3.0 M tetramethylammonium, 50 mM Tris-HCl, pH 8.0, 2 mM EDTA, 0.1% SDS), further washed twice at 37° C. for 30 minutes and twice at 52° C. for 30 minutes. After air-drying, autoradiography was carried out at –80° C. overnight, and as a result, one clone which hybridized with the probe was obtained from the cDNA library consisting of about 400,000 clones.

This clone was designated as *E. coli* DH1/pXA457, and deposited with the Fermentation Research Institute Agency of Industrial Science and Technology (FRI), 1-3, Higashi 1-chome, Tsukuba-shi, Ibaraki-ken 305, Japan, as FERM BP-1367, on May 20, 1987.

Example 5

Analysis of Plasmid pXA457 and Determination of Nucleotide Sequence of cDNA Plasmid pXA457 was isolated and purified from the above-mentioned *E. coli* DH1/pXA457 according to a conventional procedure. The plasmid pXA457 thus is obtained was cleaved with various kinds of restriction enzymes, and a restriction enzyme cleavage map of cDNA which had been inserted into the PstI site of pBR322 was made. This map is shown in FIG. 7(*a*). The cDNA has a size of about 2.7 kb. Next, to determine a nucleotide sequence of the cDNA, various kinds of restriction fragments were cloned into M13 phage, and a dideoxy method of Sanger, F. et al *Pro. Natl. Acad. Sci. USA*, 34, 5463–5467 (1977) was carried out using a Takara DNA sequencing kit. The orientation for sequencing the cDNA is shown in FIG. 7(*b*). A nucleotide sequence of the cDNA in plasmid pXA457 and an amino acid sequence expected from the nucleotide sequence are shown in FIGS. 1- to 1-4.

Example 6

Construction of XA Expression Vector ptrpXAST8 and XA Producing Strain *E. Coli* W3110/ptrpXAST8

A protein coded by nucleotides 112 to 1200 of the cDNA in plasmid pXA457 is designated as "XA", and an XA expression vector ptrpXAST8 and XA producing strain *E. coli* W3110/ptrpXAST8 were constructed as follows.

Figure 8:
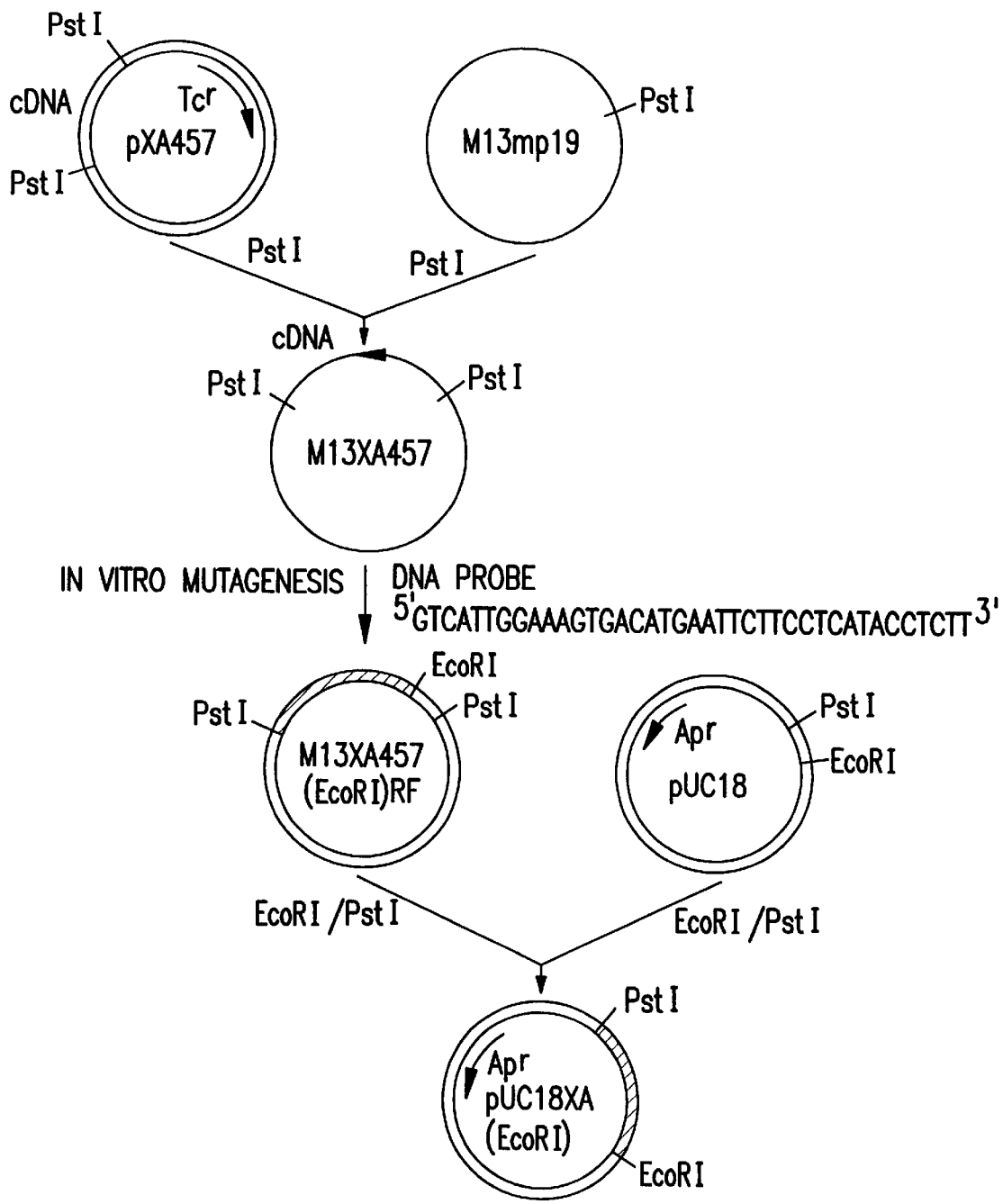
FIG. 8 (SEQ ID NO:59) shows a construction process of a plasmid pUC18XA (EcoRI)

(1) Construction of pUC118XA (EcoRI) (FIG. 8)

A cDNA portion (PstI fragment) of pXA457 was cloned into the PstI site of M13mp19 (Takara Shuzo, Japan) to construct M13XA457. Next, the M13XA457 was subjected to in vitro mutagenesis using a synthetic DNA: 5' GTC ATT GGA AAG TGA CAT GAA TTC TTC CTC ATA CCT CTT 3' according to a method of Morinaga et al, *Biotechnology* 2, 636–639, 1984, to convert a nucleotide sequence; 5' TCT ACC AGA 3' of cDNA (nucleotides 103 to 112) to a nucleotide sequence: 5' GAA TTC ATG 3', resulting in a construction of M13XA457 (EcoRI) wherein a restriction enzyme EcoRI site GAA TTC and a Met codon ATG have been introduced immediately upstream of nucleotides 112 to 114 coding for Ser at the amino acid position 1 in FIG. 1. Next, the M13XA457 (EcoRI) RF (replication form) was cleaved with EcoRI and PstI, and an EcoRI-PstI DNA fragment was cloned into EcoRI-PstI sites of pUC18 (Takara Shuzo, Japan) to construct pUC18XA (EcoRI).

Figure 9:
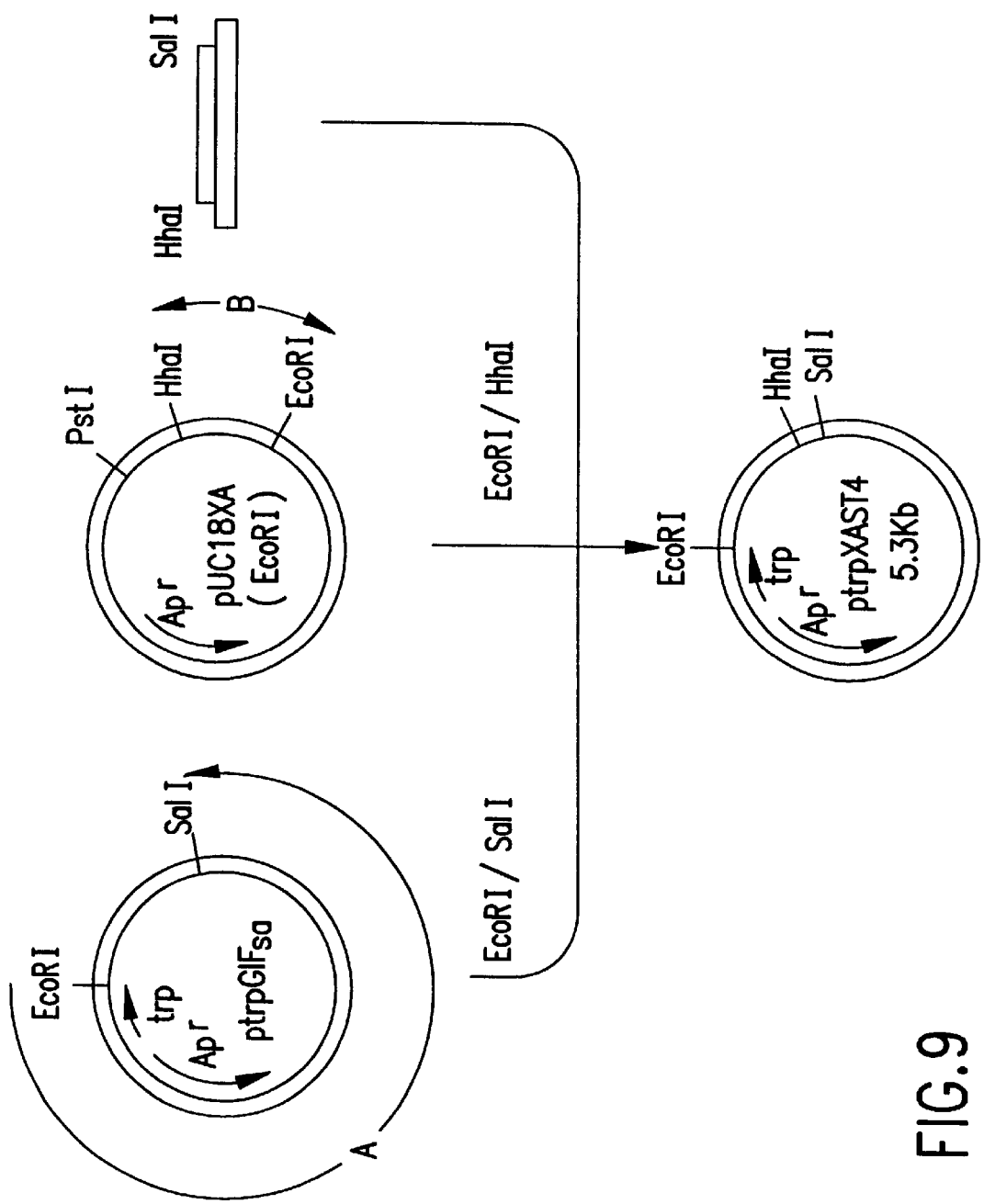
FIG. 9 shows a construction process of a plasmid ptrpX-AST4.

(2) Construction of ptrpXAST4 (FIG. 9)

Plasmid ptrpGIFsα was cleaved with EcoRI and Sal I to obtain a DNA fragment containing a tryptophan operon (fragment A in FIG. 9). Note, *E. coli* WA802/ptrpGIFsα, which contains the plasmid ptrpGIFsα, was deposited with the IRI as FERM P-8503 on Oct. 29, 1985, and transferred to international deposition under the Budapest treaty as FEMM BP-1933 on Jul. 1, 1988.

On the other hand, the plasmid pUC18XA was cleaved with EcoRI and HhaI to obtain an EcoRI-HhaI DNA fragment (fragment B in FIG. 9).

Next, the fragment A, the fragment B, and a synthetic DNA linker:

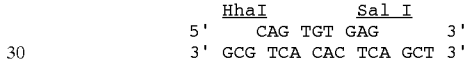

were ligated together to construct a plasmid ptrpXAST4.

(3) Construction of Plasmid ptrpXAST8 and *E. Coli* W3110/ptroXAST8 (FIG. 10)

Figure 10:
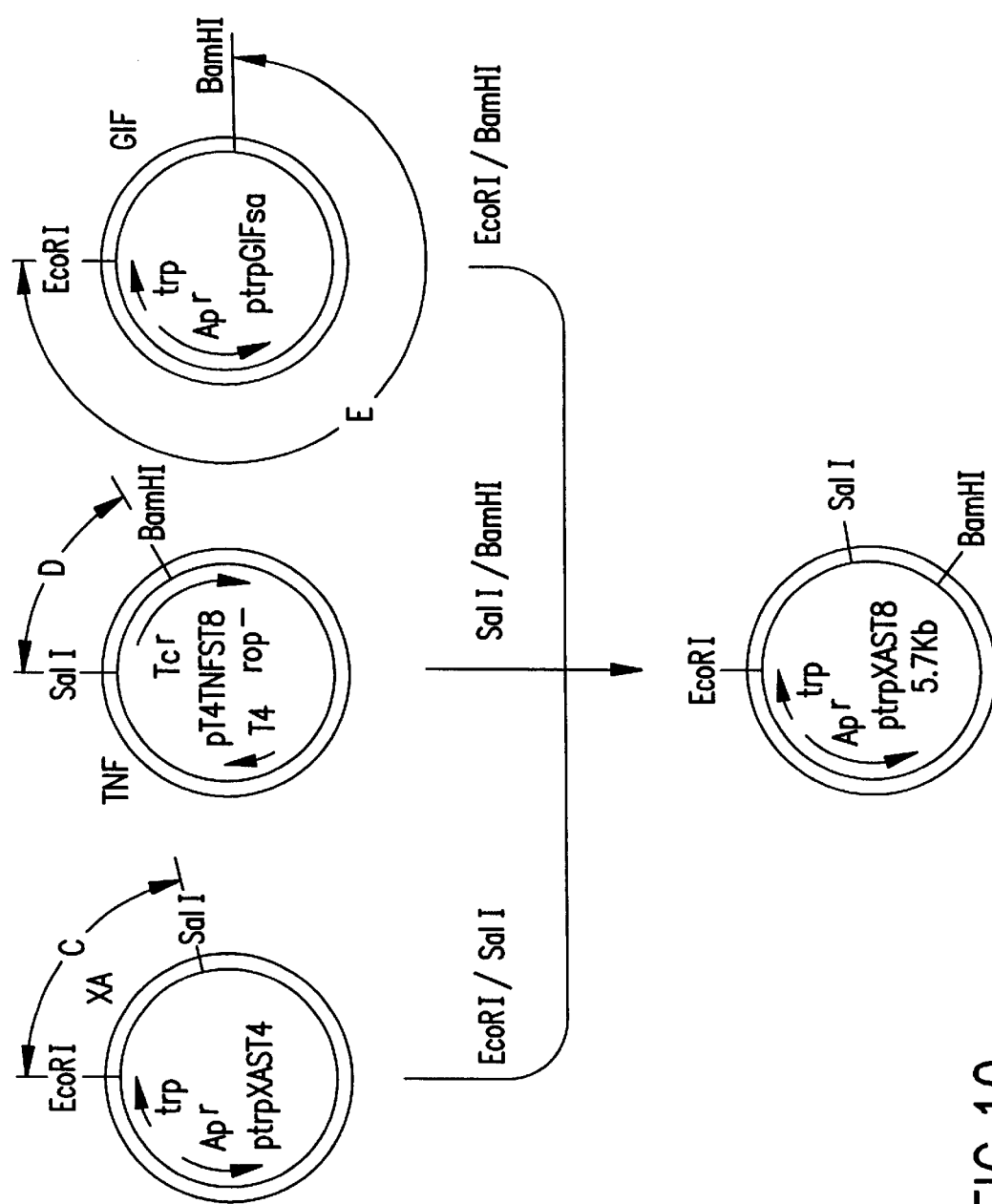
FIG. 10 shows a construction process of a plasmid ptr-pXAST8 for the expression of an enzyme XA.

The above-constructed plasmid ptrpXAST4 was cleaved with EcoRI and Sal I to obtain an EcoRI-Sal I DNA fragment (fragment C in FIG. 10). On the other hand, plasmid pT₄TNFST8rop⁻ was cleaved with Sal I and Bam I to obtain a Sal I-BamHI DNA fragment (fragment D in FIG. 10). Note, pT₄TNFST8rop⁻ was constructed from plasmid pBR322-PL-T4-hTNF according to the process described in Japanese Unexamined Patent Publication (KOKAI) No. 62-077324. The plasmid pBR322-PL-T4-hTNF was deposited with the Deutsche Sammlung von Mikroorganismen Gesellschaft für Biotechnotogische Forschung mbH as DSM 3175. Moreover, ptrpGIFsα was cleaved with EcoRI and BamHI to obtain an EcoRI-BamHI DNA fragment (fragment T in FIG. 10). These fragments C, D and T were ligated using a T₄ DNA ligase and the ligation mixture was used to transform *E. coli* W3110. The transformants were screened to obtain an XA expression vector ptrpXAST8 and an XA producing strain *E. coli* W3100/ ptrpXAST8.

Example 7

Construction of XDA Expression Vector ptrpXDAST8 and XDA Producing Strain *E. Coli* W3110/ptrμXDAST8

A protein coded by nucleotides 112 to 1143 of the cDNA in plasmid pXA457 is designated as "XDA". The XDA expression vector ptrpXDAST8 and XDA producing strain *E. coli* W3110/ptrpXDASTB were constructed as follows.

Figure 11:
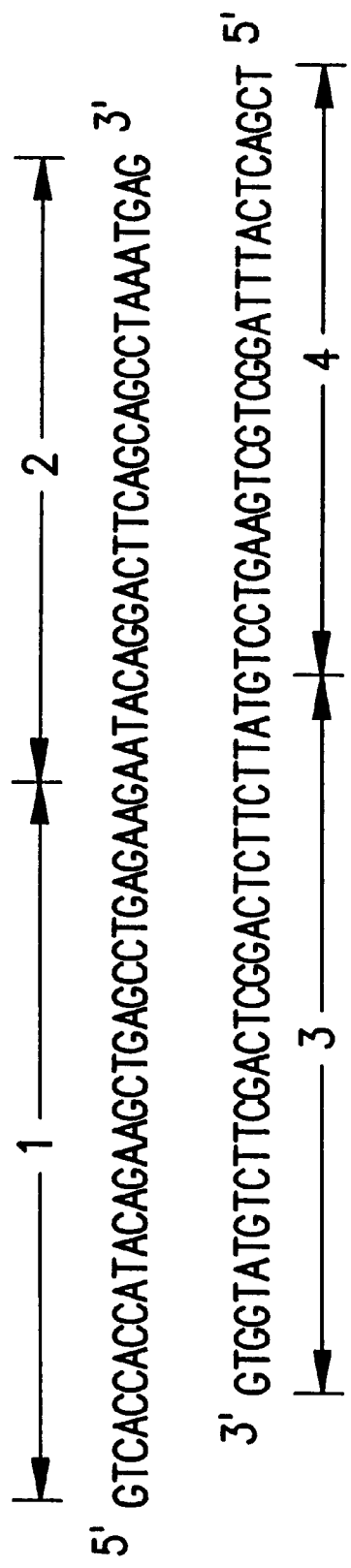
FIG. 11 (SEQ ID NOS:60–61) shows a design of a DNA linker F.

(1) Synthesis of DNA linker (F) (FIG. 11)

To introduce a translation stop codon TGA and a Sal I site immediately downstream of nucleotides 1141 to 1143 coding for Lys in the cDNA, the following four DNA fragments (1) to (4) (SEQ ID NOS:9–12) were synthesized.

(1) 5' GTC ACC ACC ATA CAG AAG CTG AGC CTG AG 3'

(2) 5' AAG AAT ACA GGA CTT CAG CAG CCT AAA TGA G 3'

(3) 5' GTA TTC TTC TCA GGC TCA GCT TCT GTA TGG TG 3'

(4) 5' TCG ACT CAT TTA GGC TGC TGA AGT CCT 3'

Next, the fragments (2) and (3) were phosphorylated at the 5'-ends thereof using ATP and $T_4$ polynucleotide kinase, and the DNA fragments (1) and (4) were added to the phosphorylated DNA fragments (2) and (3). The mixture was treated with $T_4$ DNA ligase to synthesize a double stranded DNA linker (F) wherein DNA fragments (1) and (2), and DNA fragments (3) and (4) were ligated.

Figure 12:
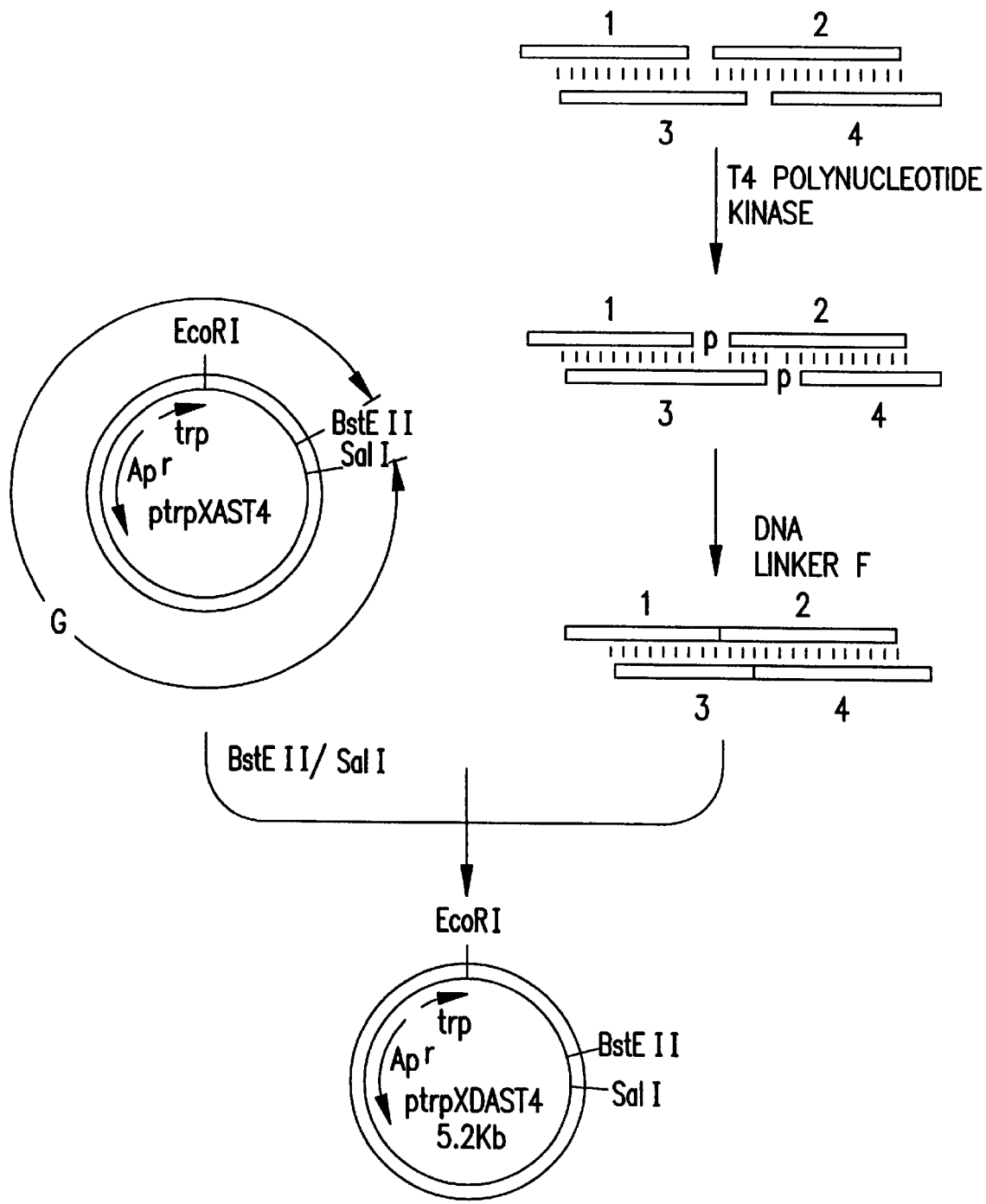
FIG. 12 shows a construction process of a plasmid ptr-pXDAST4.

(2) Construction of ptrpXDAST4 (FIG. 12)

The plasmid XAST4 was cleaved with BstE II and Sal I to obtain a BstE II-Sal I DNA fragment (fragment G in FIG. 12). This DNA fragment G was ligated with the above-synthesized DNA linker F using $T_4$ DNA ligase to obtain the title plasmid ptrpXDAST4.

(3) Construction of ptrpXDST8 and E. Coli W3110/ptrpXDAST8 (FIG. 13)

Figure 13:
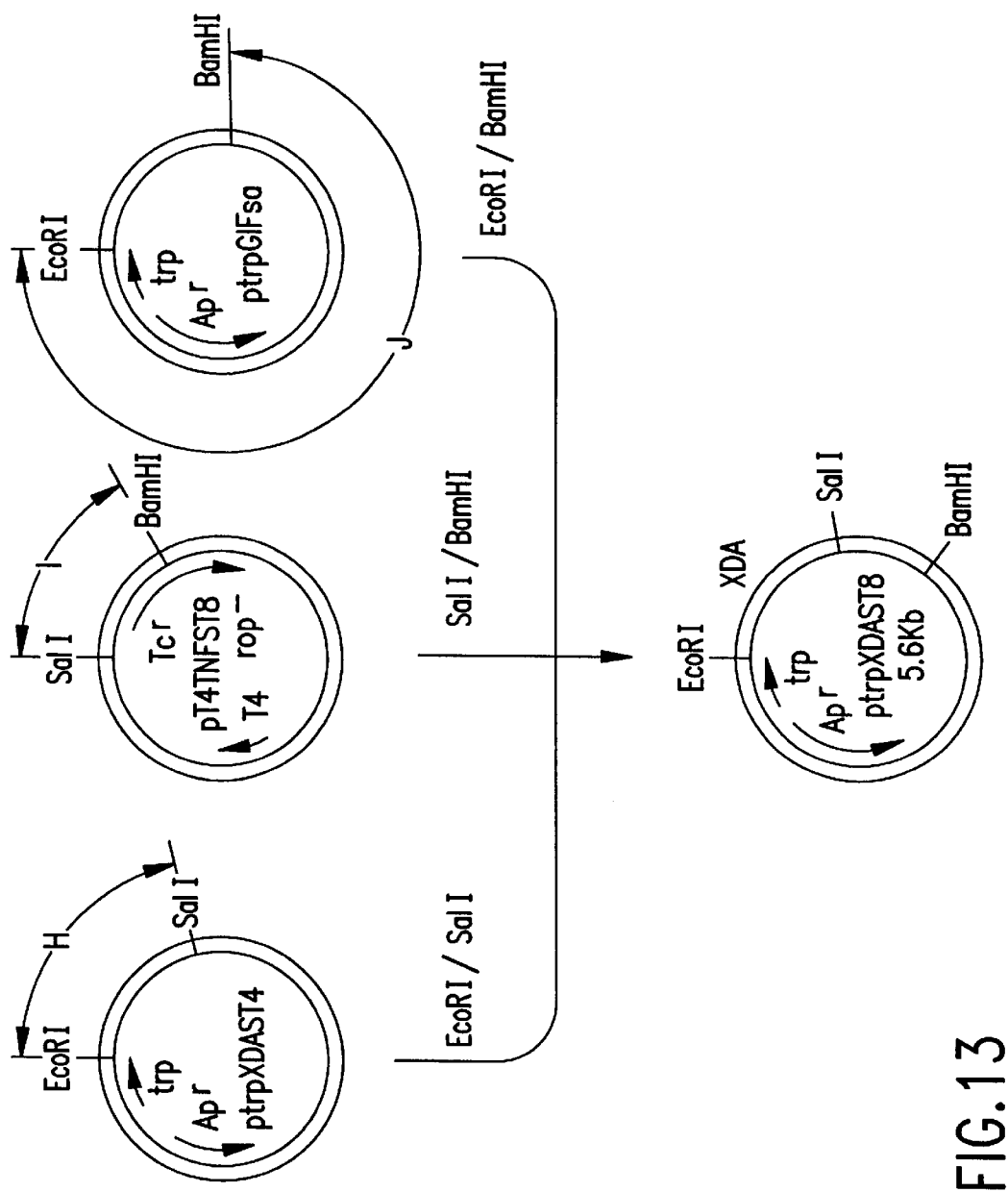
FIG. 13 shows a construction process of a plasmid ptr-pXDAST8 for the expression of an enzyme XDA.

The plasmid ptrpXDAST4 was cleaved with EcoRI and Sal I to obtain an EcoRI-Sal I DNA fragment (fragment H in FIG. 13). Plasmid pT$_4$TNFST8rop$^-$ was cleaved with Sal I and BamHI to obtain Sal I-BamHI DNA fragment (fragment I in FIG. 13), and plasmid ptrpGIFsα was cleaved with EcoRI and BamHI to obtain an EcoRI-BamHI DNA fragment (fragment J in FIG. 13). Next, the fragments H, I, and J thus obtained were ligated with $T_4$DNA ligase, and the ligation mixture was used to transform E. coli W3110. The transformants were screened to obtain an XDA expression vector ptrpXDAST8 and an XDA producing strain E. coli 3110/ptrpXDAST8.

Example 8

Expression of XA and XDA in E. Coli

Figure 14A:
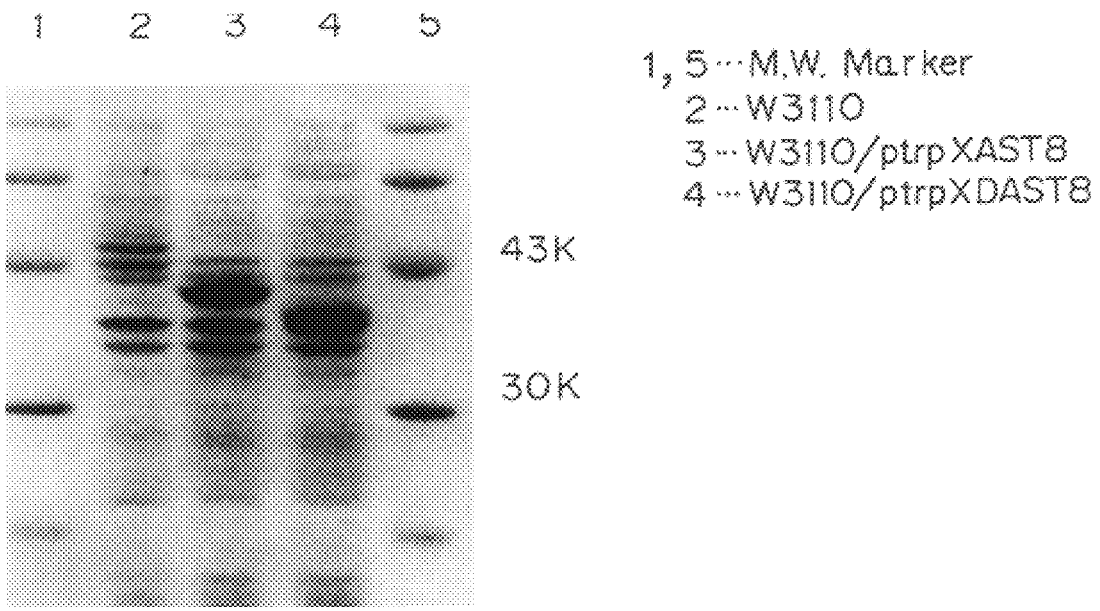
FIGS. 14A and 14B show (14A) a result of an SDS-PAGE for total proteins from *E. coli* W3110, *E. coli* W3110/ptrpXAST8, and *E. coli* W3110/ptrpXDAST8, and (14B) a comparison of the molecular weights of an enzyme XA, an enzyme XDA, and a native enzyme by SDS-PAGE.

The XA producer strain E. coli W3100/ptrpXAST8, and the XDA producer strain E. coli W3100/ptrpXDAST8 were separately cultured in L-broth (polypepton 10 g, sodium chloride 5 g, yeast extract 5 g in 1_water) supplemented with 50 μg/ml ampicillin, overnight. This cultured broth was inoculated to 20 volumes of M9 medium (0.5% sodium monohydrogen phosphate, 0.3% potassium dihydrogen phosphate, 0.5% sodium chloride, 0.1% ammonium chloride) supplemented with 0.2% casamino acid, 5 μg/ml indoleacrylic acid (IAA) and 50 μg/ml ampicillin, and cultured at 37° C. for 7 hours. On the other hand, a control strain E. coli W3110 was cultured in a medium having the same composition as described above except that ampicillin was not contained therein. Next, each culture was centrifuged to collect cells, and the total protein of the cells was determined by SDS-PAGE according to a method of Laemmli, L. K. et al, Nature 227, 680–685, 1970. The results are shown in FIG. 14(a).

E. coli W3110/ptrpXAST8 and E. coli W3110/ptrpXDAST8 produced, in comparison with the control strain E. coli W3110, a specific protein XA having a molecular weight of about 40K and a specific protein XDA having a molecular weight of about 38K, respectively. When cells were suspended in PBS(−) (0.8% sodium chloride, 0.02% potassium chloride, 0.15% sodium monohydrogen phosphate, 0.02% potassium dihydrogen phosphate), disrupted by ultrasonication, and the sonicate was centrifuged at 10,000 rpm for one minutes, a major portion of the protein XA and XDA was transferred to the precipitate.

Example 9

Figure 14B:
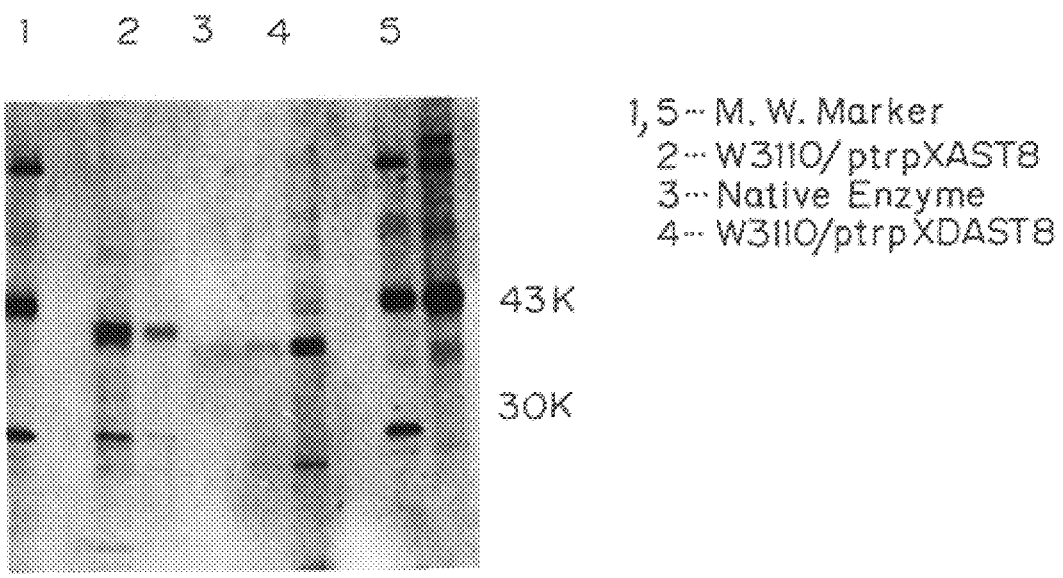

Comparison of Properties of XA, XDA and Native Protein (1) Comparison of Molecular Weight Cells of E. coli W3100/ptrpXAST8 and cells of E. coli W3100/ptrpXDAST8 cultured by the same procedure as described in Example 8 were collected, resuspended in PBS (−), and disrupted by ultrasonication, and the sonicate was centrifuged at 10,000 rpm for one minute to obtain a precipitation fraction. By this procedure, a major portion of XA and XDA was transferred to the precipitation fraction, and many proteins derived from the host E. coli W3110 were transferred to a supernatant. The molecular weights of the XA protein and XDA protein enriched as described above, as well as that of the native enzyme, were compared by SDS-PAGE. The molecular weight of the XDA was exactly the same as that of the native enzyme. The results are shown in FIG. 14(b).

(2) Comoarison of Amino Acid Composition

Each XA and XDA enriched as described above was separated from impurities by SDS-PAGE, a gel piece-containing band corresponding to XA or XDA was excised, and the protein XA or XDA was extracted with TES (10 mM Tris-HCl, pH7.0, 1 mM EDTA, 0.1 M NaCl) from the gel piece. The extract was dried, and dissolved in 0.1% SDS. The solution was then dialyzed in 0.1% SDS overnight. The dialyzate was once dried and redissolved in a small amount of water. Methanol was added to the solution to precipitate XA or XDA, which was then used for amino acid analysis. The amino acid analysis was carried out by hydrolyzing 10 μg of the sample with 6N hydrochloride at 110° C. for 72 hours, and analyzing the hydrolyzate with a Hitachi 853-50 type amino acid analyzer. The results are shown in Table 1.

TABLE 1

| Amino acid | Native Enzyme | XDA | XA |
| --- | --- | --- | --- |
| Trp | ND | ND | ND |
| CySO$_3$H | ND | ND | ND |
| Asp | 32.4 | 32.8 | 34.2 |
| Thr | 24.4 | 21.1 | 21.7 |
| Ser | 22.3 | 19.2 | 19.1 |
| Glu | 27.3 | 27.1 | 31.8 |
| Pro | 32.0 | 28.5 | 28.5 |
| Gly | 27.2 | 31.6 | 32.4 |
| Ala | 20.0 | 20.4 | 21.2 |
| Cys | ND | ND | ND |
| Val | 24.0 | 24.5 | 26.3 |
| Met | 14.9 | 15.0 | 15.1 |
| Ile | 15.7 | 16.0 | 17.0 |
| Leu | 18.2 | 18.0 | 20.6 |
| Tyr | 16.7 | 16.0 | 15.7 |
| Phe | 10 | 10 | 10 |
| Lys | 15.3 | 13.5 | 13.6 |
| His | 13.5 | 14.6 | 14.8 |
| Arg | 14.2 | 13.9 | 14.8 |

ND: not detected

In Table 1, when a comparison is made between the amino acid compositions of the native enzyme, XA and XDA, presuming that the number of phenylalanine residues in the native enzyme, XA and XDA is 10, the numbers of aspartic acid residue, glutamic acid residue, valine residue, isoleucine residue, leucine residue and arginine residue are not different in the native enzyme and the XDA, it appears that the XDA is the same as the native enzyme. Since both the XDA and XA exhibit a C-terminal α-amidated activity, it is considered that the C-terminal region (at least Arp (345) to Val (363) of the protein (prepro-enzyme) translated from the cDNA is not essential for enzyme activity. Accordingly, it is thought that, during biosynthesis of the C-terminal α-amidating enzyme of the skin of *Xenopus laevis*, first a prepro-enzyme consisting of 400 amino acids is expressed, and the prepro-enzyme is cleaved at a peptide bond between Arg (−1)-Ser (+1) to excise N-terminal region and at a peptide bond probably between Lys (344)-Arg (345) to excise the C-terminal region, resulting in the native enzyme.

Example 10

C-terminal α-Amidating Activity of XA and XDA

*E. coli* W3100/ptrpXAST8 and *E. coli* W3100/ptrpXDAST8, and a control strain *E. coli* W3100, were cultured as described above, and 20 ml each of the cultured broth was centrifuged to collect cells, which were then resuspended in 200 ml of PBS(−) and the suspension treated by ultrasonication to disrupt the cells. Next, the disruptant was centrifuged to recover the precipitate, which was then solubilized with 250 μl of 6M guanidine hydrochloride. This solution was successively dialyzed in 200 ml of 4M guanidine hydrochloride containing 10 mM Tris-HCL (pH 7.0) and 50 μm $CuSO_4$ for one hour, in 200 ml of 2M guanidine hydrochloride containing 10 mM Tris-HCL (pH 7.0) and 50 μm $CuSO_4$ for one hour, and then in 200 ml of 10 mM Tris-HCL (pH 7.0) containing 50 μm $CuSO_4$ for one hour. The dialyzate thus obtained was centrifuged to obtain a supernatant, which was then used for an assay of the enzyme activity.

The assay was carried out according to a method of Mizuno et al, *B.B.R.C.* 137, 984–991, 1986, as follows. Namely, 12.5 μl, 25 μl, and 50 μl of the sample prepared as described above were diluted to a total volume of 100 μl by adding distilled water. To the above-prepared solution were added 25 μl of 10 mM N-ethylmaleimide, 25 ml of 10 mM ascorbic acid, 25 μl of 200 μM $CUSO_4$, 1.25 μl of 20 mg/ml catalase, 25 μl of 1% Lubrol, 2 pmoles (170,000 cpm) of [$^{125}I$] -Ac-Tyr-Phe-Gly, and 50 μl of 1M Tris-HCl (pH 7.0), and the mixture was allowed to react at 37° C. for 15 hours. After the reaction, 750 μl of 1M Tris-HCl (pH 7.0) and 2 ml of ethyl acetate were added to the reaction mixture, and the whole was mixed and centrifuged. Next, 1 ml of ethyl acetate layer was removed, and the radioactivity of both the ethyl acetate layer and the residual solution was measured by a γ-counter, and a ratio of radioactivity transferred to the ethyl acetate layer was obtained. Note, it has been confirmed by liquid chromatography and a γ-counter that a C-terminal α-amidated product [$^{125}I$] -Ac-Tyr-Phe-$NH_2$ is specifically transferred to the ethyl acetate layer.

Figure 15:
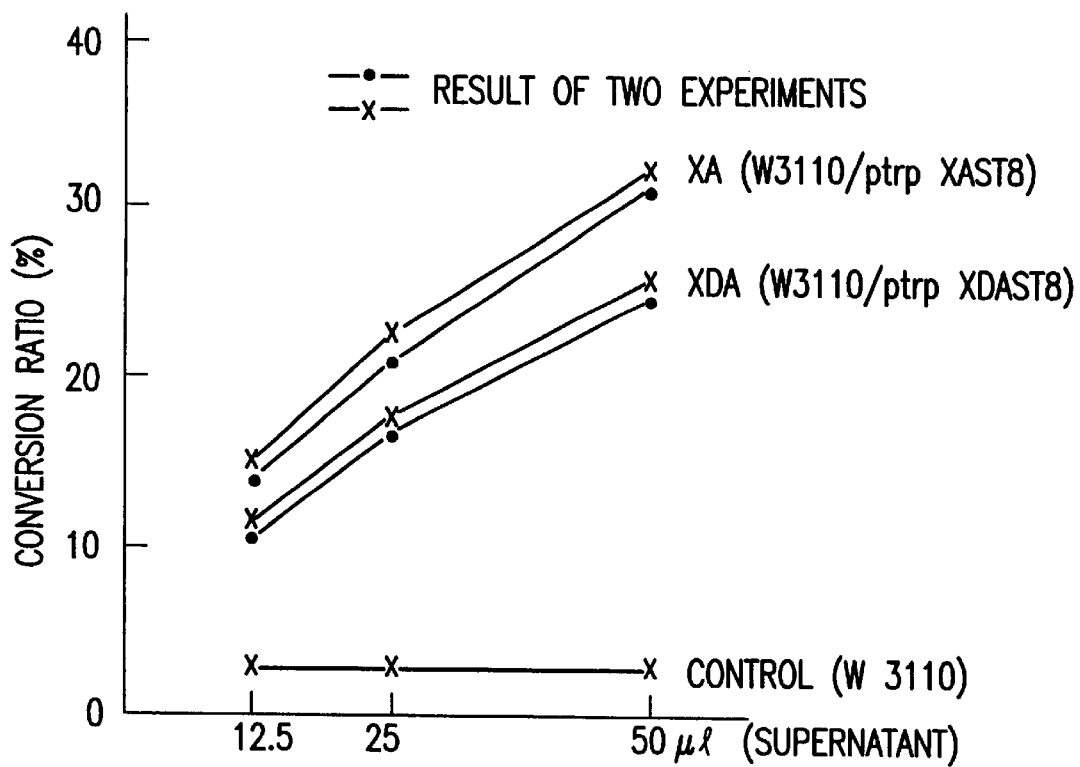
FIG. 15 shows a result of an assay of the enzymes XA and XDA for C-terminal α-amidating enzyme activity.

The results are shown in FIG. 15. Although the product from *E. coli* W3110 did not exhibit an enzyme activity, the activity of the products XA and XDA increased in parallel with an increase of the supernatant added, revealing that a C-terminal α-amidating enzyme was actually produced.

The XA was produced in an amount of 15 mU/ml culture broth, and the XDA was produced in an amount of 11 mU/ml of culture broth.

Example 11

Isolation of cDNA Coding for Different C-terminal α-Amidating Enzyme (2)

(1) Preparation of DNA Probe

To prepare a probe for isolation of a cDNA coding for a different C-terminal α-amidated enzyme from a cDNA library derived from the skin of *Xenopus laevis*, the plasmid pXA457 was completely digested with PvuII to isolate a DNA fragment of about 0.74 kb corresponding to nucleotide 54 to 795 of the cDNA in pXA457, as shown in FIGS. 1-1 to 1-3. The fragment was designated as a PvuII DNA fragment.

Next, the PvuII DNA was radio-labeled with [α-$^{32}P$] CTP by nick-translation.

(2) Colony Hybridization

A cDNA library prepared according to the same procedure as described in Examples 2 and 3, and stored at −80° C., was thawed and plated onto a nutrient agar plate supplemented with 5 μg/ml tetracycline, and cultured at 37° C. overnight. A nitrocellulose filter (Schleicher & Schuell) was placed on the colonies and maintained for 5 minutes. The nitrocellulose filter was placed on a fresh nutrient agar plate containing 5 μg/ml tetracycline in such a manner that the colonies on the filter were upward, and culturing was carried out at 37° C. for 8 hours. Next, this nitrocellulose filter was placed on a different fresh nutrient agar plate containing 170 μg/ml chloramphenicol in such a manner that the colonies on the filter were upward, and incubated at 37° C. overnight. Next the nitrocellulose was placed on an alkaline denaturation solution (0.1 M NaOH, 1.5 M NaCl) for 10 minutes, and then on a neutralizing solution (0.5 M Tris-HCl, pH 7.5, 1.5 M NaCl) for 10 minutes. After that, the nitrocellulose was rinsed with 2×SSC solution (20×SSC: NaCl 175.3 g, trisodium citrate 88.2 g in 1 l) and dried in air. The filter was heated at 80° C. for 120 minutes under a reduced pressure.

Using the nitrocellulose filters thus prepared, colony hybridization was carried out according to the following condition. Namely, two nitrocellulose filters were packed in a vinyl sack, and to the sack were added 5 ml of hybridization solution (3×SSC, 50 mM sodium phosphate, pH 6.8, 5×Denhart solution (1×Denhart solution: albumin, polyvinyl pyrrolidone, Ficoll, each 0.2 mg/ml), salmon sperm DNA 0.1 mg/ml); and prehybridization was carried out at 37° C. for 3 hours.

Next, 560,000 cpm/2 filters of the above-mentioned PvuII DNA probe and 0.5 ml of the above-mentioned prehybridization solution were added, and hybridization was carried out at 37° C. overnight. The filter was washed twice with 3×SSC containing 0.1% SDS at 37° C. for 30 minutes, and further washed twice with 0.1×SSC containing 0.1% SDS at 50° C. for 30 minutes. After air-drying, autoradiography was carried out at −80° C. overnight, and as a result, three clones which hybridized with the PvuII DNA probe were obtained from the cDNA library consisting of about 200,000 clones. These clones were designated as *E. coli* DH1/pXA747, *E. coli* DH1/pXA750, and *E. coli* DH1/pXA799, respectively. Among them *E. coli* DH1/pXA799 was found to contain a cDNA coding for a different C-terminal α-amidating enzyme.

This clone *E. coli* DH1/pXA799 was deposited with the Fermentation Research Institute Agency of Industrial Science and Technology (FRI), 1–3, Higahi 1 chome Tsukubashi Ibaraki-ken 305, Japan, as FERM BP-1586 on Dec. 3, 1987.

Example 12

Analysis of Plasmid pxA747, pXA750 and pXA799 and Determination of Nucleotide Sequence of cDNA in pXA799

Figure 17:
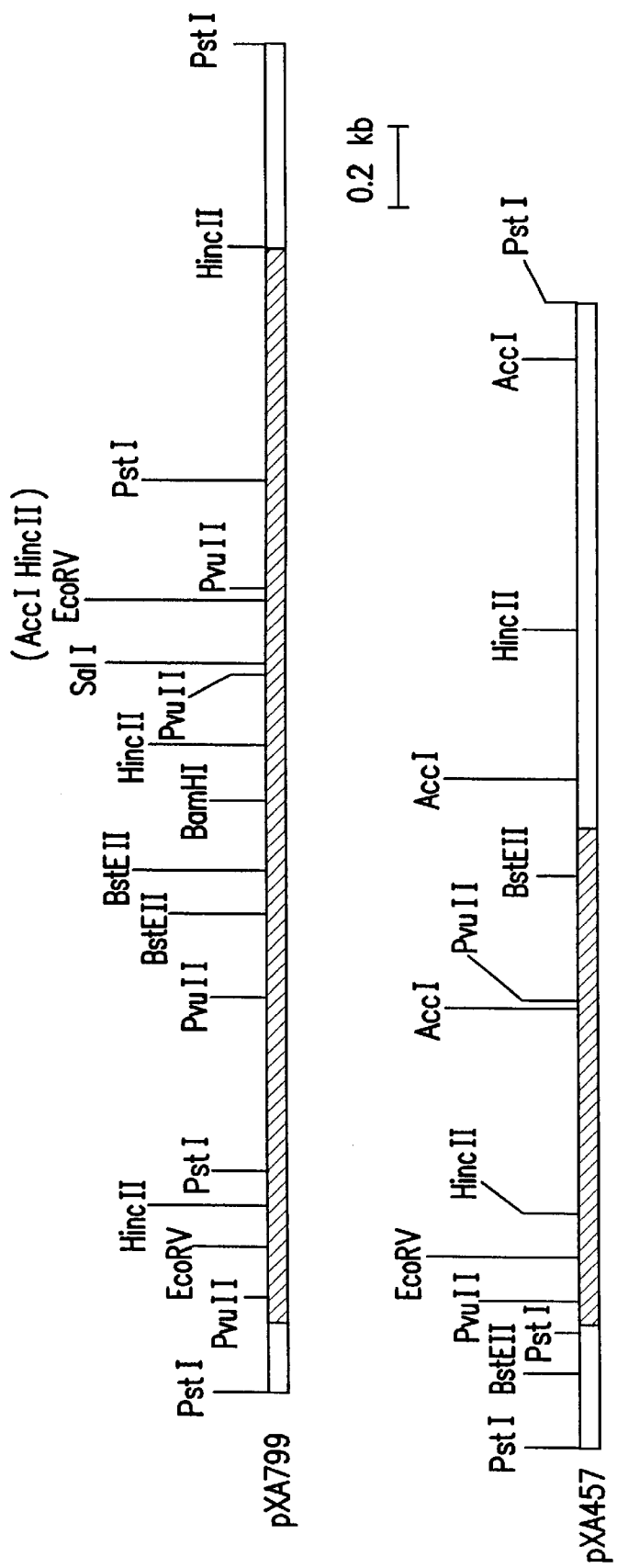
FIG. 17 shows a comparison of restriction enzyme cleavage maps of CDNA in the plasmid pXA457 and cDNA in the plasmid pXA799.

Plasmids pXA747, pXA750, and pXA799 were prepared from *E. coli* DH1/pXA747, *E. coli* DH1/pXA750, and *E.* coli DH1/pXA799, respectively, according to a conventional procedure. These plasmids were cleaved with restriction enzymes PstI, KpmI, HincII, PvuII, AccI, and EroR V, and as a result, since the restriction enzyme cleavage maps of plasmids pXA747 and pXA750 were roughly the same as that of pXA457, they were expected to contain the same cDNA as contained in pXA457. But, to the contrary, pXA799 contained the cDNA of about 3.4 kb, and the restriction enzyme cleavage map of pXA799 was clearly different from that of pXA457 (FIG. 17). This result suggests that the cDNA in pXA799 is different from that in pXA457, and therefore, the cDNA in pXA799 codes for a new type of C-terminal α-amidating enzyme different from the enzyme coded by the cDNA in pXA457.

Figure 18:
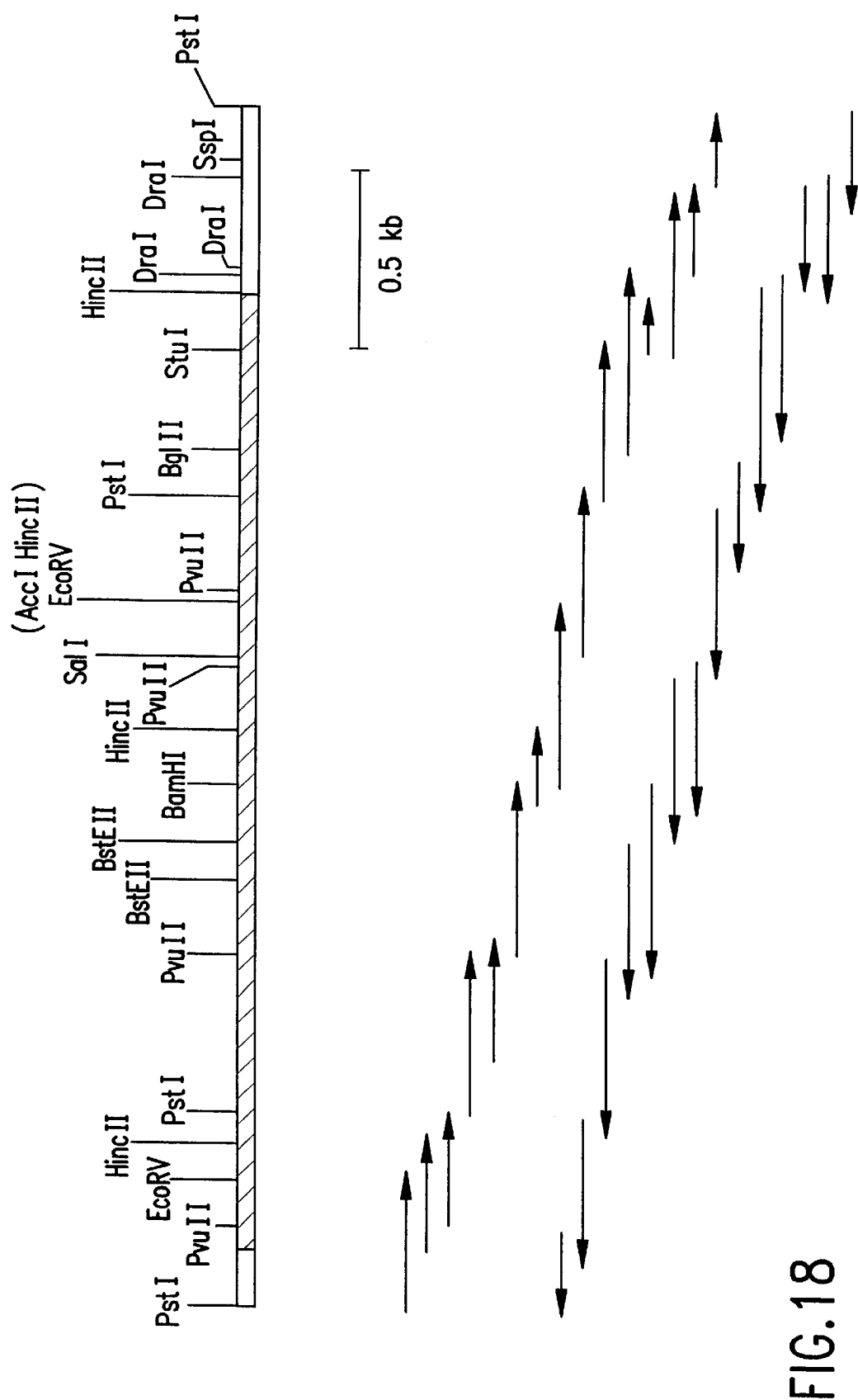
FIG. 18 shows a strategy used to determine a nucleotide sequence of cDNA in the plasmid pXA799.

Accordingly the present inventors determined a nucleotide sequence of cDNA in pXA799 as described below. First, the cDNA in pXA799 was cleaved with various kinds of restriction enzymes, and the generated DNA fragments were subcloned into M13 phage. Next, the nucleotide sequence of each DNA fragment was determined using a Takara DNA sequencing kit (Takara Shuzo, Japan) according to the dideoxy method of Sanger, F. et al, *Proc. Natl. Acad, Sci, USA*, 34, 5463–5467 (1977). The results are shown in FIGS. 16-1 to 16-3. FIG. 18 shows the orientation of a sequencing of DNA fragments used for a determination of nucleotide sequences.

Example 13

Construction of Plasmids and Transformant for Expression of Protein Coded by cDNA in pXA799 and Derivatives Thereof

Figure 21:
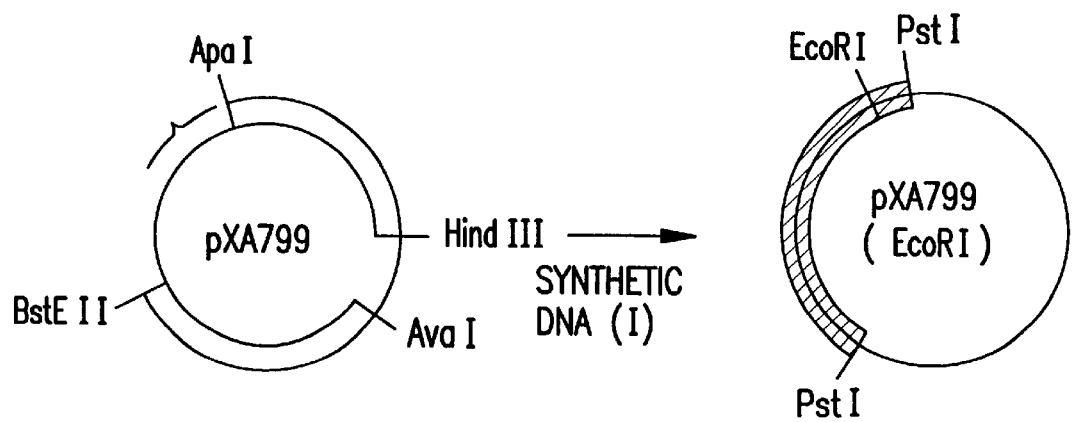
FIG. 21 (SEQ ID NO:69) shows a construction process of a plasmid

(1) Construction of pXA799(EcoRI) (FIG. 21)

Plasmid pXA799(EcoRI) is an expression plasmid which expresses a protein having an amino acid sequence from Ser(1) to Ser(836) is FIGS. 16-1 to 16-3. The plasmid pXA799 was subjected to in vitro mutagenesis using a synthetic DNA: 5' GTC ATT GGA AAG TGA CAT GAA TTC TTC CTC ATA CCT CTT 3' according to a method of Morinaga et al., *Biotechnology* 2, 636–639, 1984, to convert a nucleotide sequence 5' TCA ACC AGA 3' corresponding to nucleotides 109 to 117 in FIG. 16-1 to a nucleotide sequence 5' GAA TTC ATG 3', resulting in a plasmid pXA799 (EcoRI) which contains an EcoRI site (GAA TTC) and a translation start codon coding for Met (ATG) immediately upstream of a codon for Ser (1).

Figure 22:
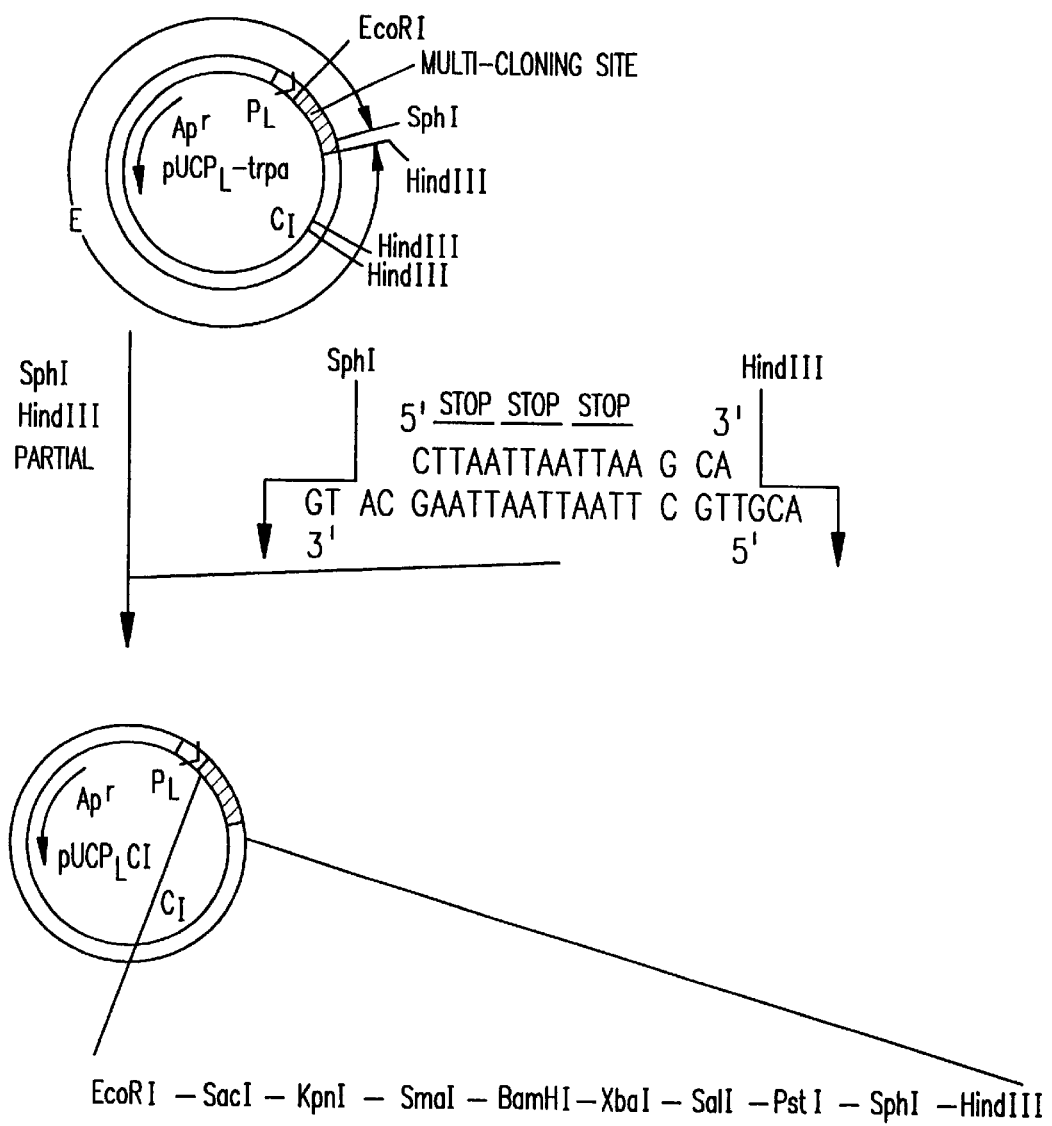
FIG. 22 (SEQ ID NOS:70–71) shows a construction process of a plasmid pUCP$_L$CI.

(2) Construction of pUCP$_L$CI (FIG. 22)

The plasmid pUCP$_L$CI is used to express a gene of interest under the control of a P$_L$ promotor derived from phage. Namely, by inserting a gene of interest having an EcoRI site and a translation start codon ATG at the 5' terminal thereof into an EcoRI site in a polylinker region positioned downstream of a P$_L$ promotor in the plasmid pUCP$_L$CI, the gene can be directly expressed in *E. coli*. Moreover, since the plasmid pUCP$_L$CI contains translation step codons provided by a synthetic DNA linker, a gene of interest having no translation stop codon can be expressed.

Three μg of the plasmid pUC-P$_L$-trpa disclosed in Japanese Patent Application No. 62-166710 was cleaved with 20 units of SphI, and then partially cleaved with 1 unit of HindIII to obtain a SphI-HindIII fragment (fragment E in FIG. 22).

Next, the E fragment was ligated with a synthetic DNA linker (SEQ ID NOS:13 & 14):

```
            stop stop stop
         5'CTTAATTAATTAAGCA3'
         3'GTACGAATTAATTAATTCGTTCGA5'
``` using a T$_4$ DNA ligase, to construct the plasmid pUCP$_L$CI.

Figure 23:
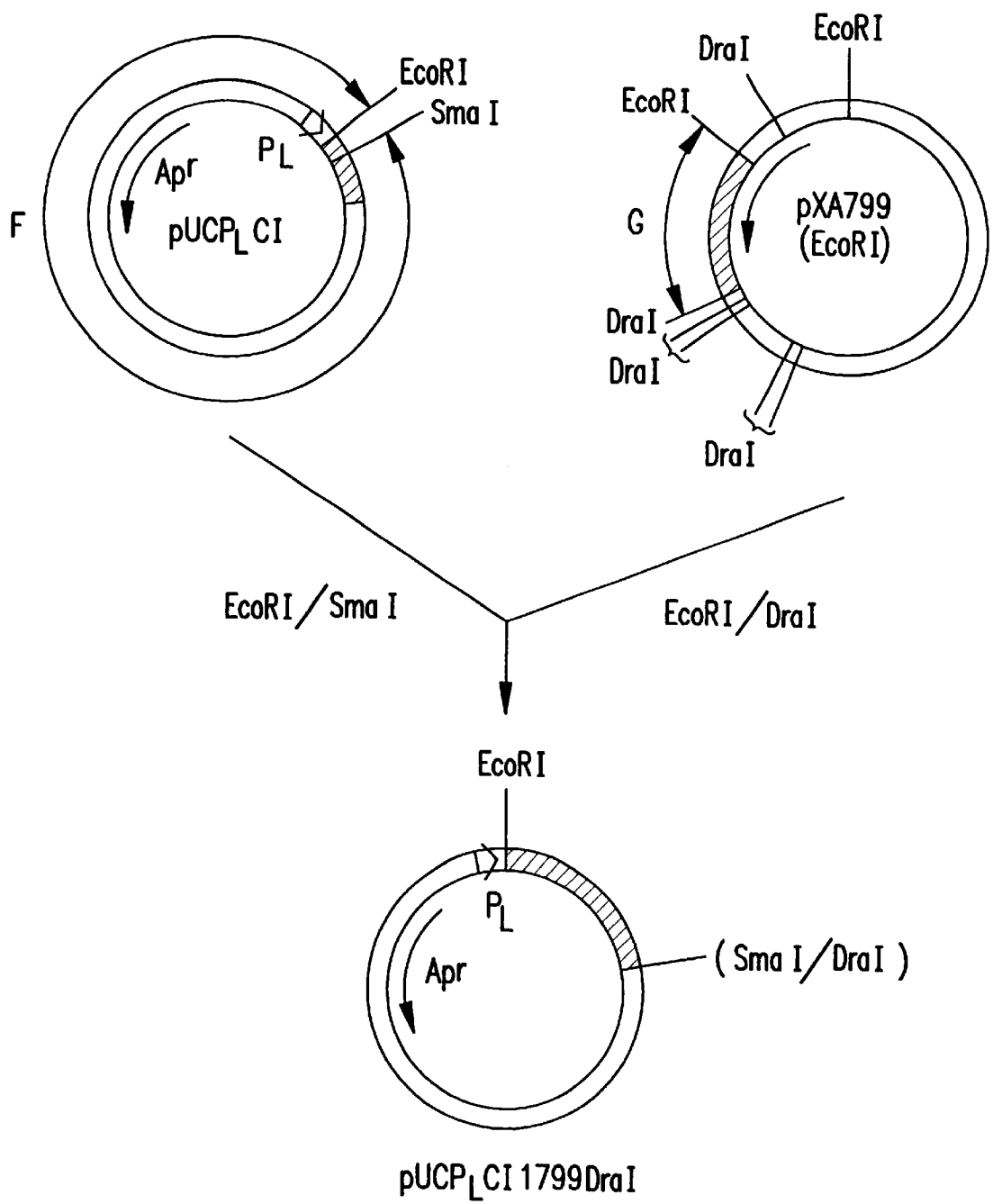
FIG. 23 shows a construction process of a plasmid pUCP$_L$CI799Dra I.

(3) Construction of Plasmid pUCP$_L$CI799Dra I and Transformant *E. Coli* W3110/pUCP$_L$CI799 Dra I (FIG. 23)

The plasmid pUCP$_L$CI799Dra I and transformant *E. coli* W3110/pUCP$_L$CI799Dra I were constructed to express in *E. coli* cells a protein having a primary amino acid sequence of amino acids 1 to 836 in FIGS. 16-1 to 16-3. Three μg of pUCP$_L$CI was cleaved with 20 units of EcoRI and 20 units of SmaI to isolate an EcoRI-SmaI fragment (fragment F in FIG. 23). Next, 3 μg of pXA799 (EcoRI) was cleaved with 20 units of EcoRI and 20 units of Dra I to isolated on EcoRI-Dra I fragment (fragment G in FIG. 23). These fragments F and G were ligated using a T$_4$ DNA ligase, and introduced to *E. coli* W3110 to construct a transformant *E. coli* W3110/pUCP$_L$CI799Dra I, from which a plasmid pUCP$_L$CI799Dra I was isolated.

Figure 24:
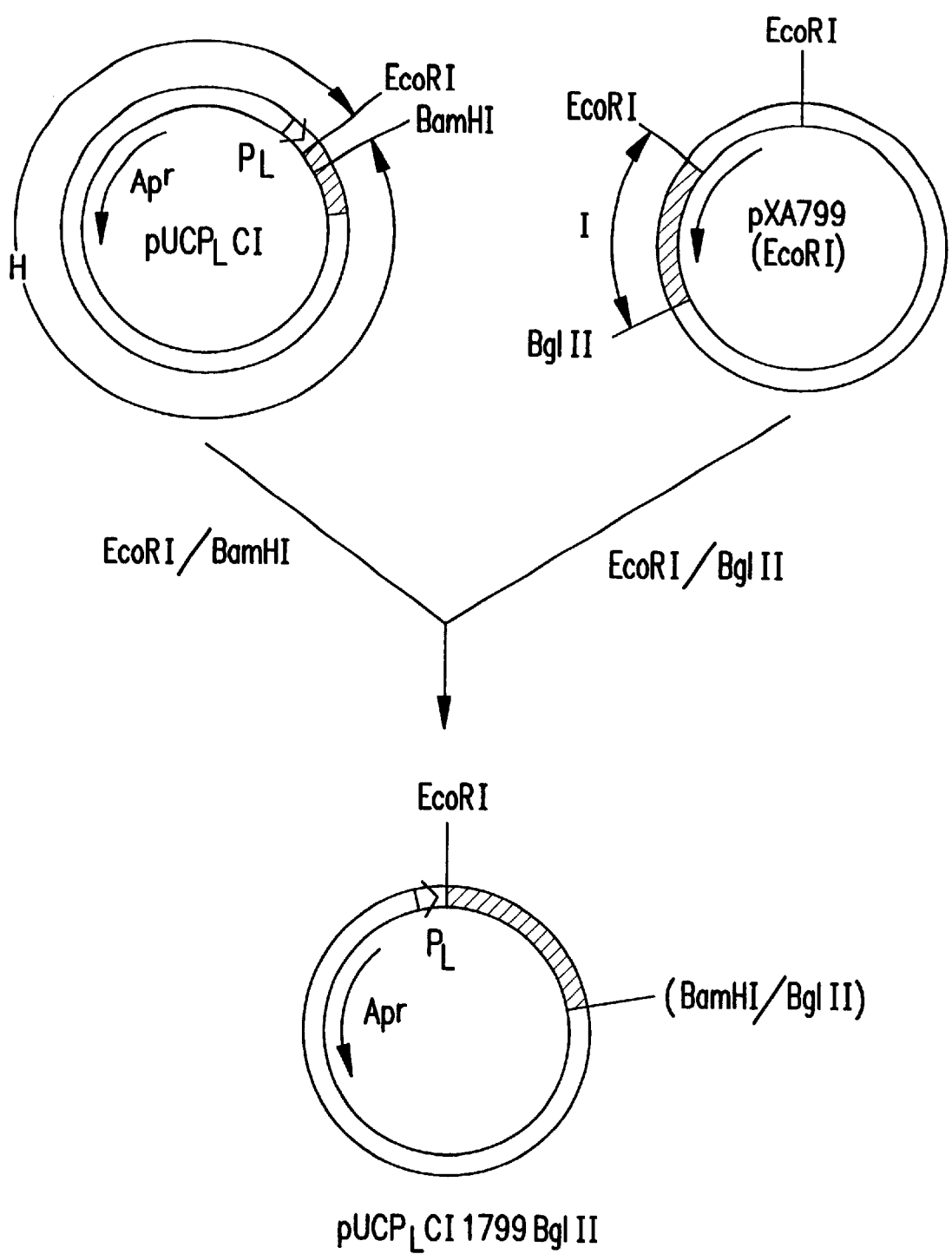
FIG. 24 shows a construction process of a plasmid pUCP$_L$CI799Bgl II.

(4) Construction of Plasmid pUCP$_L$CI799Bgl II and Transformant *E. Coli* W3110/pUCP$_L$CI799 Bgl II (FIG. 24)

A plasmid pUCP$_L$CI799Bgl II and transformant *E. coli* W3110/pUCP$_L$CI799Bgl II were constructed to express in *E. coli* a protein having an amino acid sequence of amino acids 1 to 692 in FIGS. 16-1 to 16-3, and an additional Leu residue at a C-terminal derived from a starting plasmid pUCP$_L$CI. This protein is designated as 799Bgl II. Three μg of pUCP$_L$CI was cleaved with 20 units of EcoRI and 20 units of BamHI to isolate an EcoRI-BramHI fragment (fragment H in FIG. 24). On the other hand, 3 μg of pXA799(EcoRI) was cleaved with 20 units of EcoRI and 20 units of Bgl II to isolate an EcoRI-Bgl II fragment (fragment I in FIG. 24). Next, these fragments H and I were ligated using a T$_4$ DNA ligase and introduced to *E. coli* W3110 to construct a transformant *E. coli* W3110/pUCP$_L$CI799Bgl II, from which a plasmid pUCP$_L$C799Bgl II was isolated.

(5) Construction of Plasmid pUCP$_L$CI799R V and Transformant *E. Coli* W3110/pUCP$_L$CI799R V (FIG. 25)

A plasmid pUCP$_L$CI799R V and transformant *E. coli* W3110/pUCP$_L$CI799R V were constructed to express in *E. coli* a protein having an amino acid sequence of amino acids 1 to 551 in FIGS. 16-1 to 16-2 at the N-terminal side thereof, and an additional (SEQ ID NO:15) Met-Gly-Ile-Leu at the C-terminal thereof derived from a starting plasmid pLCP$_L$CI. This protein is designated as 799R V.

Figure 25:
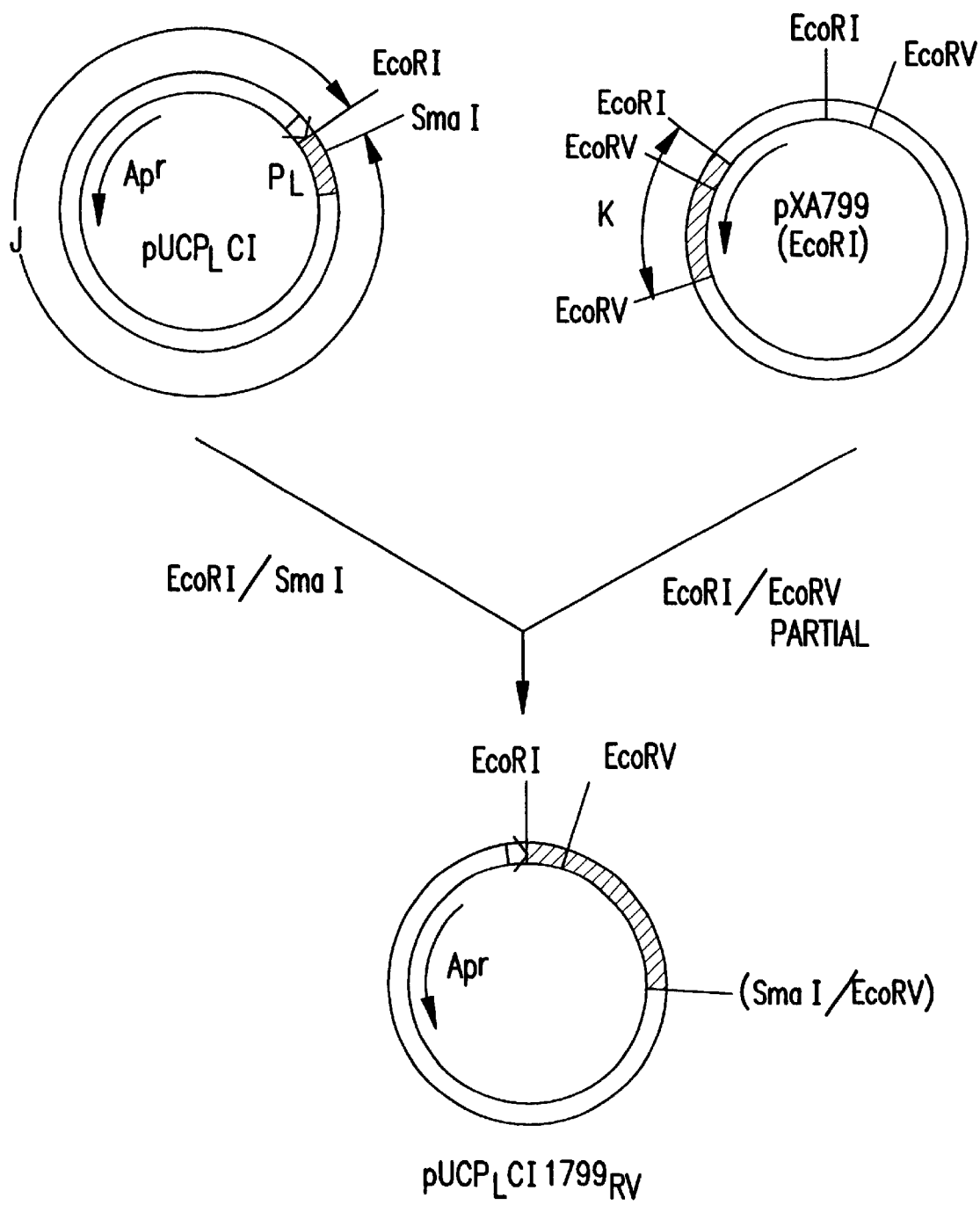
FIG. 25 shows a construction process of a plasmid pUCP$_L$CI799R V.

Three μg of pUCP$_L$CI was cleaved with 20 units of EcoRI and 20 units of Sma I to isolate an EcoRI-Sma I fragment (fragment J in FIG. 25). On the other hand, 3 μg of pXA799 (EcoRI) was cleaved with 20 units of EcoRI and partially cleaved with 1 unit of EcoR V to obtain an EcoRI-EcoR V fragment (fragment K in FIG. 25). Next, these fragments J and K were ligated using a T$_4$ DNA ligase and introduced to *E. coli* W3110 to construct a transformant *E. coli* W3110/pUCP$_L$CI799R V, from which a plasmid pUCP$_L$CI799R V was isolated.

Figure 26:
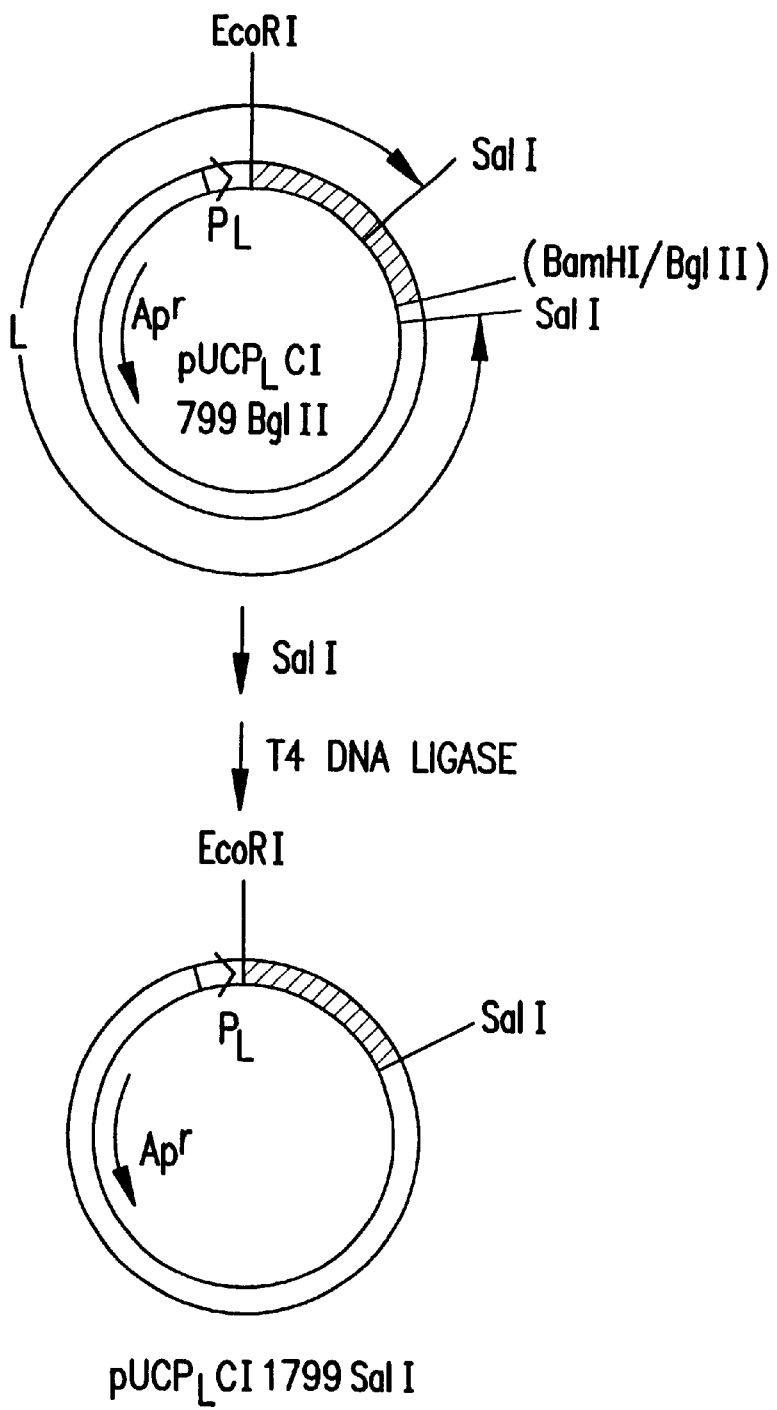
FIG. 26 shows a construction process of a plasmid pUCP$_L$CI799Sal I.

(6) Construction of Plasmid pUCP$_L$CI799Sal I and Transformant *E. Coli* W3110/pUCP$_L$CI799 Sal I (FIG. 26)

A plasmid pUCP$_L$CI799Sal I and transformant *E. coli* W3110/pUCP$_L$CI799 were constructed to express in *E. coli* a protein having a primary amino acid sequence of amino acids 1 to 499 in FIGS. 16-1 to 16-2 at the N-terminal side thereof and an additional (SEQ ID NO:16) Leu-Gln-Ala-Gys-Leu-Ile-Asn at the C-terminal thereof derived from a starting plasmid. This protein is designated as 799Sal I.

Three µg of pUCP$_L$CI799Bgl II was cleaved with 20 units of Sal I to isolate a larger DNA fragment (fragment L in FIG. 26), which was then intramolecularly ligated using T$_4$ DNA ligase and introduced to *E. coli* W3100 to construct a transformant *E. coli* W3100/pUCP$_L$CI799Sal I, from which a plasmid pUCP$_L$CI799Sal I was isolated.

(7) Construction of Plasmid pUC$_L$CI799Bst II$^L$ and Transformant *E. Coli* W3110/pUC$_L$CI799BstE II$^L$ (FIG. 27)

A plasmid pUCP$_L$CI799BstE II$^L$ and transformant *E. coli* W3110/pUCP$_L$CI799BstE II$^L$ were constructed to express in *E. coli* a protein having a primary amino acid sequence of amino acids 1 to 329 in FIGS. 16-1 to 16-2 a the N-terminal side thereof and an additional (SEQ ID NO:17) Gly-Asp-Pro-Leu-Glu-Ser-Thr-Cys-Arg-His-Ala derived from a starting plasmid pUCP$_L$CI at the C-terminal thereof. This protein is designated as 799BstE II$^L$.

Figure 27:
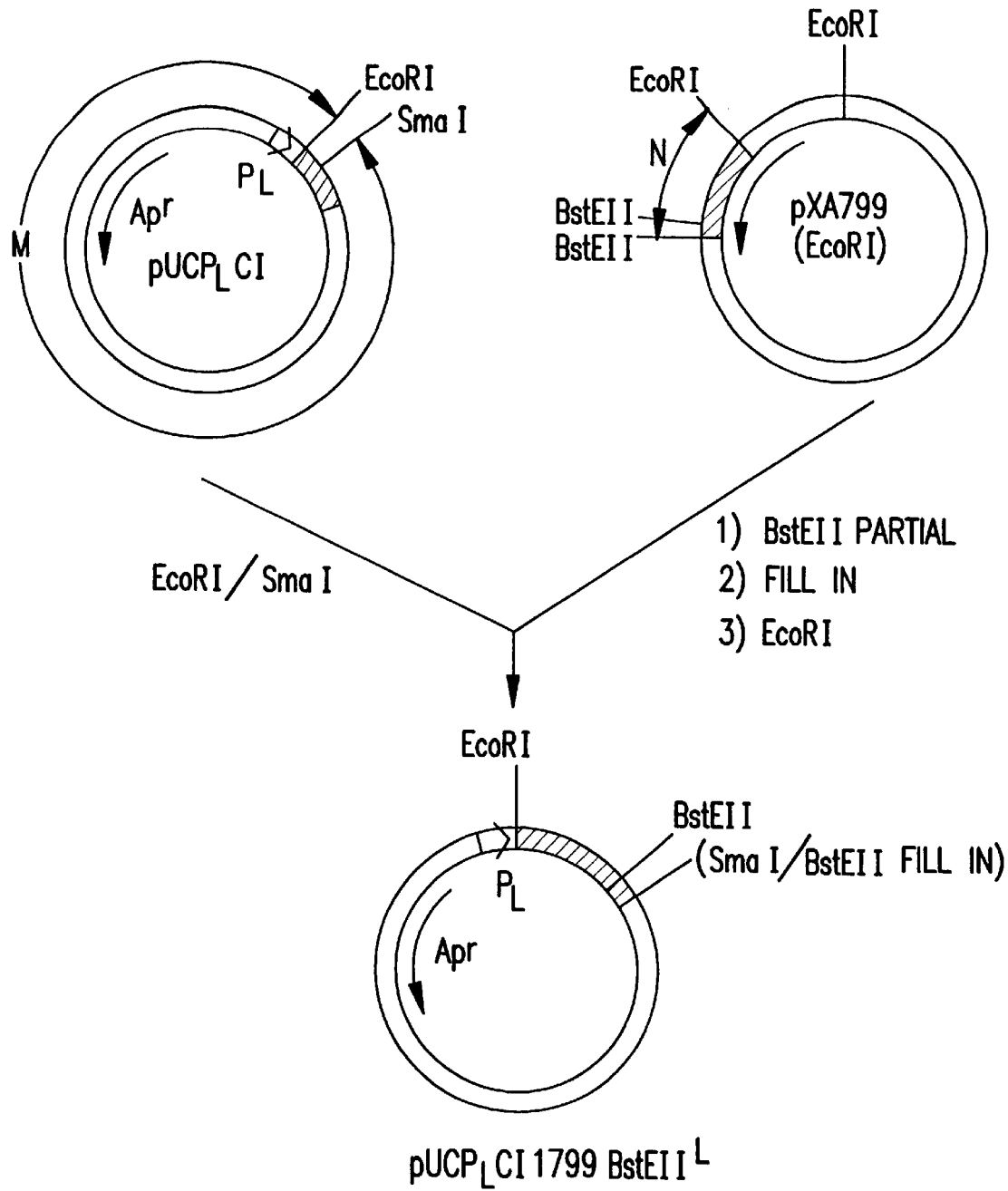
FIG. 27 shows a construction process of a plasmid pUCP$_L$CI799BstE II$^L$.

Three µg of pUCP$_L$CI was cleaved with 20 units of EcoRI and 20 units of SmaI to isolate an EcoRI-SmaI fragment (fragment M in FIG. 27). On the other hand, 3 µg of pXA799(EcoRI) was partially cleaved with 1 unit of BstE II, and after a fill-in of resulting cohesive ends using a T$_4$ DNA polymerase and dNTP, again cleaved with 20 units of EcoRI to isolate an EcoRI-BstE II$^L$ fragment (fragment N in FIG. 27). Next, these fragments M and N were ligated using a T$_4$ DNA ligase and introduced to *E. coli* W3110 to construct a transformant *E. coli* W3100/pUCP$_L$CI799BstE II$^L$, from which a plasmid pUCP$_L$CI799BstE II$^L$ was isolated.

(8) Construction of Plasmid pUCP$_L$CI799BstE II$^S$ and Transformant *E. Coli* W3100/pUCP$_L$CI799BstE II$^S$ A plasmid pUCP$_L$CI799BstE II$^S$ and transformant *E. coli* W3100/pUCP$_L$CI799BstE II$^S$ were constructed to express in *E. coli* a protein having a primary amino acid sequence of amino acids 1 to 298 in FIG. 16-1 at the N-terminal side thereof and an additional (SEQ ID NO:18) Glyy-Asp-Pro-Leu-Glu-Ser-Thr-Cys-Arg-His-Ala derived from a starting plasmid pUCP$_L$CI at the C-terminal thereof. This protein is designated as 799BstE II$^S$.

Figure 28:
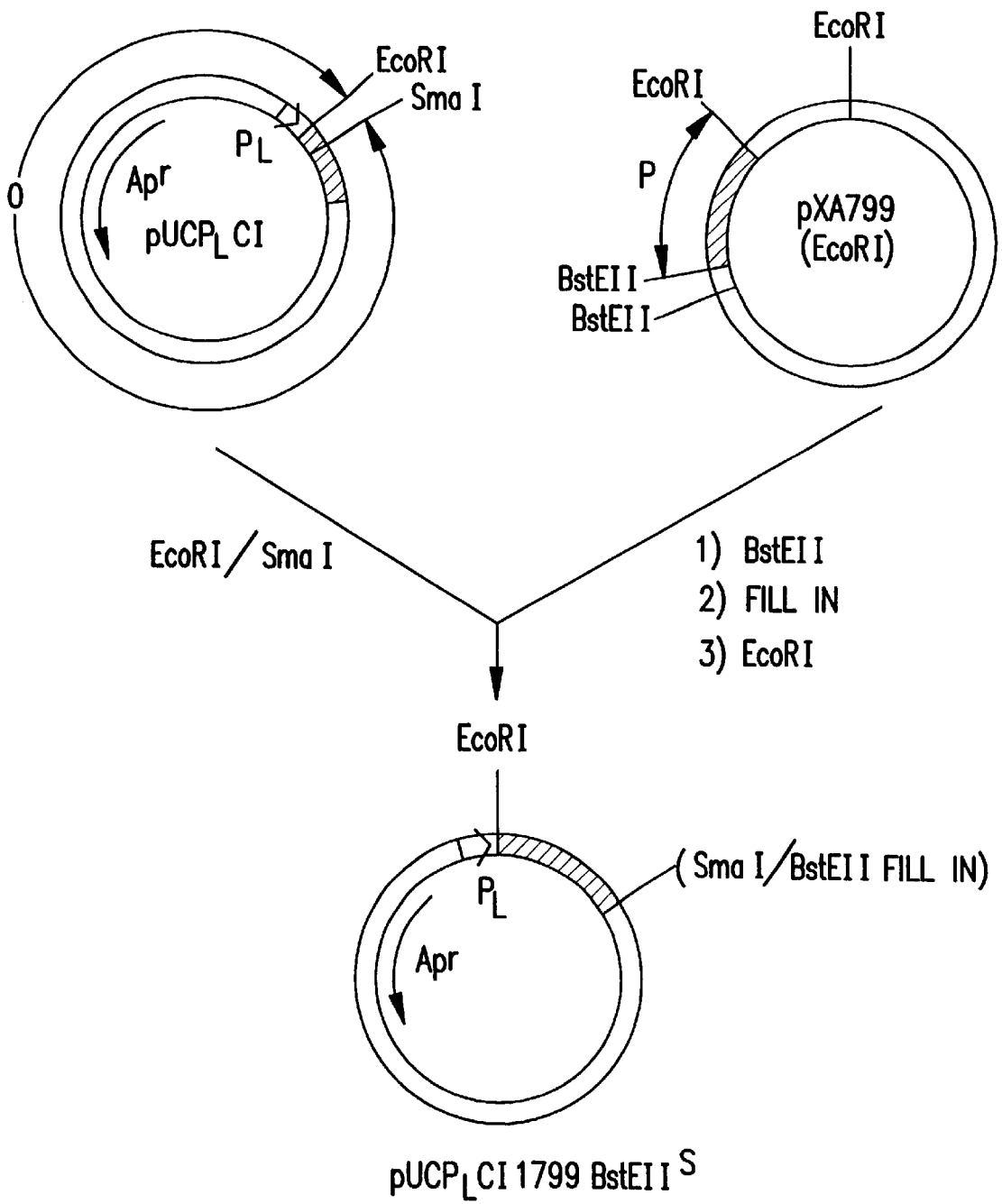
FIG. 28 shows a construction process of a plasmid pUCP$_L$CI799BstE II$^S$.

Three µg of pUCP$_L$CI was cleaved with 20 units of EcoRI and 20 units of SmaI to isolate an EcoRI-SmaI fragment (fragment 0 in FIG. 28). On the other hand, 3 µg of pXA799 (EcoRI) was partially cleaved with 20 units of BstE II, and after a fill-in of resulting cohesive ends using T$_4$ DNA polymerase and dNTP, again cleaved with 20 units of EcoRI to isolate an EcoRI-BstE II$^S$ fragment (fragment P in FIG. 28). Next, these fragments O and P were ligated using a T$_4$ DNA ligase and introduce to *E. coli* W3110 to construct a transformant *E. coli* pUCP$_L$CI799BstE II$^S$, from which a plasmid pUCP$_L$CI799BstE II$^S$ was isolated.

Figure 29:
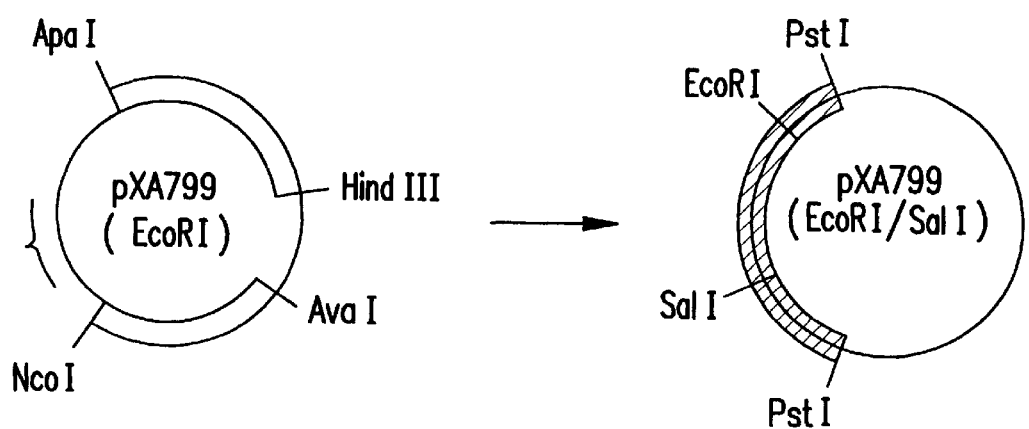
FIG. 29 shows a construction process of a plasmid pXA799(EcoRI-Sal I)

(9) Construction of Plasmid pXA799 (EcoRI-Sal I (FIG. 29)

A plasmid pXA799 (EcoRI-Sal I) was constructed to express in *E. coli* a protein having an amino acid sequence of amino acids 1 to 346 in FIGS. 16-1 to 16-2.

The plasmid pXA799 (EcoRI) was subjected to in vitro mutagenesis using a synthetic DNA (SEQ ID NO:19): 5' CAG CAG CCT AAA TAG GTC GAC GAA GAA GTA TTA AAT 3' to convert a nucleotide sequence 5' CGG GAG GAG 3' corresponding to nucleotides 1156 to 1164 of the cDNA in pXA799 shown in FIG. 16 to a nucleotide sequence 5' TAG GTC GAC 3', resulting in the construction of a plasmid pXA799(EcoRI-Sal I) wherein a translation stop codon TAG and a restriction enzyme Sal I site (GTC GAC) were introduced immediately downstream of the Lys coded by nucleotide 1153 to 1155 of the cDNA.

Figure 30:
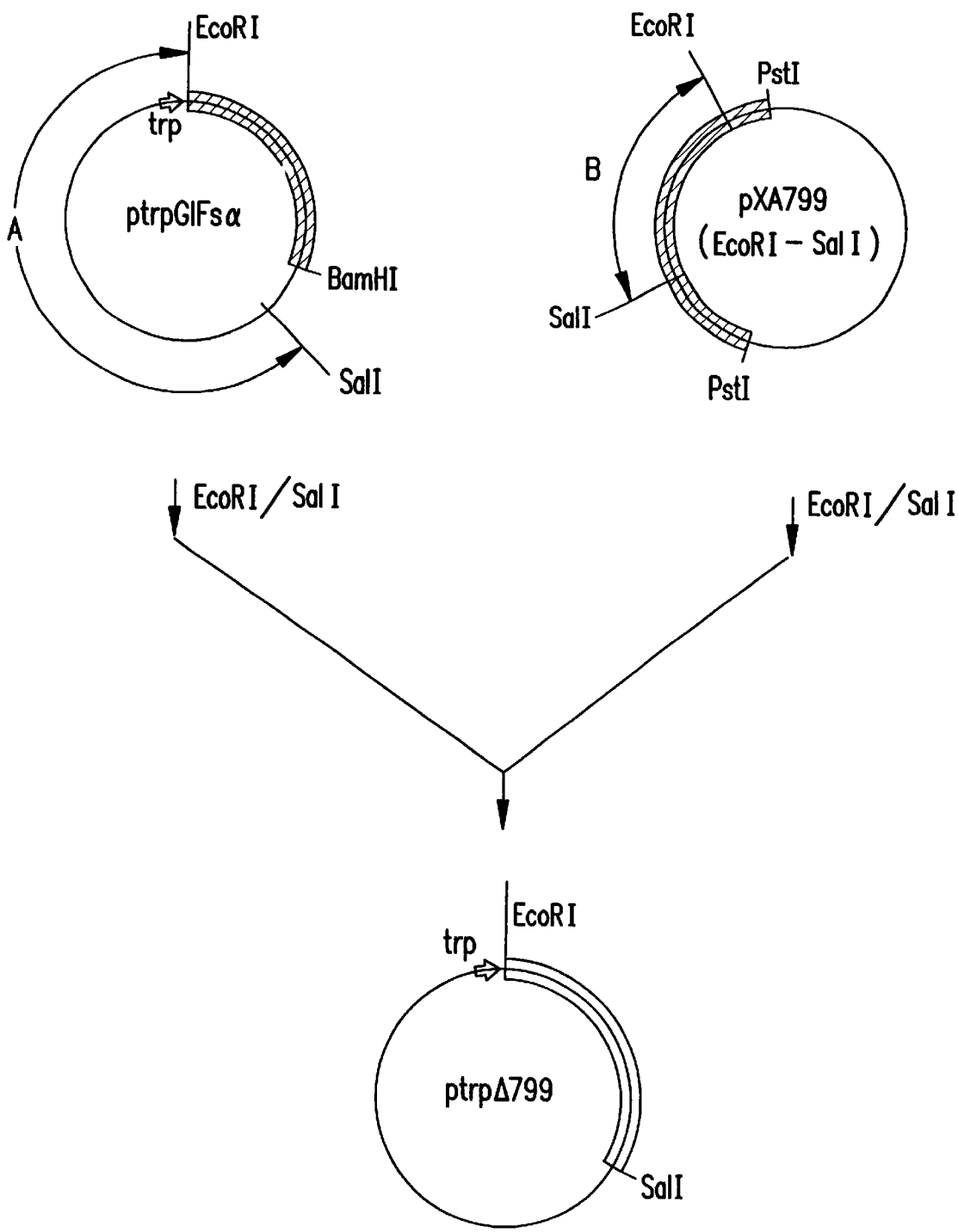
FIG. 30 shows a construction process of a plasmid ptrpΔ799.

(10) Construction of Plasmid ptrp 799 and Transformant *E. coli* W3110/ptrp 799 (FIG. 30)

A plasmid ptrp 799 and transformant *E. coli* W3110/ptrpΔ799 were constructed to express, under the control of a tryptophan promoter, in *E. coli* a protein having a primary amino acid sequence of amino acids 1 to 346 in FIGS. 16-1 to 16-2.

The plasmid ptrpGIFsα described in Example 6(2), which was designed to express a chimera protein of human interferon and α-neo-endorfin under the control of a tryptophan operon, was cleaved with EcoRI and Sal I to isolate a DNA fragment containing tryptophan operon (fragment A in FIG. 30). On the other hand, the pXA799 (EcoRI-Sal I) was cleaved with EcoRI and Sal I to isolate an EcoRI-Sal I DNA fragment (fragment B in FIG. 30). Next, these fragments A and B were ligated using a T$_4$ DNA ligase and introduced to *E. coli* W3110 to construct a transformant *E. coli* W3110/ptrpΔ799, from which a plasmid ptrp 799 was isolated.

(11) Construction of Plasmid ptrp799-457 and Transformant *E. Coli* W3110/ptrp799-457Δ (FIG. 31)

A plasmid ptrp799-457Δ and transformant *E. coli* W3110/ptrp799-457Δ were constructed to express in *E. coli* a protein having a primary amino acid sequence consisting of amino acids 1 to 329 coded by cDNA in pXA799 at the N-terminal thereof and amino acids 364 to 381 coded by the cDNA in pXA457. This protein is designated as 799-457Δ.

Figure 31:
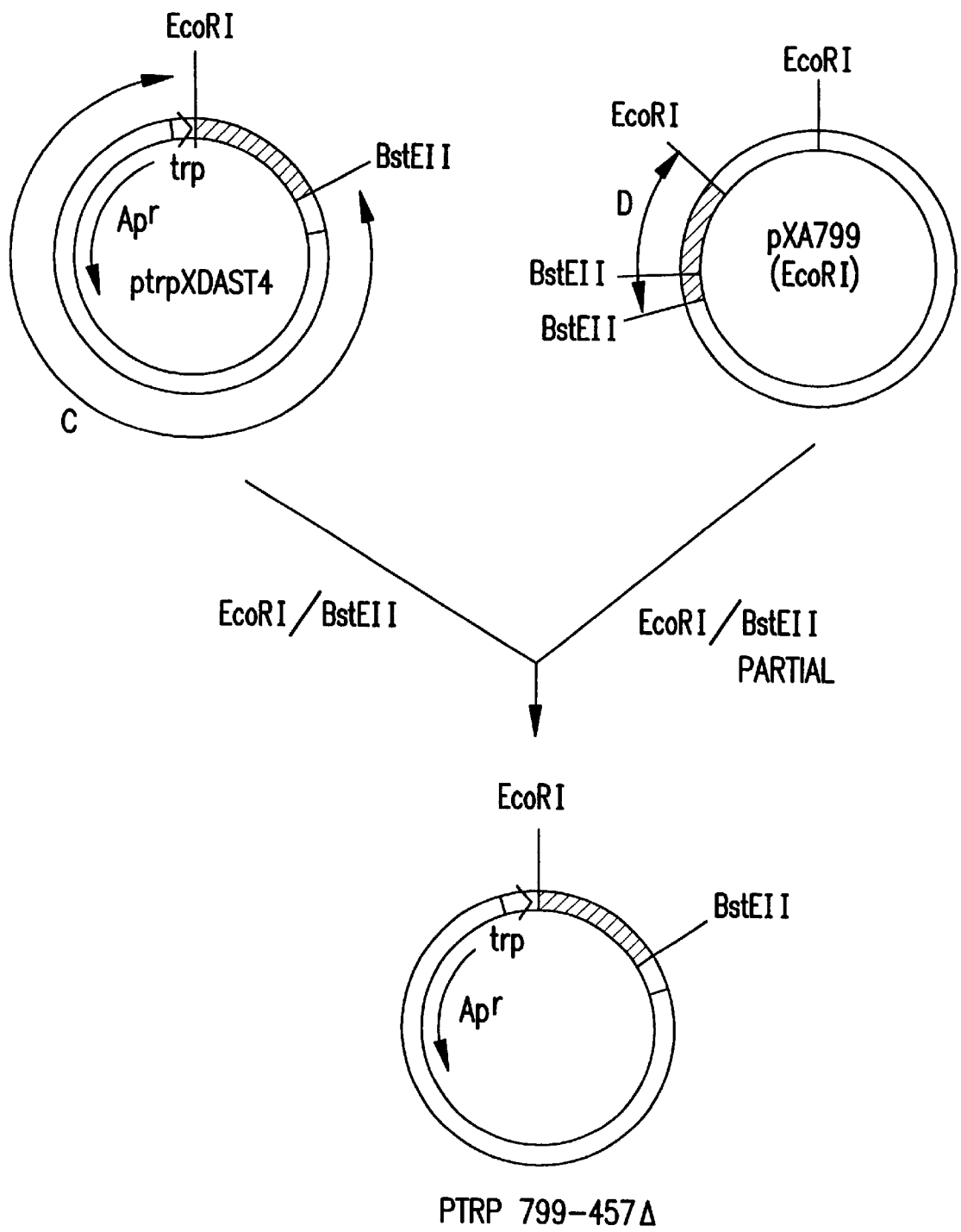
FIG. 31 shows a construction process of a plasmid ptrp799–459Δ

Three µg of ptrpXDAST4 was cleaved with 20 units of EcoRI and 20 units of BstE II to isolate an EcoRI-BstE II fragment (fragment C in FIG. 31). On the other hand, pXA799(EcoRI) was cleaved with 20 units of EcoRI and then partially cleaved with 1 unit of BstE II to isolate an EcoRI-BstE II fragment (fragment D in FIG. 31). Next, these fragments C and D were ligated using a T$_4$ DNA ligase and introduced to *E. coli* W3110 to construct a transformant *E. coli* W3110/ptrp799-457Δ, from which a plasmid ptrp799-457Δ, from which a plasmid ptrp799-457Δ was isolated.

Example 14

Expression of Protein Coded by cDNA Derived From µXA799 and Derivative Thereof

Various kinds of *E. coli* transformants prepared as described in Example 13 were separately cultured to express coded proteins according to the following procedures.

(1) Expression of 799Dra I in *E. Coli*

*E. coli* W3110/pUCP$_L$CI799Dra I was cultured in a super broth (prepared by diluting 24 g of yeast extract, 12 g of trypton, 5 ml of glycerol and 100 ml of phosphate buffer (pH 7.6) with water to a total volume of 1 l) supplemented with 50 µg/ml ampicillin at 32° C. overnight. Next, *E. coli* cells thus cultured were inoculated to a super broth supplemented with 50 µg/ml ampicillin at a cell concentration of 0.01 OD/ml at 660 nm, and cultured until the cell concentration reached 0.3 OD/ml at 660 nm. At this point the culture temperature was shifted to 42° C., and cultivation was further continued until the cell concentration reached 2.0 OD/ml at 660 nm.

Note, other transformants prepared in Example 13, i.e., *E. coli* W3110/pUCP$_L$CI799Bgl II, *E. coli* W3110/pUCP$_L$CI799R V, *E. coli* W3100/pUCP$_L$CI799Sal I, *E. coli* W3110/pUCP$_L$CI799BstE II$^L$, and *E. coli* W3110/pUCP$_L$CI799BstE II$^S$, were cultured according to the same procedure as described for *E. coli* W3110/pUCP$_L$-CI799Dra I.

(2) Expression of 799 in *E. coli*

*E. coli* W3110/ptrpΔ799 was cultured in a super broth supplemented with 50 µg/ml ampicillin at 37° C. overnight. Next, this cultured broth was inoculated to 20 volumes of M9 medium (0.5% sodium monohydrogen phosphate, 0.3% potassium dihydrogen phosphate, 0.5% sodium chloride, and 0.1% ammonium chloride) supplemented with 0.2% casamino acid, 5 µg/ml indoleacrylic acid, and 50 µg/ml ampicillin, and cultured at 37° C. for 7 hours.

Note, E. coli W3110/ptrp799-457Δ was also cultured according to the same procedure as described above.

(3) Determination of Product

The cultured broth prepared as above was centrifuged to collect cells, the whole protein of which was then analyzed according to a method of Laemmli, U.K., Nature 227, 680–685, 1970, by SDS-PAGE to detect the expressed target protein. Note, when cells were suspended in PBS(−) (0.8% sodium chloride, 0.02% potassium chloride, 0.15% sodium monohydrogen phosphate, and 0.02% potassium dihydrogen phosphate) and the suspension was treated with ultrasonication to disrupt cells and centrifuged, a major portion of the expressed proteins was recovered in a precipitate.

Example 15

Assay of C-terminal α-Amidating Enzyme 10.0 OD (at 660 nm) of cells cultured in Example 14 were suspended in 200 µl of PBS(−) containing 0.1% Triton, and the suspension was treated by ultra-sonication to disrupt the cells. Next, the disruption was centrifuged to recover a precipitated fraction, and the precipitate was then solubilized with 500 µl at 6 M guanidine hydrochloride. The solution thus prepared was then successively dialyzed in 200 ml of 4 M guanidine hydrochloride containing 10 mM Tris-HCl (pH 7.0) and 50 µM $CUSO_4$ for one hour, and then in 200 ml of 2 M guanidine hydrochloride containing 10 mM Tris-HCl (pH 7.0) and 50 µM $CuSO_4$, to prepare a sample for an assay of the enzyme activity.

Table 2 shows the activities of each of the proteins assayed. Note, a value of the enzyme activity of XA determined in Example 10 is shown for reference.

TABLE 2

| Derivatives | Activity units/cell OD600 = 1 |
|---|---|
| XA | 1.50 |
| 799Dra I | 0.06 |
| 799Bgl II | 0.06 |
| 799 RV | 0.06 |
| 799Sal I | 0.06 |
| Δ799 | 0.80 |
| 799-457Δ | 0.80 |
| 799 BstE II$^L$ | 0.10 |
| 799 BstE II$^S$ | 0 |

As seen from Table 2:

(1) Protein coded by the cDNA in pXA799 exhibits a C-terminal α-amidating enzyme.

(2) Not all of the amino acid sequence of protein 799Dra I is necessary for enzyme activity. Particularly, a C-terminal part of 799Dra I is not important. Actually, protein derivatives which lack the C-terminal part of 799Dra I, such as 799Bgl II, 799R V, 799Sal I, Δ799, 799-457Δ, and 799BstE II$^L$, exhibited a C-terminal α-amidating activity.

(3) But, since 799BstE II$^S$ does not exhibit an enzyme activity, a primary amino acid sequence of at least amino acids 1 to 329 coded by the cDNA derived from pXA799 is necessary for a C-terminal α-amidating activity.

Note, the enzyme activities of various derivatives shown in Table 2 are values of per unit cell mass (OD 660=1). Therefore the values do not denote the specific activity per protein.

Reference Example 1

Construction of Plasmid pT4TNFST8rop⁻ From Plasmid pBR322-PL-T4-hTNF Construction of Plasmids pPLT4TNF and pPLT4TNF-SalI Five micrograms of plasmid pBR322-PL-T4-hTNF the E. coli strain C600/CI transformed with this plasmid has been deposited with the Culture Collection of the Deutsche Sammlung von Mikroorganismen, Göttingen, West, Germany, under Accession Number DSM3175 was completely digested with the restriction enzyme ClaI and digested partially with AvaI (0.5 unit). Half a microgram of a chemically synthesized ClaI-AvaI linker DNA fragment having the base sequence (SEQ ID NOS:20 & 21):

```
CGATACTACTATGGTCAGATCATCTTCTCGAACC
    TATGATGATACCAGTCTAGTAGAAGAGCTTGGGGCT
(ClaI)                                  (AvaI)
``` was mixed in a ligation buffer and ligated with the previously obtained DNA fragment using 2 units of a T4DNA ligase. The solution was used to transform the E. coli strain W3110/CI, and from the transformants that were ampicillin-resistant and had the TNF producing capability, the desired plasmid pPLT4TNF was isolated by routine procedures.

Subsequently, a SalI cleavage site was inserted at a point immediately downstream of the TNF structural gene on the plasmid pPLT4TNF in accordance with the method of Morinaga, Y. et al. described in Biotechnology 2: 636–639, 1984. First, the pPLT4TNF was divided into two portions. One of them was completely cleaves with EcoRI and PstI to obtain a double-stranded DNA fragment that was deficient of the PL promotor containing DNA fragment. The other portion was cleaved with HindIII and BstEII to obtain a double-stranded DNA fragment that was deficient of a fragment containing part of the TNF gene at its 3' end. The two DNA fragments (III) and (IV) were mixed with AB180 that was a chemically synthesized single-stranded DNA having a SalI cleavage site and the base sequence (SEQ ID NO:22): 5'-ATCATTGCCCTGTGAGTCGACCGAACAT CCAACCTT-3'. By heating at 100° C., the double-stranded DNA was changed to single-stranded DNA, which then was slowly cooled to form a double-stranded chain by annealing. To the reaction solution, dNTPs and DNA polymerase (Klenow fragment), as well as T4DNA ligase and ATP were added and reaction was carried out to form a closed circular double-stranded DNA. The resulting solution was used to transform the E. coli strain W3110/CI and ampicillin-resistant transformants were selected. Plasmid was isolated from the transformants and restriction enzyme analysis revealed that it was the desired plasmid pPLT4TNF-SalI which contained a SalI cleavage site immediately downstream of the TNF structural gene.

Construction of Plasmid pPLT4TNFST8

The plasmid pPLT4TNF-SalI constructed in Reference Example 1 was subjected to the following procedures in order to construct the plasmid pPLT4TNFST8 wherein the terminator trp a was inserted at a point immediately downstream of the codon for terminating the translation of the TNF structural gene on pPLT4TNF-SalI and whose drug resistance marker was tetracycline, rather than ampicillin.

A fragment (1) was obtained by cleaving pPLT4TNF-SalI with AhaIII and SalI and which harbored the PLT4 promoter and the TNF gene. Using a T4DNA ligase, this fragment was ligated with a chemically synthesized DNA segment (2) and an EcoRI-AhaIII DNA fragment (3) in a three-fragment ligation. Segment (2) ended with a SalI cohesive site and an EcoRI cohesive site and had the following base sequence (SEQ ID NOS:23 & 24) (terminator trp a: trp a):

```
TCGACAGCCCGCCTAATGAGCGGGCTTTTTTTCTCGG
    GTCGGGCGGATTACTCGCCCGAAAAAAAAGAGCCTTAA
   SalI                                    EcoRI.
```

Fragment (3) was a large (3.2 kb) fragment that contained the tetracycline resistance gene Tc$^r$ and which was obtained by cleaving the plasmid pBR322 with AhaIII and EcoRI. The ligation product was used to transform the E. coli strains W3110/CI and WA802/CI. The transformants were tetracycline-resistant and screened for ampicillin sensitivity. Plasmid was isolated from each of the transformants by routine procedures and restriction enzyme analysis verified the construction of the desired plasmid pPLT4TNFST8.

The E. coli strain WA802/CI/pPLT4TNFST8 obtained by transformation with the plasmid pPLT4TNFST8 was named SBM 281 and has been deposited with the Fermentation Research Institute, the Agency of Industrial Science and Technology, under Deposit Number FERM BP-906.

Construction of Plasmid pT4TNFST8

Five micrograms of the plasmid pPLT4TNFST8 obtained in Reference Example 2 was partially digested with EcoRI (0.5 unit) and the EcoRI cohesive end was made blunt (filled in) with a DNA polymerase in the presence of dNTPs (i.e., dATP, dGTP, dTTP and dCTP). Subsequently, the pPLT4TNFST8 was cleaved at the AhaIII site by addition of 5 units of AhaIII and ligation was conducted with a T4DNA ligase. The resulting ligation solution was used to transform the E. coli strains WA802 and W3110. Plasmid DNA was isolated from the tetracycline-resistant transformants (which were named WA802/pT4TNFST8 and W3110/pT4TNFST8) and restriction enzyme analysis revealed that these transformants had the desired plasmid pT4TNFST8.

Construction of Plasmid pT4TNFST8rop$^-$

The plasmid pT4TNFST8rop$^-$ which lacked the pBR322-derived rop (repressor of primer) gene on pPLT4TNFST8 having the function of controlling plasmid DNA replication was constructed by the following procedures.

Plasmid pBR322 was cleaved with PvuII and BalI (each providing a blunt end), ligated with a T4DNA ligase and used to transform the E. coli strain WA802. The transformants were screened for resistance to both ampicillin and tetracycline, and from the active transformants the plasmid pBR322ΔBalI lacking the small PvuII-BalI DNA fragment on pBR322 was isolated.

The plasmid pBR 322ΔBalI was cleaved with HindIII and AhaIII. The plasmid pPLT4TNFST8 that was obtained in Reference Example 2 was partially digested with EcoRI, filled in at the EcoRI cohesive end (see Reference Example 3) and cleaved with HindIII. The two DNA fragments were ligated with a T4DNA ligase. The ligation product was used to transform the E. coli strains WA802 and W3110 and the transformants were screened for tetracycline-resistant clones. Plasmid DNA was isolated from the clones and restriction enzyme analysis verified the construction of the desired plasmid pT4TNFST8rop$^-$. The E. coli strains WA802 and W3110 having the plasmid pT4TNFST8rop$^-$ were named WA802/pT4TNFST8rop and W3110/pT4TNFST8rop$^-$, respectively, and their capability of TNF production was determined.

Reference Example 2

Construction of Plasmid pUC-P$_L$-trp a

A repressor cI region of λ cI857 phage DNA (Takara Shuzo, Japan) was introduced to a multi-cloning site of plasmid pUC19 (Takara Shuzo, Japan) to construct plasmid pUC-cI. Next, an ArtII-EcoRI fragment containing P$_L$ promotor region was prepared from plasmid pS224-3, and was inserted into ArtII/EcoRI sites of the plasmid pUC-C$_I$ to construct plasmid pUC-P$_L$. To the plasmid pUC-P$_L$, synthetic trp a terminator (SEQ ID NO:25 & 26):

(5'-TCGACAGCCCGCCTAATGAGCGGGCTTTT TTTTC-3'

3'-GTCGGGCGGATTACTCGCCCGAAAAAAAAG AGCC-5') having AvaI and SalI cohesive ends was inserted to construct plasmid pUC-P$_L$-trp a.

Reference Example 3

Construction of Plasmid pS224-3

1) Preparation of cDNA Library, and Isolation and Identification of α-hANP Gene (1-a) Preparation of cDNA Library From two human atrium cordis obtained from an 82 years old female and 61 year old male, 1 mg of RNA was extracted with 4M guanidium thiocyanate according to a method of Chirgwin et al. (Chirgwin, J. M. et. al., Biochemistry 18, 5294–5299, 1979). The RNA was then subjected to an oligo (dT) cellulose column using 10 mM Tris-HCl buffer, pH 7.2, containing 0.5 mM LiCl, 10 mM EDTA and 0.5% SDS as a binding buffer, and 75 μg of poly (A) $^+$RNA (mRNA) was isolated (Nakazato, H. & Edmonds, D. S., Meth. Enzym. 29, 431–443, 1974). 15 μg of the poly (A) +RNA and 4.2 μg of vector primer DNA were used to prepare a cDNA library (plasmids) according to the Okayama-Berg method (Mol. Cell Biol. 2, 161–170, 198), and the cDNA library was used to transform E. coli WA802. The transformants were screened on an LB-agar medium supplemented with 40 γ/ml of ampicillin, and about 40,000 colonies of ampicillin resistant transformants were obtained per microgram of starting mRNA.

(1-b) Isolation of α-hANP Clone

About 40,000 colonies were replicated on a nitrocellulose filter, and the filter was incubated on an LB agar plate supplemented with 40 γ/ml of ampicillin at 37° C. for 6 hours. The filter was transferred onto an LB agar plate supplemented with 180 γ/ml of chloramphenicol, and incubated at 37° C. over night. The colonies on the filter were lysated with 0.5N NaOH, and neutralized to pH 7.0, and the filter was soaked in 0.5M Tris-HCl buffer, pH 7.0, containing 1.5 N NaCl, and in 3×SCC (0.15 M NaCl. 0.05M sodium citrate) for 5 minutes respectively. Finally, cell debris on the filter was removed with a paper towel, and the filter was air-dried and then baked at 80° C. for 2 hours. The filters were then subjected to hybridization with a mixture of probes I and II consisting of chemically synthesized 14-mer oligonucleotides (SEQ ID NOS:27 & 28) labeled with $^{32}$p at their 5'-end (Grunstein, M. & Hogness, D. S., Proc. Natl. Acad. Sci. USA, 72, 3961–3965, 1975).

```
         T  T
3'-TACCTGGTAGCC-5'              PROBE I
      AC  T
      A

T
3'-TACCTGTCTTAGCC-5'            PROBE II
     A  C  A
```

The 14-mer oligonucleotides used as a probe are possibly complementary with mRNA coding for an amino acid sequence Met-Asp-Arg-Ile-Gly and have been labeled with $^{32}$p at their 5'-end using $^{32}$p γ-ATP and T4 kinase and have a specific activity of 1 to 3×10$^6$ cpm/p mole. The hybridization was carried out in 3×SCC containing 1×Denhardts (0.2% BSA. Armour Pharmaceutical Company; 0.2% Ficol, Sigma; and 0.2% polyvinyl pyrrolidone, Wako Jyunyaku), 0.1% SDS and 50 μg/ml salmon testis DNA, at 38° C. for 16 hours. The filter was then washed with 3×SCC containing 0.1% SDS, air-dried, and placed in contact with an X-ray film. As a result, 85 positive clones were observed on the film. The 85 positive clones were then subjected to the colony hybridization using the same procedure as described above, except that the probe I and probe II were separately used at 40° C. and 38° C. for each probe. As a result, 23 clones were obtained which hybridize with the probe II but do not hybridize with the probe I. Among these 23 clones 8 clones were used to isolate plasmid DNA according to a conventional method. The isolated plasmid DNAs were sequenced using the probe II as the primer according to a dideoxy chain termination method (Sanger F. et al, Proc. Natl. Acad. Sci. USA, 74, 4563–5467, 1977). As a result, all of the plasmids contained a base sequence corresponding to a part of an amino acid sequence of α-hANP and, consequently, the above-mentioned 8 clones were confirmed to have a plasmid containing cDNA of α-hANP. Among the 8 plasmids, 2 plasmids having a longer insert containing cDNA of γ-hANP were selected, and designated as phANP1 and phANP82. The inserts of plasmids phANP1 and phANP82 were sequenced. As a result, the plasmids phANP1 and phANP82 contained an insert of about 950 bp and an insert of about 850 bp, respectively.

2) Construction of γ-hANP Gene Expression Vector (2-1) Insertion of γ-hANP Gene into M13 DNA 0.44 μg of M13mpB RF-DNA was cleaved with 16 units of PstI in 20 μl of Medium-Salt Buffer (10 mM Tris-HCl buffer, pH 7.5, containing 50 mM NaCl, 10 mM MgCl$_2$, 1 mM DTT) at 37° C. for 1 hour. The mixture was then heated at 65° C. for 10 minutes to stop the enzyme reaction. On the other hand, 20 μg of plasmid phANP1 DNA was cleaved with 160 units of PstI in 100 μl of the Medium Salt Buffer at 37° C. for 1 hour, and the reaction mixture was subjected to 1% agarose gel electrophoresis. A part of the gel containing a DNA fragment corresponding to about 700 bp was cut to obtain an agarose piece, and the DNA fragment was extracted by the electro-elution method and purified.

66 ng of the DNA fragment from M13mp8 RF-DNA and 1 μg of the 700 bp DNA fragment were ligated using 5.6 units of T4 DNA ligase (Takara Shuzo, Japan) in 20 μl of ligation buffer (20 mM Tris-HCl buffer, pH 7.6, containing 10 mM MgCl$_2$, 1 mM ATP, 5 mM DTT) at 14° C. for 16 hours. E. coli JM103 cells were treated with CaCl$_2$ according to a conventional method to obtain a suspension of the E. coli cells in 50 mM CaCl$_2$, and the ligation mixture prepared as above (20 μl) was added to the E. coli suspension to transform the E. coli.

The transformant clones were screened as follows. The suspension containing transformant E. coli cells was diluted in YT soft agar medium containing x-Gal and IPTG (prepared by adding 10 μl of 10 mM IPTG, 50 μl of 2% x-gal and 0.2 ml of E. coli JM103 suspension grown in a logarithmic growth phase into 3 ml of solution containing 0.6% agar, 0.8% Bacto trypton, 0.5% yeast extract and 0.5% NaCl). 0.3 ml of the diluted suspension was spread on YT agar medium (1.5% agar, 0.8% Bacto trypton, 0.5% yeast extract and 0.5% NaCl), and incubated at 37° C. for 16 hours to form plaques. Among the plaques, 10 μlaques were selected, and inoculated into 2×YT liquid medium (1.6% Bacto trypton, 1% yeast extract and 1.0% NaCl) and cultured at 37° C. for 8 hours. 1 ml of the cultured medium was centrifuged at 10,000 rpm for 10 minutes to recover a supernatant containing phage. The phage DNA (single strand DNA) was isolated and purified as follows.

To 800 μl of the phase liquid, 200 μl of 20% polyethylene glycol (PEG 6000) containing 2.5N NaCl was added, and the mixture was allowed to stand at room temperature for 20 minutes and centrifuged at 10,000 rpm for 5 minutes to precipitate the phage. The precipitated phage was dissolved in 100 μl of TE buffer (10 mM Tris-HCl, pH 8.0, 1 mM EDTA), and to the solution 50 μl of phenol saturated with water was added, the mixture was vigorously stirred for 5 minutes, and centrifuged at 10,000 rpm for 5 minutes. After sampling 80 μl of the aqueous phase, to the aqueous phase 3 μl of 3M sodium acetate, pH 8.0, and 200 μl of ethanol was added, and the mixture was cooled at −70° C. for 10 minutes, and then centrifuged at 10,000 rpm for 10 minutes to precipitate DNA. The precipitated DNA was washed once with ethanol, and dissolved in 50 μl of the above-mentioned TE buffer. A part of a base sequence of each phage DNA was sequenced according to the dideoxy chain termination method (Methods in Enzymology, 65, 560–580, 1980, Academic Press, New York), and among 10 clones, 2 clones containing a lower strand (DNA fragment having a base sequence complementary to mRNA) were selected. The phage DNA thus obtained were used as a template for in vitro mutation.

(2-b) Incorporation of EcoRI Cleavage Site and Translation Initiation Codon by In-vitro Mutation To 5 μl of the single strand phage DNA solution described above, 1 μl of 0.2M Tris-HCl buffer, pH 7.5, containing 0.1M MgCl$_2$ and 0.5M NaCl, and 2 μl of water, were added 2 μl of solution containing 10 pmole of 36-mer chemically synthesized DNA fragments (SEQ ID NO:29) (5'-CTCCTAGGTCAGGAATTCATGAATCCCATGTACAAT-3') phosphorylated at the 5' end to form 10 μl of a mixture. The mixture was heated at 65° C. for 5 minutes, and allowed to stand for 10 minutes at room temperature.

To the mixture, 1 μl of 0.2M Tris-HCl buffer (pH 7.5) containing 0.1M MgCl, 2 μl of 0.1M DTT, 1 μl of 10 mM ATP, 2 μl each of 10 mM dATP, dDTP, dCTP and dTTP, 2 μl of water, 5 units of DNA polymerase I Klenow fragment (Boehringger Manheim) and 2.8 units of T4 DNA ligase (Takara Shuzo) were added, and the mixture was incubated at 15° C. for 16 hours. 20 μl of the reaction mixture was used to transform E. coli JM103.

As described above for the preparation of phage DNA, plagues were formed on a YT soft agar medium, and 48 clones were selected. The clones were inoculated to 2×YT medium, and cultured at 37° C. for 8 hours. 1 ml of the cultured medium was centrifuged at 10,000 rpm for 10 minutes to recover the supernatant as phage solution. On the other hand, RF-DNA was extracted and isolated from the precipitated cells according to the alkaline extraction method (Birnboim, H. C. & Doly, J., Nucl. Acid. Res., 7, 1513–1523, 1979). The RF-DNA was then cleaved with 4.2 units of EcoRI (Takara Shuzo) in EcoRI buffer (100 mM Tris-HCl, pH 7.5, 50 mM NaCl, 5 mM MgCl$_2$) at 37° C. for 1 hour. The reaction mixture was subjected to 2% agarose gel electrophoresis, and a clone providing a DNA fragment of about 530 bp was selected. The clone was designated as M13mp8-hANP525.

To 400 ml of 2×YT liquid medium, 0.4 ml of culture of E. coli JM103 infected with the above-mentioned phage clone and 4 ml of a not-infected culture of E. coli JM103 were inoculated. The medium was then incubated at 37° C. for 12 hours. The cultured medium was centrifuged to obtain an infected cell precipitation and a supernatant phage solution. From the infected cells, RF-DNA was obtained by a densitygradient centrifugation method using cesium chloride and ethidium bromide according to a conventional method. On the other hand, from the supernatant phage solution phage DNA was obtained, and the phage DNA was sequenced according to the dideoxy chain termination method. As a result, it was confirmed that a translation initiation codon ATG and EcoRI cleavage recognition site GAATTC, i.e., a base sequence GAATTC ATG, were inserted immediately upstream of the γ-hANP gene.

(2-c) Construction of Expression Vector for γ-hANP Gene

An expression plasmid pS223-3 was constructed from plasmid pS20 and M13mp8-hANP525. The starting plasmid pS20 was constructed by the inventors, and E. coli N4380/pS20 containing the plasmid pS20 was designated as SBM271, and deposited as FERM BP-535 as described above. The plasmid pS20 contains λ phase $P_L$ promotor, and can express a foreign gene inserted to a site downstream of the promotor under the control of the promotor.

The plasmid pS20 was constructed as follows. Bacteriophage λ C1857 DNA was cleaved with BamHI and HindIII to obtain a 2.4 kb DNA fragment containing the $\lambda P_L$ promotor. The DNA fragment was inserted into a region of HindIII-BamHI in pBR322 to obtain a plasmid which is substantially the same as the plasmid pKO 30 described in Nature 292, 128, 1981. To the Hpa I cleavage site of the plasmid thus obtained, 1.3 Kb Hae III DNA fragment containing NutR, $tR_1$, CII and a part of O protein derived from bacteriophage λcy3048 (from Dr. Hiroyuki Shimatake, Medical Department, Toho University) was inserted to obtain plasmid (pS9), wherein CII is present in the direction the same as the transcription direction of $\lambda P_L$. The plasmid (pS9) was cleaved with Bql II and Rsa I to obtain a 0.65 Kb DNA fragment containing $P_L$ promotor, DNA sequence of protein N' which is a part of an N protein lacking a C terminal, and the Shine-Dalgarno sequence (SD) of a CII gene. The Rsa I and of the 0.65 Kb DNA fragment was added with the Eco RI linker (SEQ ID NOS:30 & 31):

-CGGAATTCCG-
-GCCTTAAGGC- (New England Biolabos. Inc.), and then the Bgl II end of the same DNA fragment was converted to a blunt end with T4 DNA polymerase. The DNA fragment thus obtained was ligated with a DNA fragment prepared by Eco RI cleavage of plasmid pBR322 and conversion of the pBR322 ends to blunt ends to form a plasmid (pS13). In the plasmid (pS13), the $P_L$ promotor is oriented in the direction the same as the transcription direction of the tetracycline resistant gene (Tc$^r$) derived from pBR322. The plasmid (pS13) was cleaved with Eco RI and Sal I, and a large fragment was isolated. The large fragment was then ligated with a DNA fragment containing a foreign gene, i.e., human γ-interferon gene GIF, which fragment was prepared by cleavage of plasmid pGIF4 with Eco RI and Sal I. The plasmid pGIF4 was disclosed in Japanese Unexamined Patent Publication No. 58-201995 (U.S. Pat. Ser. No. 496176), and E. coli containing the plasmid was designated as SBMG 105 and deposited at the FRA under the Budapest Treaty on the International Recognition of the Deposit of Microorganisms for the Purpose of Patent Procedure as FERM BP-282 on May 6, 1982.

Plasmid pS20 was cleaved with Eco RI, and hydrolyzed with an exonuclease Bal 31 to form DNA fragments having various lengths. The DNA fragments were ligated with Xba I linker (from New England Biolabos Inc.; dCTCTAGAG) to obtain plasmid pS20X. The plasmid pS20X was cleaved with Xba I and Sal I to delete any Xba I-Sal I short fragments. On the other hand, plasmid pIN4GIF54 was cleaved with Xba I and Sal I to obtain a short Xba I-Sal I fragment containing human γ-interferon gene, which short fragment was then inserted to the above-mentioned cleaved pS20X in place of the deleted Xba I-Sal I fragment to form plasmids. Among the plasmids thus formed, a plasmid which can effectively express the human γ-interferon gene when transformed into E. coli was designated as pS83-3. The above-mentioned plasmid pIN4GIF54 and a method for measuring an amount of γ-interferon were disclosed in Japanese Unexamined Patent Publication No. 60-24187 (U.S. Pat. Ser. No. 632204). Plasmid sP83-3 was cleaved with Eco RI and Sal I to delete the Eco RI-Sal I short fragment consisting of the human γ-interferon gene (GIF). The plasmid M13mpB-hANP525 was cleaved with Eco RI and Sal I to obtain an about 510 bp Eco RI-Sal I fragment containing γ-hANP gene, which fragment was then inserted to the cleaved pS83-3 in place of the deleted Eco RI-Sal I fragment consisting of GIF to form plasmid pS223-3. The plasmid pS223-3 contains an $\lambda P_L$ promotor region, SD sequence of E. coli lpp gene, and γ-hANP gene, in this order.

Another γ-HANP gene expression vector pS224-3 was constructed as follows. The plasmid pS83-3 was cleaved with Xba I and Eco RI to delete the SD sequence of the lpp gene, and in place of the delected SD sequence of the lpp gene, a chemically synthesized DNA fragment AGGAGGT with Xba I and Eco RI cohesive ends, which is the SD sequence of the bacteriophage MS2A protein gene, was inserted into the cleaved pS83-3 to form plasmid pSS3-3. The plasmid pSB4-3 DNA was cleaved with Eco RI and Sal I to delete the Eco RI-Sal I short fragment consisting of GIF. The plasmid M13mp8-hANP525 DNA was cleaved with Eco RI and Sal I to obtain an about 510 bp Eco I-Sal RI fragment containing the γ-hANP gene, which fragment was then inserted into the cleaved pS84-3 DNA in place of the deleted Eco RI-Sal I fragment consisting of GIF to obtain plasmid pS224-3. The plasmid pS224-3 thus obtained contained a $\lambda P_L$ promotor region, SD sequence of MS2A, and γ-hANP gene, in this order. E. coli N4380 transformed with the plasmid pS224-3 was designated as E. coli N4380/pS244-3.

Reference Exapmle 4

Construction of pIN4GIF54

Plasmid pIN4GIF54 was constructed from (1) DNA fragment containing the lipoprotein gene promotor region (indicated by lpp in the figure) as obtained by digestion of the plasmid pINIA2 with the restriction enzymes XbaI and PstI, (2) oligonucleotide having XbaI and EcoRI cohesive ends and (3) DNA fragment containing the hINF-γ gene as obtained by digestion of the plasmid pGIF54 with EcoRI and PstI. The procedure followed was as described hereinbelow. The restriction enzymes used were all products of Takara Shuzo K.K.

A) Preparation of XbaI-PstI DNA fragment of pINI-A2

The plasmid pINI-A2 is a gift from Dr. Inoue of New York State University. A host Escherichia coli strain obtained by transformation with said plasmid has been named JA221/pINI-A2 and deposited with the Fermentation Research Institute, 1-3, Higashi 1-chome Tsukuba-shi, Ibaraki, Japan, under Deposit No. FERM BP-320, on Jul. 18, 1983 under the Budapest treaty.

The pINI-A2 DNA (3 μg) was digested with 15 units each of XbaI and PstI in 150 μl of 1×TA solution (33 mM Tris acetate buffer pH 7.6, 66 mM potassium acetate, 10 mM magnesium acetate and 0.5 mM dithiothreitol) at 37° C. for 60 minutes. The reaction mixture was subjected to 1.0% agarose gel electrophoresis and a gel portion located at the position corresponding to about 980 b.p. (base pairs) was cut out and placed in a dialysis tube, and the XbaI-PstI DNA fragment was eluted by electrophoresis. After removal of ethidium bromide from the eluate by adding an equal amount of phenol thereto, 2.5 volumes of ethanol was added. After standing at −80° C. for 30 minutes, the mixture was centrifuged at 10,000 rpm for 10 minutes, whereby the DNA fragment was obtained as an ethanol precipitate. To this ethanol precipitate was added 10 μl of distilled water for dissolving the DNA fragment.

B) Preparation of EcoRI-PstI DNA Fragment of pGIF54

Plasmid pGIF54 is essentially the same plasmid as pGIF4 disclosed in Japanese Patent Application No. 86,180/1982. An *Escherichia coli* transformant, WA802/pGIF4, obtained by transformation with said plasmid containing the chemically synthesized gene coding for the amino acid sequence of hIFN-γ has been named SBMG105 and deposited with the Fermentation Research Institute, the Agency of Industrial Science and Technology as FERM P-6522 on May 6, 1982, and transferred to deposition under the Budapest treaty, as FERM BP-282, on May 2, 1983.

The pGIF54 DNA (3 μg) was digested with 15 units each of EcoRI and PstI in 30 μl of 1×TA solution at 37° C. for 60 minutes, followed by 0.7% agarose gel electrophoresis, whereby an EcoRI-PstI DNA fragment of about 3.4 Kb was eluted from the gel. The eluate was subjected to phenol treatment and ethanol precipitation in the same manner as above. To the ethanol precipitate, 10 μl of distilled water was added for dissolution of the DNA fragment.

C) Preparation of Oligonucleotide Having XbaI and EcoRI Cohesive Ends

For the expression of complete hINF-γ protein, an oligonucleotide having the Shine-Dalgarno (SD) sequence downstream from the XbaI cleavage site of pINIA2 and further having an EcoRI cohesive end, namely the oligonucleotide (SEQ ID NOS: 32 & 33),

SP

5' CTAGAGGTAG3'

3'TCCATCTTAA5'

XbaI cohesive end EcoRI cohesive end was synthesized by the solid phase method. The synthetic procedure has been disclosed in detail in Japanese Patent Application No. 86,180/1982.

The above oligonucleotide (100 picomoles) was phosphorylated at the 5'-OH in 30 μl of a kinase reaction solution (50 mM Tris hydrochloride buffer, pH 8.0, 10 mM $MgCl_2$, 10 mM dithiothreitol), with 2 units of T4 polynucleotide kinase (Takara Shuzo K. K.) added, at 37° C. for 60 minutes.

D) Construction of pIN4GIF54

The plasmid pIN4GIF54 was constructed by ligation of the three DNA fragments prepared above in accordance with the following procedure. Thus, to a mixture of 5 μl of a solution of the XbaI-PstI DNA fragment of pINIA2 (solution of the ethanol precipitate in 10 μl of distilled water), 5 μl of a solution of the EcoRI-PstI DNA fragment of pGIF54 (solution of the ethanol precipitate in 10 μl of distilled water) and 3 μl of a solution of the phosphorylated oligonucleotide (10 picomoles), there were added 2 μl of a ligation reaction medium 10-fold higher in concentration (20 mM Tris hydrochloride buffer, pH 7.6, 10 mM $MgCl_2$), 2 μl of 4 mM ATP and 1 μl of T4 DNA ligase (Boehringer Mannheim) (5 units), and the ligation was carried out at 16° C. overnight.

(2) Transformation of *Escherichia Coli*

A) Transformation of *Escherichia coli* WA802

*Escherichia coli* WA802 was cultured in 2.0 ml of L-broth at 37° C. overnight, 0.3 ml of the culture broth was added to 30 ml of L-broth, and shake culture was performed at 37° C. for 2 hours, followed by centrifugation at 3,000 rpm for 10 minutes. To the 10 thus-obtained cells was added 10 ml of 50 mM $CaCl_2$ for suspending the cells, and centrifugation was conducted at 3,000 rpm for 10 minutes. To the thus-obtained cells was added 1.0 ml of 50 mM $CaCl_2$ solution, and the mixture was allowed to stand in an ice bath for 60 minutes. To 0.2 ml of this suspension of $Ca^{++}$-treated cells was added 10 μl of the ligation reaction mixture obtained in Reference Example 4-D (containing the above-mentioned three DNA fragments ligated), the mixture was allowed to stand in an ice bath for 60 minutes, them 2 ml of L-broth was added and incubation was conducted at 37° C. for 60 minutes. The culture broth was used for plating on nutrient agar medium (BBL) containing 40 μg/ml of ampicillin. After incubation at 37° C. overnight, ampicillin-resistant transformants were selected. One of the transformants obtained was used for plasmid DNA separation therefrom by the conventional method (cleared lysate method). The base sequence of the DNA at and around the XbaI-EcoRI region inserted was determined by the Maxam-Gilbert method (Methods in Enzymology, 65: 499–560, 1980) and it was confirmed that the DNA had the desired DNA base sequence. This plasmid was named pIN4GIF54 and the transformant *Escherichia coli* strain carrying the same was named WA802/pIN4GIF54.

SEQUENCE LISTING (1) GENERAL INFORMATION:

(iii) NUMBER OF SEQUENCES: 77

(2) INFORMATION FOR SEQ ID NO:1:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Peptide
      (B) LOCATION: 1
      (D) OTHER INFORMATION: /note= "Amino acid 1 is Xaa wherein Xaa = pGlu."

(xi) SEQUENCE DESCRIPTION: SEQ ID NO:1:

Xaa His Pro Xaa
1

(2) INFORMATION FOR SEQ ID NO:2:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1
        (D) OTHER INFORMATION: /note= "Amino acid 1 is Xaa wherein
            Xaa = pGlu."

(xi) SEQUENCE DESCRIPTION: SEQ ID NO:2:

Xaa Gln Asp Tyr Thr Gly Trp Met Asp Phe Xaa
1               5                   10

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Ser Leu Ser Asn Asp
1               5

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Xaa Ser Leu Ser Asn Asp
1               5

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Pro Pro Val Ser Ser Ser Xaa
1               5

(2) INFORMATION FOR SEQ ID NO:6:

(i) SEQUENCE CHARACTERISTICS:
           (A) LENGTH: 14 amino acids
           (B) TYPE: amino acid
           (C) STRANDEDNESS: single
           (D) TOPOLOGY: linear (ii) MOLECULE TYPE: protein (ix) FEATURE:
           (A) NAME/KEY: Peptide
           (B) LOCATION: 6
           (D) OTHER INFORMATION: /note= "Amino acid 6 is Xaa wherein
               Xaa = X and is predicted as a Cys residue"

(xi) SEQUENCE DESCRIPTION: SEQ ID NO:6:

Ser Leu Ser Asn Asp Xaa Leu Gly Thr Arg Pro Val Met Ser
1               5                   10

(2) INFORMATION FOR SEQ ID NO:7:

(i) SEQUENCE CHARACTERISTICS:
           (A) LENGTH: 36 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:7:

GTCATTGGAA AGTGACATGA ATTCTTCCTC ATACCT                               36

(2) INFORMATION FOR SEQ ID NO:8:

(i) SEQUENCE CHARACTERISTICS:
           (A) LENGTH: 15 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:8:

GCGTCACACT CAGCT                                                     15

(2) INFORMATION FOR SEQ ID NO:9:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:9:

GTCACCACCA TACAGAAGCT GAGCCTGAG                                      29

(2) INFORMATION FOR SEQ ID NO:10:

(i) SEQUENCE CHARACTERISTICS:
           (A) LENGTH: 31 base pairs
           (B) TYPE: nucleic acid
           (C) STRANDEDNESS: single
           (D) TOPOLOGY: linear (ii) MOLECULE TYPE: DNA (genomic)

(xi) SEQUENCE DESCRIPTION: SEQ ID NO:10:

AAGAATACAG GACTTCAGCA GCCTAAATGA G                                   31

(2) INFORMATION FOR SEQ ID NO:11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GTATTCTTCT CAGGCTCAGC TTCTGTATGG TG                        32

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TCGACTCATT TAGGCTGCTG AAGTCCT                            27

(2) INFORMATION FOR SEQ ID NO:13:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CTTAATTAAT TAAGCA                                          16

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GTACGAATTA ATTAATTCGT TCGA                              24

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Met Gly Ile Leu
1

(2) INFORMATION FOR SEQ ID NO:16:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:16:

Leu Gln Ala Lys Leu Ile Asn
1               5

(2) INFORMATION FOR SEQ ID NO:17:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:17:

Gly Asp Pro Leu Glu Ser Thr Cys Arg His Ala
1               5                   10

(2) INFORMATION FOR SEQ ID NO:18:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:18:

Gly Asp Pro Leu Glu Ser Thr Cys Arg His Ala
1               5                   10

(2) INFORMATION FOR SEQ ID NO:19:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:19:

CAGCAGCCTA AATAGGTCGA CGAAGAAGTA TTAAAT                                  36

(2) INFORMATION FOR SEQ ID NO:20:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:20:

CGATACTACT ATGGTCAGAT CATCTTCTCG AACC                                    34

(2) INFORMATION FOR SEQ ID NO:21:

-continued

```
    (i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TATGATGATA CCAGTCTAGT AGAAGAGCTT GGGGCT                           36

(2) INFORMATION FOR SEQ ID NO:22:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

ATCATTGCCC TGTGAGTCGA CCGAACATCC AACCTT                           36

(2) INFORMATION FOR SEQ ID NO:23:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

TCGACAGCCC GCCTAATGAG CGGGCTTTTT TTTCTCGG                         38

(2) INFORMATION FOR SEQ ID NO:24:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GTCGGGCGGA TTACTCGCCC GAAAAAAAAG AGCCTTAA                         38

(2) INFORMATION FOR SEQ ID NO:25:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TCGACAGCCC GCCTAATGAG CGGGCTTTTT TTTC                             34

(2) INFORMATION FOR SEQ ID NO:26:

(i) SEQUENCE CHARACTERISTICS:
        (A) LENGTH: 34 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO:26:

GTCGGGCGGA TTACTCGCCC GAAAAAAAAG AGCC                                        34

(2) INFORMATION FOR SEQ ID NO:27:

(i) SEQUENCE CHARACTERISTICS:
                (A) LENGTH: 12 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: misc_feature
                (B) LOCATION: 6
                (D) OTHER INFORMATION: /note= "Nucleotide 6 is N wherein N
                    = G or A."

(ix) FEATURE:
                (A) NAME/KEY: misc_feature
                (B) LOCATION: 7
                (D) OTHER INFORMATION: /note= "Nucleotide 7 is N wherein N
                    = T, G, C, or A."

(ix) FEATURE:
                (A) NAME/KEY: misc_feature
                (B) LOCATION: 10
                (D) OTHER INFORMATION: /note= "Nucleotide 10 is N wherein
                    N = T, G, or T."

(xi) SEQUENCE DESCRIPTION: SEQ ID NO:27:

TACCTNNTAN CC                                                                12

(2) INFORMATION FOR SEQ ID NO:28:

(i) SEQUENCE CHARACTERISTICS:
                (A) LENGTH: 14 base pairs
                (B) TYPE: nucleic acid
                (C) STRANDEDNESS: single
                (D) TOPOLOGY: linear (ii) MOLECULE TYPE: DNA (genomic)

(ix) FEATURE:
                (A) NAME/KEY: misc_feature
                (B) LOCATION: 6
                (D) OTHER INFORMATION: /note= "Nucleotide 6 is N wherein N
                    = G or A."

(ix) FEATURE:
                (A) NAME/KEY: misc_feature
                (B) LOCATION: 9
                (D) OTHER INFORMATION: /note= "Nucleotide 9 is N wherein N
                    = T or C."

(ix) FEATURE:
                (A) NAME/KEY: misc_feature
                (B) LOCATION: 12
                (D) OTHER INFORMATION: /note= "Nucleotide 12 is N wherein
                    N = T, G, or A."

(xi) SEQUENCE DESCRIPTION: SEQ ID NO:28:

TACCTNTCNT ANCC                                                              14

(2) INFORMATION FOR SEQ ID NO:29:

(i) SEQUENCE CHARACTERISTICS:
                (A) LENGTH: 36 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CTCCTAGGTC AGGAATTCAT GAATCCCATG TACAAT                                    36

(2) INFORMATION FOR SEQ ID NO:30:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CGGAATTCCG                                                                  10

(2) INFORMATION FOR SEQ ID NO:31:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GCCTTAAGGC                                                                  10

(2) INFORMATION FOR SEQ ID NO:32:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

CTAGAGGTAG                                                                  10

(2) INFORMATION FOR SEQ ID NO:33:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

TCCATCTTAA                                                                  10

(2) INFORMATION FOR SEQ ID NO:34:

(i) SEQUENCE CHARACTERISTICS:
        (A) LENGTH: 2610 base pairs
        (B) TYPE: nucleic acid
        (C) STRANDEDNESS: single
        (D) TOPOLOGY: linear -continued (ii) MOLECULE TYPE: protein (ix) FEATURE:
    (A) NAME/KEY: CDS
    (B) LOCATION: 266..1468

(ix) FEATURE:
    (A) NAME/KEY: mat_peptide
    (B) LOCATION: 378..1468

(ix) FEATURE:
    (A) NAME/KEY: sig_peptide
    (B) LOCATION: 266..375

(xi) SEQUENCE DESCRIPTION: SEQ ID NO:34:

```
ACCATTCAGT TGTGGGTGAT CAGCAGTGTG CCAGCATCTA AAGGAACCAA ATCATTGCAA      60

CTTGTACCCT GATCAGGCAC CTTATACTGG ACGCAAGTGC ACTTCTTCCC TCAAGAAGAT     120

CATATCCCGG GAAGAATGTG TATTTCTGGT TACCTGCGGG GCTAGCACTG ATGGAGTAGG     180

GGGGATTTAT CTGGTTTCCT AATTACCAGG ATTACAACTT GCCTTTAATT TACTCCTGCA     240

GTAAGGCACA GACCACAGGG TGGAC ATG GCC AGC CTC AGT AGC AGC TTT CTT       292
                             Met Ala Ser Leu Ser Ser Ser Phe Leu
                             -37     -35                     -30

GTG CTC TTT CTC TTA TTT CAG AAC AGC TGC TAC TGT TTC AGG AGT CCC       340
Val Leu Phe Leu Leu Phe Gln Asn Ser Cys Tyr Cys Phe Arg Ser Pro
        -25             -20                 -15

CTC TCT GTC TTT AAG AGG TAT GAG GAA TCT ACC AGA TCA CTT TCC AAT       388
Leu Ser Val Phe Lys Arg Tyr Glu Glu Ser Thr Arg Ser Leu Ser Asn
        -10              -5                   1

GAC TGC TTG GGA ACC ACG CGG CCC GTT ATG TCT CCA GGC TCA TCA GAT       436
Asp Cys Leu Gly Thr Thr Arg Pro Val Met Ser Pro Gly Ser Ser Asp
 5                  10                  15                  20

TAT ACT CTA GAT ATC CGC ATG CCA GGA GTA ACT CCG ACA GAG TCG GAC       484
Tyr Thr Leu Asp Ile Arg Met Pro Gly Val Thr Pro Thr Glu Ser Asp
             25                  30                  35

ACA TAT TTG TGC AAG TCT TAC CGG CTG CCA GTG GAT GAT GAA GCC TAT       532
Thr Tyr Leu Cys Lys Ser Tyr Arg Leu Pro Val Asp Asp Glu Ala Tyr
         40                  45                  50

GTA GTT GAC TTC AGA CCA CAT GCC AAT ATG GAT ACT GCA CAT CAC ATG       580
Val Val Asp Phe Arg Pro His Ala Asn Met Asp Thr Ala His His Met
     55                  60                  65

CTT CTA TTT GGA TGC AAT ATA CCT TCT TCC ACT GAT GAT TAC TGG GAC       628
Leu Leu Phe Gly Cys Asn Ile Pro Ser Ser Thr Asp Asp Tyr Trp Asp
 70                  75                  80

TGT AGT GCG GGA ACT TGC ATG GAC AAA TCC AGT ATA ATG TAT GCC TGG       676
Cys Ser Ala Gly Thr Cys Met Asp Lys Ser Ser Ile Met Tyr Ala Trp
 85                  90                  95                 100

GCA AAG AAT GCA CCA CCC ACC AAA CTT CCA GAA GGA GTT GGC TTT CGT       724
Ala Lys Asn Ala Pro Pro Thr Lys Leu Pro Glu Gly Val Gly Phe Arg
                 105                 110                 115

GTT GGA GGG AAA TCA GGC AGT AGA TAT TTT GTG CTT CAA GTT CAC TAT       772
Val Gly Gly Lys Ser Gly Ser Arg Tyr Phe Val Leu Gln Val His Tyr
             120                 125                 130

GGA AAT GTG AAA GCA TTC CAG GAT AAA CAT AAA GAT TGC ACG GGG GTG       820
Gly Asn Val Lys Ala Phe Gln Asp Lys His Lys Asp Cys Thr Gly Val
         135                 140                 145

ACA GTA CGA GTA ACA CCT GAA AAA CAA CCG CAA ATT GCA GGC ATT TAT       868
Thr Val Arg Val Thr Pro Glu Lys Gln Pro Gln Ile Ala Gly Ile Tyr
 150                 155                 160

CTT TCA ATG TCT GTG GAC ACT GTT ATT CCA CCT GGG GAA GAG GCA GTT       916
Leu Ser Met Ser Val Asp Thr Val Ile Pro Pro Gly Glu Glu Ala Val
165                 170                 175                 180
```

```
AAT TCT GAT ATC GCC TGC CTC TAC AAC AGG CCG ACA ATA CAC CCA TTT      964
Asn Ser Asp Ile Ala Cys Leu Tyr Asn Arg Pro Thr Ile His Pro Phe
            185                 190                 195

GCC TAC AGA GTC CAC ACT CAT CAG TTG GGG CAG GTC GTA AGT GGA TTT     1012
Ala Tyr Arg Val His Thr His Gln Leu Gly Gln Val Val Ser Gly Phe
            200                 205                 210

AGA GTG AGA CAT GGC AAG TGG TCT TTA ATT GGT AGA CAA AGC CCA CAG     1060
Arg Val Arg His Gly Lys Trp Ser Leu Ile Gly Arg Gln Ser Pro Gln
            215                 220                 225

CTG CCA CAG GCA TTT TAC CCT GTA GAG CAT CCA GTA GAG ATT AGC CCT     1108
Leu Pro Gln Ala Phe Tyr Pro Val Glu His Pro Val Glu Ile Ser Pro
        230                 235                 240

GGG GAT ATT ATA GCA ACC AGG TGT CTG TTC ACT GGT AAA GGC AGG ACG     1156
Gly Asp Ile Ile Ala Thr Arg Cys Leu Phe Thr Gly Lys Gly Arg Thr
245                 250                 255                 260

TCA GCA ACA TAT ATT GGT GGC ACA TCT AAC GAT GAA ATG TGT AAT TTA     1204
Ser Ala Thr Tyr Ile Gly Gly Thr Ser Asn Asp Glu Met Cys Asn Leu
            265                 270                 275

TAC ATC ATG TAT TAC ATG GAT GCG GCC CAT GCT ACG TCA TAC ATG ACC     1252
Tyr Ile Met Tyr Tyr Met Asp Ala Ala His Ala Thr Ser Tyr Met Thr
            280                 285                 290

TGT GTA CAG ACG GGT GAA CCA AAG TTA TTT CAA AAC ATC CCT GAG ATT     1300
Cys Val Gln Thr Gly Glu Pro Lys Leu Phe Gln Asn Ile Pro Glu Ile
            295                 300                 305

GCA AAT GTT CCC ATT CCT GTA AGC CCT GAC ATG ATG ATG ATG ATG GGA     1348
Ala Asn Val Pro Ile Pro Val Ser Pro Asp Met Met Met Met Met Gly
        310                 315                 320

CAT GGT CAC CAC CAT ACA GAA GCT GAG CCT GAG AAG AAT ACA GGA CTT     1396
His Gly His His His Thr Glu Ala Glu Pro Glu Lys Asn Thr Gly Leu
325                 330                 335                 340

CAG CAG CCT AAA CGG GAG GAG GAA GAA GTA TTA GAT CAG GGT CTC ATT     1444
Gln Gln Pro Lys Arg Glu Glu Glu Glu Val Leu Asp Gln Gly Leu Ile
                345                 350                 355

ACC TTA GGG GAT AGC GCA GTG TGA TGGAGGAGGA CATGATCCCT ATACCGTTGA    1498
Thr Leu Gly Asp Ser Ala Val  *
            360

AGGGGATGAC CCAATCATTT TAAAGAACGT TCTTTTAAAC ATGAGAGACC ACATCCAGGA   1558

GACATAAATC CACAAATTGT ATAAGTTGTG TGTATACATC ACCCTTTTAT GACAAAGATC   1618

CATAATATAA TACGTTATCA CTGACCCTTC TGCAACATCC TTAATCCAGG ATTTGCTCAC   1678

TCTCCATTGC TGTCATACAG ATGTTCACTT ATGGGCAACA AAATACTTTT CTCCTAATTC   1738

AGGTCCAGTT TTTCTCATTG AAGTGCATCT GGCTCAATTG ACAAATCTAA AATTGATTTA   1798

GGAAATCAGC TTTTTCCCCA TCAAATTGAA GCTGGCCCAA AAGTTACTCT TAAAAGAAGG   1858

TGACAGTCAA GTCTCAACTT TTGCCCACTG AGTTAGTGAT ACCAATTCTG TGTAGGGGAA   1918

TTAAGTAGCT TTTCTTAAAG GGTTGGTTCA CCTTTAAGTC AACTTTTAGT ATGTTATAGA   1978

ATGACTAATT CATAAATAAA TAAATAAAAG CAGCTTTTCA ATTGGTCTTC ATTATTTATT   2038

TTGTATAGTT TTTTTATTAT TTGTCTTTTT CATCTGACTT TTTCCAGCTT TCAAATGGGG   2098

GTCACTGACC CCATCTAAAA AAACAAATGC TCTGTAAGAC TACAAATTTA TTGTTACTGC   2158

TTTTAATTAG TAATGTTTCT ATTCAGGCCC TCCCCTATTC ATATTCAAGC CTTTTATTCC   2218

AATCAGTGCA TGGTTGCTAG GGTAATTGGT ACCCTAGCAA CCAGATCACT AAAACTGCAA   2278

ACTGGAGAAC TGCTGAATAA AAAGCTAAAT AACAAAAAAA ACACAAATAA TAAAAAATGT   2338

AAACCAACTG CAAATTGTCA GAATATCACC CTGTACAATC TACATCACAC TAAAAGTTAA   2398
```

```
TTTAAAGGTG AACAACCCCA TAAGGAAGAC ATACAATTTG TGGATACACA CACTACAGAC    2458

ACTACAACCT AGATGGCTCA TTAAGGAATA TGATTTACAT TTTATTTATT AAAAATGAAA    2518

TGATTTAACT GTTGATTTTG AATTGATTAT GTTGATTCTA ATGTTGAATT GTTATTGGGT    2578

GCTGAAAACT GATCATAGGG TGGAATGTAT AC                                 2610

(2) INFORMATION FOR SEQ ID NO:35:

(i) SEQUENCE CHARACTERISTICS:
        (A) LENGTH: 1032 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1032

(xi) SEQUENCE DESCRIPTION: SEQ ID NO:35:

TCA CTT TCC AAT GAC TGC TTG GGA ACC ACG CGG CCC GTT ATG TCT CCA      48
Ser Leu Ser Asn Asp Cys Leu Gly Thr Thr Arg Pro Val Met Ser Pro
 1               5                  10                  15

GGC TCA TCA GAT TAT ACT CTA GAT ATC CGC ATG CCA GGA GTA ACT CCG      96
Gly Ser Ser Asp Tyr Thr Leu Asp Ile Arg Met Pro Gly Val Thr Pro
             20                  25                  30

ACA GAG TCG GAC ACA TAT TTG TGC AAG TCT TAC CGG CTG CCA GTG GAT     144
Thr Glu Ser Asp Thr Tyr Leu Cys Lys Ser Tyr Arg Leu Pro Val Asp
         35                  40                  45

GAT GAA GCC TAT GTA GTT GAC TTC AGA CCA CAT GCC AAT ATG GAT ACT     192
Asp Glu Ala Tyr Val Val Asp Phe Arg Pro His Ala Asn Met Asp Thr
 50                  55                  60

GCA CAT CAC ATG CTT CTA TTT GGA TGC AAT ATA CCT TCT TCC ACT GAT     240
Ala His His Met Leu Leu Phe Gly Cys Asn Ile Pro Ser Ser Thr Asp
 65                  70                  75                  80

GAT TAC TGG GAC TGT AGT GCG GGA ACT TGC ATG GAC AAA TCC AGT ATA     288
Asp Tyr Trp Asp Cys Ser Ala Gly Thr Cys Met Asp Lys Ser Ser Ile
             85                  90                  95

ATG TAT GCC TGG GCA AAG AAT GCA CCA CCC ACC AAA CTT CCA GAA GGA     336
Met Tyr Ala Trp Ala Lys Asn Ala Pro Pro Thr Lys Leu Pro Glu Gly
            100                 105                 110

GTT GGC TTT CGT GTT GGA GGG AAA TCA GGC AGT AGA TAT TTT GTG CTT     384
Val Gly Phe Arg Val Gly Gly Lys Ser Gly Ser Arg Tyr Phe Val Leu
        115                 120                 125

CAA GTT CAC TAT GGA AAT GTG AAA GCA TTC CAG GAT AAA CAT AAA GAT     432
Gln Val His Tyr Gly Asn Val Lys Ala Phe Gln Asp Lys His Lys Asp
130                 135                 140

TGC ACG GGG GTG ACA GTA CGA GTA ACA CCT GAA AAA CAA CCG CAA ATT     480
Cys Thr Gly Val Thr Val Arg Val Thr Pro Glu Lys Gln Pro Gln Ile
145                 150                 155                 160

GCA GGC ATT TAT CTT TCA ATG TCT GTG GAC ACT GTT ATT CCA CCT GGG     528
Ala Gly Ile Tyr Leu Ser Met Ser Val Asp Thr Val Ile Pro Pro Gly
                165                 170                 175

GAA GAG GCA GTT AAT TCT GAT ATC GCC TGC CTC TAC AAC AGG CCG ACA     576
Glu Glu Ala Val Asn Ser Asp Ile Ala Cys Leu Tyr Asn Arg Pro Thr
            180                 185                 190

ATA CAC CCA TTT GCC TAC AGA GTC CAC ACT CAT CAG TTG GGG CAG GTC     624
Ile His Pro Phe Ala Tyr Arg Val His Thr His Gln Leu Gly Gln Val
        195                 200                 205

GTA AGT GGA TTT AGA GTG AGA CAT GGC AAG TGG TCT TTA ATT GGT AGA     672
Val Ser Gly Phe Arg Val Arg His Gly Lys Trp Ser Leu Ile Gly Arg
```

```
     210                 215                 220
CAA AGC CCA CAG CTG CCA CAG GCA TTT TAC CCT GTA GAG CAT CCA GTA           720
Gln Ser Pro Gln Leu Pro Gln Ala Phe Tyr Pro Val Glu His Pro Val
225                 230                 235                 240

GAG ATT AGC CCT GGG GAT ATT ATA GCA ACC AGG TGT CTG TTC ACT GGT           768
Glu Ile Ser Pro Gly Asp Ile Ile Ala Thr Arg Cys Leu Phe Thr Gly
                    245                 250                 255

AAA GGC AGG ACG TCA GCA ACA TAT ATT GGT GGC ACA TCT AAC GAT GAA           816
Lys Gly Arg Thr Ser Ala Thr Tyr Ile Gly Gly Thr Ser Asn Asp Glu
                260                 265                 270

ATG TGT AAT TTA TAC ATC ATG TAT TAC ATG GAT GCC GCC CAT GCT ACG           864
Met Cys Asn Leu Tyr Ile Met Tyr Tyr Met Asp Ala Ala His Ala Thr
            275                 280                 285

TCA TAC ATG ACC TGT GTA CAG ACG GGT GAA CCA AAG TTA TTT CAA AAC           912
Ser Tyr Met Thr Cys Val Gln Thr Gly Glu Pro Lys Leu Phe Gln Asn
        290                 295                 300

ATC CCT GAG ATT GCA AAT GTT CCC ATT CCT GTA AGC CCT GAC ATG ATG           960
Ile Pro Glu Ile Ala Asn Val Pro Ile Pro Val Ser Pro Asp Met Met
305                 310                 315                 320

ATG ATG ATG GGA CAT GGT CAC CAC CAT ACA GAA GCT GAG CCT GAG AAG          1008
Met Met Met Gly His Gly His His His Thr Glu Ala Glu Pro Glu Lys
                    325                 330                 335

AAT ACA GGA CTT CAG CAG CCT AAA                                          1032
Asn Thr Gly Leu Gln Gln Pro Lys
                340
```

(2) INFORMATION FOR SEQ ID NO:36:

(i) SEQUENCE CHARACTERISTICS:
        (A) LENGTH: 1089 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1089

(xi) SEQUENCE DESCRIPTION: SEQ ID NO:36:

```
TCA CTT TCC AAT GAC TGC TTG GGA ACC ACG CGG CCC GTT ATG TCT CCA            48
Ser Leu Ser Asn Asp Cys Leu Gly Thr Thr Arg Pro Val Met Ser Pro
1                   5                  10                  15

GGC TCA TCA GAT TAT ACT CTA GAT ATC CGC ATG CCA GGA GTA ACT CCG            96
Gly Ser Ser Asp Tyr Thr Leu Asp Ile Arg Met Pro Gly Val Thr Pro
                    20                  25                  30

ACA GAG TCG GAC ACA TAT TTG TGC AAG TCT TAC CGG CTG CCA GTG GAT           144
Thr Glu Ser Asp Thr Tyr Leu Cys Lys Ser Tyr Arg Leu Pro Val Asp
                35                  40                  45

GAT GAA GCC TAT GTA GTT GAC TTC AGA CCA CAT GCC AAT ATG GAT ACT           192
Asp Glu Ala Tyr Val Val Asp Phe Arg Pro His Ala Asn Met Asp Thr
            50                  55                  60

GCA CAT CAC ATG CTT CTA TTT GGA TGC AAT ATA CCT TCT TCC ACT GAT           240
Ala His His Met Leu Leu Phe Gly Cys Asn Ile Pro Ser Ser Thr Asp
65                  70                  75                  80

GAT TAC TGG GAC TGT AGT GCG GGA ACT TGC ATG GAC AAA TCC AGT ATA           288
Asp Tyr Trp Asp Cys Ser Ala Gly Thr Cys Met Asp Lys Ser Ser Ile
                    85                  90                  95

ATG TAT GCC TGG GCA AAG AAT GCA CCA CCC ACC AAA CTT CCA GAA GGA           336
Met Tyr Ala Trp Ala Lys Asn Ala Pro Pro Thr Lys Leu Pro Glu Gly
                    100                 105                 110
```

```
GTT GGC TTT CGT GTT GGA GGG AAA TCA GGC AGT AGA TAT TTT GTG CTT      384
Val Gly Phe Arg Val Gly Gly Lys Ser Gly Ser Arg Tyr Phe Val Leu
            115                 120                 125

CAA GTT CAC TAT GGA AAT GTG AAA GCA TTC CAG GAT AAA CAT AAA GAT      432
Gln Val His Tyr Gly Asn Val Lys Ala Phe Gln Asp Lys His Lys Asp
        130                 135                 140

TGC ACG GGG GTG ACA GTA CGA GTA ACA CCT GAA AAA CAA CCG CAA ATT      480
Cys Thr Gly Val Thr Val Arg Val Thr Pro Glu Lys Gln Pro Gln Ile
145                 150                 155                 160

GCA GGC ATT TAT CTT TCA ATG TCT GTG GAC ACT GTT ATT CCA CCT GGG      528
Ala Gly Ile Tyr Leu Ser Met Ser Val Asp Thr Val Ile Pro Pro Gly
                165                 170                 175

GAA GAG GCA GTT AAT TCT GAT ATC GCC TGC CTC TAC AAC AGG CCG ACA      576
Glu Glu Ala Val Asn Ser Asp Ile Ala Cys Leu Tyr Asn Arg Pro Thr
            180                 185                 190

ATA CAC CCA TTT GCC TAC AGA GTC CAC ACT CAT CAG TTG GGG CAG GTC      624
Ile His Pro Phe Ala Tyr Arg Val His Thr His Gln Leu Gly Gln Val
        195                 200                 205

GTA AGT GGA TTT AGA GTG AGA CAT GGC AAG TGG TCT TTA ATT GGT AGA      672
Val Ser Gly Phe Arg Val Arg His Gly Lys Trp Ser Leu Ile Gly Arg
210                 215                 220

CAA AGC CCA CAG CTG CCA CAG GCA TTT TAC CCT GTA GAG CAT CCA GTA      720
Gln Ser Pro Gln Leu Pro Gln Ala Phe Tyr Pro Val Glu His Pro Val
225                 230                 235                 240

GAG ATT AGC CCT GGG GAT ATT ATA GCA ACC AGG TGT CTG TTC ACT GGT      768
Glu Ile Ser Pro Gly Asp Ile Ile Ala Thr Arg Cys Leu Phe Thr Gly
                245                 250                 255

AAA GGC AGG ACG TCA GCA ACA TAT ATT GGT GGC ACA TCT AAC GAT GAA      816
Lys Gly Arg Thr Ser Ala Thr Tyr Ile Gly Gly Thr Ser Asn Asp Glu
            260                 265                 270

ATG TGT AAT TTA TAC ATC ATG TAT TAC ATG GAT GCG GCC CAT GCT ACG      864
Met Cys Asn Leu Tyr Ile Met Tyr Tyr Met Asp Ala Ala His Ala Thr
        275                 280                 285

TCA TAC ATG ACC TGT GTA CAG ACG GGT GAA CCA AAG TTA TTT CAA AAC      912
Ser Tyr Met Thr Cys Val Gln Thr Gly Glu Pro Lys Leu Phe Gln Asn
290                 295                 300

ATC CCT GAG ATT GCA AAT GTT CCC ATT CCT GTA AGC CCT GAC ATG ATG      960
Ile Pro Glu Ile Ala Asn Val Pro Ile Pro Val Ser Pro Asp Met Met
305                 310                 315                 320

ATG ATG ATG GGA CAT GGT CAC CAC CAT ACA GAA GCT GAG CCT GAG AAG     1008
Met Met Met Gly His Gly His His His Thr Glu Ala Glu Pro Glu Lys
                325                 330                 335

AAT ACA GGA CTT CAG CAG CCT AAA CGG GAG GAG GAA GAA GTA TTA GAT     1056
Asn Thr Gly Leu Gln Gln Pro Lys Arg Glu Glu Glu Glu Val Leu Asp
            340                 345                 350

CAG GGT CTC ATT ACC TTA GGG GAT AGC GCA GTG                         1089
Gln Gly Leu Ile Thr Leu Gly Asp Ser Ala Val
        355                 360
```

(2) INFORMATION FOR SEQ ID NO:37:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1200

(xi) SEQUENCE DESCRIPTION: SEQ ID NO:37:

| | | | | | | | | | | | | | | | | |
|---|---|---|---|---|---|---|---|---|---|---|---|---|---|---|---|---|
| ATG | GCC | AGC | CTC | AGT | AGC | AGC | TTT | CTT | GTG | CTC | TTT | CTC | TTA | TTT | CAG | 48 |
| Met | Ala | Ser | Leu | Ser | Ser | Ser | Phe | Leu | Val | Leu | Phe | Leu | Leu | Phe | Gln | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| AAC | AGC | TGC | TAC | TGT | TTC | AGG | AGT | CCC | CTC | TCT | GTC | TTT | AAG | AGG | TAT | 96 |
| Asn | Ser | Cys | Tyr | Cys | Phe | Arg | Ser | Pro | Leu | Ser | Val | Phe | Lys | Arg | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| GAG | GAA | TCT | ACC | AGA | TCA | CTT | TCC | AAT | GAC | TGC | TTG | GGA | ACC | ACG | CGG | 144 |
| Glu | Glu | Ser | Thr | Arg | Ser | Leu | Ser | Asn | Asp | Cys | Leu | Gly | Thr | Thr | Arg | |
| | | 35 | | | | | 40 | | | | | 45 | | | | |

| | | | | | | | | | | | | | | | | |
|---|---|---|---|---|---|---|---|---|---|---|---|---|---|---|---|---|
| CCC | GTT | ATG | TCT | CCA | GGC | TCA | TCA | GAT | TAT | ACT | CTA | GAT | ATC | CGC | ATG | 192 |
| Pro | Val | Met | Ser | Pro | Gly | Ser | Ser | Asp | Tyr | Thr | Leu | Asp | Ile | Arg | Met | |
| | 50 | | | | | 55 | | | | | 60 | | | | | |

| | | | | | | | | | | | | | | | | |
|---|---|---|---|---|---|---|---|---|---|---|---|---|---|---|---|---|
| CCA | GGA | GTA | ACT | CCG | ACA | GAG | TCG | GAC | ACA | TAT | TTG | TGC | AAG | TCT | TAC | 240 |
| Pro | Gly | Val | Thr | Pro | Thr | Glu | Ser | Asp | Thr | Tyr | Leu | Cys | Lys | Ser | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| CGG | CTG | CCA | GTG | GAT | GAT | GAA | GCC | TAT | GTA | GTT | GAC | TTC | AGA | CCA | CAT | 288 |
| Arg | Leu | Pro | Val | Asp | Asp | Glu | Ala | Tyr | Val | Val | Asp | Phe | Arg | Pro | His | |
| | | | | 85 | | | | | 90 | | | | | 95 | | |

| | | | | | | | | | | | | | | | | |
|---|---|---|---|---|---|---|---|---|---|---|---|---|---|---|---|---|
| GCC | AAT | ATG | GAT | ACT | GCA | CAT | CAC | ATG | CTT | CTA | TTT | GGA | TGC | AAT | ATA | 336 |
| Ala | Asn | Met | Asp | Thr | Ala | His | His | Met | Leu | Leu | Phe | Gly | Cys | Asn | Ile | |
| | | | 100 | | | | | 105 | | | | | 110 | | | |

| | | | | | | | | | | | | | | | | |
|---|---|---|---|---|---|---|---|---|---|---|---|---|---|---|---|---|
| CCT | TCT | TCC | ACT | GAT | GAT | TAC | TGG | GAC | TGT | AGT | GCG | GGA | ACT | TGC | ATG | 384 |
| Pro | Ser | Ser | Thr | Asp | Asp | Tyr | Trp | Asp | Cys | Ser | Ala | Gly | Thr | Cys | Met | |
| | | 115 | | | | | 120 | | | | | 125 | | | | |

| | | | | | | | | | | | | | | | | |
|---|---|---|---|---|---|---|---|---|---|---|---|---|---|---|---|---|
| GAC | AAA | TCC | AGT | ATA | ATG | TAT | GCC | TGG | GCA | AAG | AAT | GCA | CCA | CCC | ACC | 432 |
| Asp | Lys | Ser | Ser | Ile | Met | Tyr | Ala | Trp | Ala | Lys | Asn | Ala | Pro | Pro | Thr | |
| | 130 | | | | | 135 | | | | | 140 | | | | | |

| | | | | | | | | | | | | | | | | |
|---|---|---|---|---|---|---|---|---|---|---|---|---|---|---|---|---|
| AAA | CTT | CCA | GAA | GGA | GTT | GGC | TTT | CGT | GTT | GGA | GGG | AAA | TCA | GGC | AGT | 480 |
| Lys | Leu | Pro | Glu | Gly | Val | Gly | Phe | Arg | Val | Gly | Gly | Lys | Ser | Gly | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| AGA | TAT | TTT | GTG | CTT | CAA | GTT | CAC | TAT | GGA | AAT | GTG | AAA | GCA | TTC | CAG | 528 |
| Arg | Tyr | Phe | Val | Leu | Gln | Val | His | Tyr | Gly | Asn | Val | Lys | Ala | Phe | Gln | |
| | | | | 165 | | | | | 170 | | | | | 175 | | |

| | | | | | | | | | | | | | | | | |
|---|---|---|---|---|---|---|---|---|---|---|---|---|---|---|---|---|
| GAT | AAA | CAT | AAA | GAT | TGC | ACG | GGG | GTG | ACA | GTA | CGA | GTA | ACA | CCT | GAA | 576 |
| Asp | Lys | His | Lys | Asp | Cys | Thr | Gly | Val | Thr | Val | Arg | Val | Thr | Pro | Glu | |
| | | | 180 | | | | | 185 | | | | | 190 | | | |

| | | | | | | | | | | | | | | | | |
|---|---|---|---|---|---|---|---|---|---|---|---|---|---|---|---|---|
| AAA | CAA | CCG | CAA | ATT | GCA | GGC | ATT | TAT | CTT | TCA | ATG | TCT | GTG | GAC | ACT | 624 |
| Lys | Gln | Pro | Gln | Ile | Ala | Gly | Ile | Tyr | Leu | Ser | Met | Ser | Val | Asp | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| GTT | ATT | CCA | CCT | GGG | GAA | GAG | GCA | GTT | AAT | TCT | GAT | ATC | GCC | TGC | CTC | 672 |
| Val | Ile | Pro | Pro | Gly | Glu | Glu | Ala | Val | Asn | Ser | Asp | Ile | Ala | Cys | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| TAC | AAC | AGG | CCG | ACA | ATA | CAC | CCA | TTT | GCC | TAC | AGA | GTC | CAC | ACT | CAT | 720 |
| Tyr | Asn | Arg | Pro | Thr | Ile | His | Pro | Phe | Ala | Tyr | Arg | Val | His | Thr | His | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| CAG | TTG | GGG | CAG | GTC | GTA | AGT | GGA | TTT | AGA | GTG | AGA | CAT | GGC | AAG | TGG | 768 |
| Gln | Leu | Gly | Gln | Val | Val | Ser | Gly | Phe | Arg | Val | Arg | His | Gly | Lys | Trp | |
| | | | | 245 | | | | | 250 | | | | | 255 | | |

| | | | | | | | | | | | | | | | | |
|---|---|---|---|---|---|---|---|---|---|---|---|---|---|---|---|---|
| TCT | TTA | ATT | GGT | AGA | CAA | AGC | CCA | CAG | CTG | CCA | CAG | GCA | TTT | TAC | CCT | 816 |
| Ser | Leu | Ile | Gly | Arg | Gln | Ser | Pro | Gln | Leu | Pro | Gln | Ala | Phe | Tyr | Pro | |
| | | | 260 | | | | | 265 | | | | | 270 | | | |

| | | | | | | | | | | | | | | | | |
|---|---|---|---|---|---|---|---|---|---|---|---|---|---|---|---|---|
| GTA | GAG | CAT | CCA | GTA | GAG | ATT | AGC | CCT | GGG | GAT | ATT | ATA | GCA | ACC | AGG | 864 |
| Val | Glu | His | Pro | Val | Glu | Ile | Ser | Pro | Gly | Asp | Ile | Ile | Ala | Thr | Arg | |
| | | 275 | | | | | 280 | | | | | 285 | | | | |

| | | | | | | | | | | | | | | | | |
|---|---|---|---|---|---|---|---|---|---|---|---|---|---|---|---|---|
| TGT | CTG | TTC | ACT | GGT | AAA | GGC | AGG | ACG | TCA | GCA | ACA | TAT | ATT | GGT | GGC | 912 |
| Cys | Leu | Phe | Thr | Gly | Lys | Gly | Arg | Thr | Ser | Ala | Thr | Tyr | Ile | Gly | Gly | |
| | 290 | | | | | 295 | | | | | 300 | | | | | |

| | | | | | | | | | | | | | | | | |
|---|---|---|---|---|---|---|---|---|---|---|---|---|---|---|---|---|
| ACA | TCT | AAC | GAT | GAA | ATG | TGT | AAT | TTA | TAC | ATC | ATG | TAT | TAC | ATG | GAT | 960 |

```
Thr Ser Asn Asp Glu Met Cys Asn Leu Tyr Ile Met Tyr Tyr Met Asp
305                 310                 315                 320

GCG GCC CAT GCT ACG TCA TAC ATG ACC TGT GTA CAG ACG GGT GAA CCA      1008
Ala Ala His Ala Thr Ser Tyr Met Thr Cys Val Gln Thr Gly Glu Pro
            325                 330                 335

AAG TTA TTT CAA AAC ATC CCT GAG ATT GCA AAT GTT CCC ATT CCT GTA      1056
Lys Leu Phe Gln Asn Ile Pro Glu Ile Ala Asn Val Pro Ile Pro Val
            340                 345                 350

AGC CCT GAC ATG ATG ATG ATG ATG GGA CAT GGT CAC CAC CAT ACA GAA      1104
Ser Pro Asp Met Met Met Met Met Gly His Gly His His His Thr Glu
            355                 360                 365

GCT GAG CCT GAG AAG AAT ACA GGA CTT CAG CAG CCT AAA CGG GAG GAG      1152
Ala Glu Pro Glu Lys Asn Thr Gly Leu Gln Gln Pro Lys Arg Glu Glu
    370                 375                 380

GAA GAA GTA TTA GAT CAG GGT CTC ATT ACC TTA GGG GAT AGC GCA GTG      1200
Glu Glu Val Leu Asp Gln Gly Leu Ile Thr Leu Gly Asp Ser Ala Val
385                 390                 395                 400
```

(2) INFORMATION FOR SEQ ID NO:38:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:38:

```
Val Thr Pro Glu Lys
1               5
```

(2) INFORMATION FOR SEQ ID NO:39:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:39:

```
Ala Phe Gln Asp Lys
1               5
```

(2) INFORMATION FOR SEQ ID NO:40:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:40:

```
Met Gly His Gly His His His Thr Glu Ala Glu Pro Glu Lys
1               5                   10
```

(2) INFORMATION FOR SEQ ID NO:41:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

Met Met Gly His Gly His His His Thr Glu Ala Glu Pro Glu Lys
1               5                   10                  15

(2) INFORMATION FOR SEQ ID NO:42:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:42:

Asn Thr Gly Leu Gln Gln Pro Lys
1               5

(2) INFORMATION FOR SEQ ID NO:43:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:43:

Leu Pro Glu Gly Val Gly Phe Arg
1               5

(2) INFORMATION FOR SEQ ID NO:44:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:44:

Val His Thr His Gln Leu Gly Gln Val Val Ser Gly Phe Arg
1               5                   10

(2) INFORMATION FOR SEQ ID NO:45:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:45:

Pro Val Met Ser Pro Gly Ser Ser Asp Tyr Thr Leu Asp Ile Arg
1               5                   10                  15

(2) INFORMATION FOR SEQ ID NO:46:

(i) SEQUENCE CHARACTERISTICS:
            (A) LENGTH: 6 amino acids
            (B) TYPE: amino acid
            (C) STRANDEDNESS: single (D) TOPOLOGY: linear (ii) MOLECULE TYPE: protein (xi) SEQUENCE DESCRIPTION: SEQ ID NO:46:

Trp Ser Leu Ile Gly Arg
1               5

(2) INFORMATION FOR SEQ ID NO:47:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

Leu Pro Val Asp Asp Glu Ala Tyr Val Val Asp Phe Arg Pro
1               5                   10

(2) INFORMATION FOR SEQ ID NO:48:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

Ala Phe Tyr Pro Val Glu His Pro Val Glu Ile Ser Pro Gly Asp Ile
1               5                   10                  15

Ile Ala Thr Arg
            20

(2) INFORMATION FOR SEQ ID NO:49:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

Gln Ser Pro Gln Leu Pro Gln Ala Phe Tyr Pro Val Glu His Pro Val
1               5                   10                  15

Glu Ile Ser Pro Gly Xaa Ile
            20

(2) INFORMATION FOR SEQ ID NO:50:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:50:

Met Pro Gly Val Thr Pro Thr Glu Ser Asp Thr Tyr Leu Xaa Lys
1               5                   10                  15

(2) INFORMATION FOR SEQ ID NO:51:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:51:

Ser Leu Ser Asn Asp Xaa Leu Gly Thr Thr Arg Pro Val Met Ser
1               5                   10                  15

(2) INFORMATION FOR SEQ ID NO:52:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:52:

Asp Asp Glu Ala Tyr Val
1               5

(2) INFORMATION FOR SEQ ID NO:53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 3
        (D) OTHER INFORMATION: /note= "Nucleotide 3 is N wherein N
            = U or C."

(ix) FEATURE:
        (A) NAME/KEY: misc_feature
        (B) LOCATION: 6
        (D) OTHER INFORMATION: /note= "Nucleotide 6 is N wherein N
            = U or C."

(ix) FEATURE:
        (A) NAME/KEY: misc_feature
        (B) LOCATION: 9
        (D) OTHER INFORMATION: /note= "Nucleotide 9 is N wherein N
            = A or G."

(ix) FEATURE:
        (A) NAME/KEY: misc_feature
        (B) LOCATION: 12
        (D) OTHER INFORMATION: /note= "Nucleotide 12 is N wherein
            N = U, C, A, or G."

(ix) FEATURE:
        (A) NAME/KEY: misc_feature
        (B) LOCATION: 15
        (D) OTHER INFORMATION: /note= "Nucleotide 15 is N wherein
            N = U or C."

(ix) FEATURE:
        (A) NAME/KEY: misc_feature
        (B) LOCATION: 18
        (D) OTHER INFORMATION: /note= "Nucleotide 18 is N wherein
            N = U, C, A, or G."

(xi) SEQUENCE DESCRIPTION: SEQ ID NO:53:

GANGANGANG CNUANGUN                                                    18

(2) INFORMATION FOR SEQ ID NO:54:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 3
        (D) OTHER INFORMATION: /note= "Nucleotide 3 is N wherein N
            = A or G."

(ix) FEATURE:
        (A) NAME/KEY: misc_feature
        (B) LOCATION: 6
        (D) OTHER INFORMATION: /note= "Nucleotide 6 is N wherein N
            = A or G."

(ix) FEATURE:
        (A) NAME/KEY: misc_feature
        (B) LOCATION: 9
        (D) OTHER INFORMATION: /note= "Nucleotide 9 is N wherein N
            = T or C."

(ix) FEATURE:
        (A) NAME/KEY: misc_feature
        (B) LOCATION: 12
        (D) OTHER INFORMATION: /note= "Nucleotide 12 is N wherein
            N = A or C."

(ix) FEATURE:
        (A) NAME/KEY: misc_feature
        (B) LOCATION: 15
        (D) OTHER INFORMATION: /note= "Nucleotide 15 is N wherein
            N = A or G."

(xi) SEQUENCE DESCRIPTION: SEQ ID NO:54:

CTNCTNCTNC GNATNCA                                                     17

(2) INFORMATION FOR SEQ ID NO:55:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 3
        (D) OTHER INFORMATION: /note= "Nucleotide 3 is N wherein N
            = A or G."

(ix) FEATURE:
        (A) NAME/KEY: misc_feature
        (B) LOCATION: 6
        (D) OTHER INFORMATION: /note= "Nucleotide 6 is N wherein N
            = A or G."

(ix) FEATURE:
        (A) NAME/KEY: misc_feature
        (B) LOCATION: 9
        (D) OTHER INFORMATION: /note= "Nucleotide 9 is N wherein N
            = T or C."

(ix) FEATURE:

(A) NAME/KEY: misc_feature
        (B) LOCATION: 12
        (D) OTHER INFORMATION: /note= "Nucleotide 12 is N wherein
            N = T or C."

(ix) FEATURE:
        (A) NAME/KEY: misc_feature
        (B) LOCATION: 15
        (D) OTHER INFORMATION: /note= "Nucleotide 15 is N wherein
            N = A or G."

(xi) SEQUENCE DESCRIPTION: SEQ ID NO:55:

CTNCTNCTNC GNATNCA                                                    17

(2) INFORMATION FOR SEQ ID NO:56:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:56:

Met Met Gly His Gly His
1               5

(2) INFORMATION FOR SEQ ID NO:57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 9
        (D) OTHER INFORMATION: /note= "Nucleotide 9 is N wherein N
            = U, C, A, or G."

(ix) FEATURE:
        (A) NAME/KEY: misc_feature
        (B) LOCATION: 12
        (D) OTHER INFORMATION: /note= "Nucleotide 12 is N wherein
            N = U or C."

(ix) FEATURE:
        (A) NAME/KEY: misc_feature
        (B) LOCATION: 15
        (D) OTHER INFORMATION: /note= "Nucleotide 15 is N wherein
            N = U, C, A, or G."

(ix) FEATURE:
        (A) NAME/KEY: misc_feature
        (B) LOCATION: 18
        (D) OTHER INFORMATION: /note= "Nucleotide 18 is N wherein
            N = U or C."

(xi) SEQUENCE DESCRIPTION: SEQ ID NO:57:

AUGAUGGGNC ANGGNCAN                                                   18

(2) INFORMATION FOR SEQ ID NO:58:

(i) SEQUENCE CHARACTERISTICS:
        (A) LENGTH: 17 base pairs
        (B) TYPE: nucleic acid
        (C) STRANDEDNESS: single
        (D) TOPOLOGY: linear

```
       (ii) MOLECULE TYPE: DNA (genomic)

(ix) FEATURE:
            (A) NAME/KEY: misc_feature
            (B) LOCATION: 9
            (D) OTHER INFORMATION: /note= "Nucleotide 9 is N wherein N
                = A, G, T, or C."

(ix) FEATURE:
            (A) NAME/KEY: misc_feature
            (B) LOCATION: 12
            (D) OTHER INFORMATION: /note= "Nucleotide 12 is N wherein
                N = A or G."

(ix) FEATURE:
            (A) NAME/KEY: misc_feature
            (B) LOCATION: 15
            (D) OTHER INFORMATION: /note= "Nucleotide 15 is N wherein
                N = A, G, T, or C."

(xi) SEQUENCE DESCRIPTION: SEQ ID NO:58:

TACTACCCNG TNCCNGT                                                      17

(2) INFORMATION FOR SEQ ID NO:59:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:59:

GTCATTGGAA AGTGACATGA ATTCTTCCTC ATACCTCTT                               39

(2) INFORMATION FOR SEQ ID NO:60:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:60:

GTCACCACCA TACAGAAGCT GAGCCTGAGA AGAATACAGG ACTTCAGCAG CCTAAATGAG        60

(2) INFORMATION FOR SEQ ID NO:61:

(i) SEQUENCE CHARACTERISTICS:
            (A) LENGTH: 59 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:61:

GTGGTATGTC TTCGACTCGG ACTCTTCTTA TGTCCTGAAG TCGTCGGATT TACTCAGCT         59

(2) INFORMATION FOR SEQ ID NO:62:

(i) SEQUENCE CHARACTERISTICS:
            (A) LENGTH: 3315 base pairs
            (B) TYPE: nucleic acid
            (C) STRANDEDNESS: single
            (D) TOPOLOGY: linear (ii) MOLECULE TYPE: protein
```

(ix) FEATURE:
    (A) NAME/KEY: CDS
    (B) LOCATION: 157..2784

(ix) FEATURE:
    (A) NAME/KEY: mat_peptide
    (B) LOCATION: 274..2784

(ix) FEATURE:
    (A) NAME/KEY: sig_peptide
    (B) LOCATION: 214..271

(xi) SEQUENCE DESCRIPTION: SEQ ID NO:62:

```
GGGGGGCCCT CAAGAAGATC GTATCCCAAC AAGGATGTGT ATTTCTGGCT ACCTGTGGGG      60

CAAGCACTAA TGGAGTAGGG GGATTGATCC AGCTTCCTAT TACCAGGATT ACAACCCTGC     120

CTTTAATTTC TCCTGAAGTA AGGCACAGAC CATATT ATG GAT ATG GCC AGC CTC      174
                                         Met Asp Met Ala Ser Leu
                                         -39             -35

ATT AGC AGC TTG CTT GTG CTC TTT CTC ATA TTT CAG AAC AGC TGT TAC      222
Ile Ser Ser Leu Leu Val Leu Phe Leu Ile Phe Gln Asn Ser Cys Tyr
        -30                 -25                 -20

TGT TTC AGA AGT CCC CTC TCT GTC TTT AAG AGG TAT GAG GAA TCA ACC      270
Cys Phe Arg Ser Pro Leu Ser Val Phe Lys Arg Tyr Glu Glu Ser Thr
        -15                 -10                  -5

AGA TCA CTT TCC AAT GAC TGC TTG GGA ACC ACA CGG CCC GTT ATG TCT      318
Arg Ser Leu Ser Asn Asp Cys Leu Gly Thr Thr Arg Pro Val Met Ser
  1               5                  10                  15

CCA GGC TCA TCA GAT TAT ACT TTA GAT ATC CGA ATG CCA GGA GTA ACT      366
Pro Gly Ser Ser Asp Tyr Thr Leu Asp Ile Arg Met Pro Gly Val Thr
                 20                  25                  30

CCG ACA GAG TCG GAC ACG TAT CTT TGC AAG TCT TAC CGG CTG CCA GTG      414
Pro Thr Glu Ser Asp Thr Tyr Leu Cys Lys Ser Tyr Arg Leu Pro Val
                 35                  40                  45

GAT GAT GAA GCC TAC GTA GTT GAC TAC AGA CCA CAT GCC AAT ATG GAT      462
Asp Asp Glu Ala Tyr Val Val Asp Tyr Arg Pro His Ala Asn Met Asp
             50                  55                  60

ACT GCA CAT CAC ATG CTC CTA TTT GGA TGC AAT GTG CCT TCT TCC ACT      510
Thr Ala His His Met Leu Leu Phe Gly Cys Asn Val Pro Ser Ser Thr
         65                  70                  75

GAT GAT TAC TGG GAC TGC AGT GCA GGA ACT TGT AAT GAC AAA TCT AGT      558
Asp Asp Tyr Trp Asp Cys Ser Ala Gly Thr Cys Asn Asp Lys Ser Ser
 80                  85                  90                  95

ATA ATG TAT GCC TGG GCA AAG AAT GCA CCA CCC ACC AAA CTA CCA GAA      606
Ile Met Tyr Ala Trp Ala Lys Asn Ala Pro Pro Thr Lys Leu Pro Glu
                100                 105                 110

GGA GTT GGA TTT CAA GTT GGA GGG AAA TCG GGC AGT AGA TAT TTT GTT      654
Gly Val Gly Phe Gln Val Gly Gly Lys Ser Gly Ser Arg Tyr Phe Val
            115                 120                 125

CTT CAA GTT CAC TAT GGT GAT GTG AAA GCA TTC CAG GAT AAA CAT AAA      702
Leu Gln Val His Tyr Gly Asp Val Lys Ala Phe Gln Asp Lys His Lys
            130                 135                 140

GAT TGC ACA GGG GTG ACT GTA CGG ATA ACA CCT GAA AAA CAA CCA TTA      750
Asp Cys Thr Gly Val Thr Val Arg Ile Thr Pro Glu Lys Gln Pro Leu
    145                 150                 155

ATT GCA GGC ATT TAT CTT TCA ATG TCT CTC AAC ACT GTT GTT CCA CCT      798
Ile Ala Gly Ile Tyr Leu Ser Met Ser Leu Asn Thr Val Val Pro Pro
160                 165                 170                 175

GGG CAA GAG GTA GTT AAT TCT GAT ATT GCC TGC CTC TAC AAC AGA CCA      846
Gly Gln Glu Val Val Asn Ser Asp Ile Ala Cys Leu Tyr Asn Arg Pro
                180                 185                 190
```

| | |
|---|---|
| ACG ATA CAC CCA TTT GCC TAC AGA GTC CAT ACT CAT CAG TTA GGG CAG<br>Thr Ile His Pro Phe Ala Tyr Arg Val His Thr His Gln Leu Gly Gln<br>              195                           200                      205 | 894 |
| GTG GTG AGC GGC TTT AGA GTC AGA CAT GGC AAA TGG ACT TTA ATT GGC<br>Val Val Ser Gly Phe Arg Val Arg His Gly Lys Trp Thr Leu Ile Gly<br>          210                           215                        220 | 942 |
| AGA CAA AGC CCA CAG CTG CCA CAG GCG TTT TAC CCT GTA GAG CAT CCA<br>Arg Gln Ser Pro Gln Leu Pro Gln Ala Phe Tyr Pro Val Glu His Pro<br>225                           230                        235 | 990 |
| TTA GAG ATT AGC CCT GGA GAT ATT ATA GCA ACC AGG TGT CTG TTC ACT<br>Leu Glu Ile Ser Pro Gly Asp Ile Ile Ala Thr Arg Cys Leu Phe Thr<br>240                       245                     250                    255 | 1038 |
| GGT AAA GGA AGG ATG TCG GCG ACA TAT ATT GGG GGC ACA GCT AAA GAT<br>Gly Lys Gly Arg Met Ser Ala Thr Tyr Ile Gly Gly Thr Ala Lys Asp<br>                    260                        265                        270 | 1086 |
| GAA ATG TGT AAT TTA TAC ATC ATG TAT TAC ATG GAT GCT GCC CAT GCT<br>Glu Met Cys Asn Leu Tyr Ile Met Tyr Tyr Met Asp Ala Ala His Ala<br>              275                           280                        285 | 1134 |
| ACT TCA TAC ATG ACC TGT GTA CAG ACA GGT AAC CCA AAG CTA TTT GAA<br>Thr Ser Tyr Met Thr Cys Val Gln Thr Gly Asn Pro Lys Leu Phe Glu<br>                    290                        295                    300 | 1182 |
| AAC ATC CCT GAG ATT GCA AAT GTT CCG ATT CCT GTA AGC CCT GAC ATG<br>Asn Ile Pro Glu Ile Ala Asn Val Pro Ile Pro Val Ser Pro Asp Met<br>305                           310                     315 | 1230 |
| ATG ATG ATG ATG ATG ATG GGA CAT GGT CAC CAC CAT ACA GAA GCT GAG<br>Met Met Met Met Met Met Gly His Gly His His His Thr Glu Ala Glu<br>320                         325                        330                    335 | 1278 |
| GCT GAG ACG AAT ACA GCA CTT CAG CAG CCT AAA CGG GAG GAG GAA GAA<br>Ala Glu Thr Asn Thr Ala Leu Gln Gln Pro Lys Arg Glu Glu Glu Glu<br>                    340                        345                    350 | 1326 |
| GTA TTA AAT CAG GAT GTC CAT CTA GAA GAA GAT ACA GAC TGG CCG GGA<br>Val Leu Asn Gln Asp Val His Leu Glu Glu Asp Thr Asp Trp Pro Gly<br>                        355                        360                    365 | 1374 |
| GTG AAC CTC AAA GTG GGA CAA GTG TCT GGT TTA GCG CTG GAT CCC AAG<br>Val Asn Leu Lys Val Gly Gln Val Ser Gly Leu Ala Leu Asp Pro Lys<br>          370                           375                        380 | 1422 |
| AAT AAT TTG GTT ATT TTC CAC AGG GGG GAT CAT GTC TGG GAT GAA AAC<br>Asn Asn Leu Val Ile Phe His Arg Gly Asp His Val Trp Asp Glu Asn<br>385                           390                       395 | 1470 |
| TCA TTT GAT AGG AAT TTT GTT TAT CAA CAA AGA GGA ATC GGA CCA ATC<br>Ser Phe Asp Arg Asn Phe Val Tyr Gln Gln Arg Gly Ile Gly Pro Ile<br>400                         405                     410                    415 | 1518 |
| CAG GAA AGC ACC ATT CTC GTT GTT GAT CCG AAC ACT TCT AAA GTC CTC<br>Gln Glu Ser Thr Ile Leu Val Val Asp Pro Asn Thr Ser Lys Val Leu<br>                    420                        425                    430 | 1566 |
| AAG TCA ACA GGG CAG AAT TTG TTT TTT TTG CCC CAT GGC CTG ACT ATA<br>Lys Ser Thr Gly Gln Asn Leu Phe Phe Leu Pro His Gly Leu Thr Ile<br>                    435                        440                    445 | 1614 |
| GAC AGA GAT GGG AAT TAT TGG GTC ACA GAT GTA GCC CTT CAT CAG GTT<br>Asp Arg Asp Gly Asn Tyr Trp Val Thr Asp Val Ala Leu His Gln Val<br>                    450                        455                    460 | 1662 |
| TTC AAA GTG GGA GCT GAA AAA GAA ACG CCG CTG CTT GTA TTA GGG AGG<br>Phe Lys Val Gly Ala Glu Lys Glu Thr Pro Leu Leu Val Leu Gly Arg<br>465                         470                        475 | 1710 |
| GCA TTT CAG CCT GGG AGC GAT CGG AAG CAT TTC TGT CAG CCA ACT GAT<br>Ala Phe Gln Pro Gly Ser Asp Arg Lys His Phe Cys Gln Pro Thr Asp<br>480                         485                     490                    495 | 1758 |
| GTT GCA GTC GAC CCC ATT ACT GGC AAC TTC TTT GTG GCG GAT GGC TAC<br>Val Ala Val Asp Pro Ile Thr Gly Asn Phe Phe Val Ala Asp Gly Tyr<br>                    500                        505                    510 | 1806 |

```
TGC AAC AGT CGC ATC ATG CAA TTC TCA CCT AAT GGA ATG TTC ATC ATG      1854
Cys Asn Ser Arg Ile Met Gln Phe Ser Pro Asn Gly Met Phe Ile Met
            515                 520                 525

CAG TGG GGA GAA GAA ACA TCC TCA AAC CTC CCC CGA CCT GGT CAG TTC      1902
Gln Trp Gly Glu Glu Thr Ser Ser Asn Leu Pro Arg Pro Gly Gln Phe
            530                 535                 540

CGC ATT CCA CAC AGT CTG ACC ATG ATA TCT GAC CAA GGA CAG CTG TGT      1950
Arg Ile Pro His Ser Leu Thr Met Ile Ser Asp Gln Gly Gln Leu Cys
            545                 550                 555

GTG GCC GAC AGA GAG AAC GGC CGG ATT CAG TGC TTC CAT GCT AAA ACG      1998
Val Ala Asp Arg Glu Asn Gly Arg Ile Gln Cys Phe His Ala Lys Thr
560                 565                 570                 575

GGG GAA TTT GTA AAG CAA ATC AAA CAT CAG GAA TTT GGA AGA GAG GTG      2046
Gly Glu Phe Val Lys Gln Ile Lys His Gln Glu Phe Gly Arg Glu Val
                580                 585                 590

TTT GCT GTC TCA TAT GCA CCA GGT GGA GTG TTG TAC GCT GTT AAT GGA      2094
Phe Ala Val Ser Tyr Ala Pro Gly Gly Val Leu Tyr Ala Val Asn Gly
                595                 600                 605

AAG CCG TAC TAT GGA GAT TCC ACC CCT GTA CAA GGC TTT ATG CTG AAT      2142
Lys Pro Tyr Tyr Gly Asp Ser Thr Pro Val Gln Gly Phe Met Leu Asn
            610                 615                 620

TTC TCC AAT GGG GAT ATT CTA GAT ACA TTC ATT CCT GCT AGA AAG AAT      2190
Phe Ser Asn Gly Asp Ile Leu Asp Thr Phe Ile Pro Ala Arg Lys Asn
            625                 630                 635

TTT GAA ATG CCC CAT GAT ATT GCT GCA GGA GAT GAT GGA ACG GTG TAT      2238
Phe Glu Met Pro His Asp Ile Ala Ala Gly Asp Asp Gly Thr Val Tyr
640                 645                 650                 655

GTT GGG GAT GCA CAT GCC AAC GCT GTA TGG AAG TTC TCC CCT TCA AAG      2286
Val Gly Asp Ala His Ala Asn Ala Val Trp Lys Phe Ser Pro Ser Lys
                660                 665                 670

GCA GAG CAT CGA TCT GTC AAA AAA GCT GGA ATA GAG GTA GAA GAA ATA      2334
Ala Glu His Arg Ser Val Lys Lys Ala Gly Ile Glu Val Glu Glu Ile
            675                 680                 685

ACA GAA ACC GAG ATC TTC GAG ACC CAT ATG AGA AGC AGA CCA AAG ACC      2382
Thr Glu Thr Glu Ile Phe Glu Thr His Met Arg Ser Arg Pro Lys Thr
            690                 695                 700

AAT GAA AGT GTT GGG CAG CAA ACA CAG GAG AAA CCG AGT GTT GTA CAA      2430
Asn Glu Ser Val Gly Gln Gln Thr Gln Glu Lys Pro Ser Val Val Gln
705                 710                 715

GAA AGC AGC GCC GGC GTC TCT TTC GTT CTC ATC ATC ACT CTT CTA ATC      2478
Glu Ser Ser Ala Gly Val Ser Phe Val Leu Ile Ile Thr Leu Leu Ile
720                 725                 730                 735

ATT CCT GTT GTG GTT CTC ATC GCT ATT GCA ATC TTC ATT CGT TGG AGG      2526
Ile Pro Val Val Val Leu Ile Ala Ile Ala Ile Phe Ile Arg Trp Arg
                740                 745                 750

AAA GTT AGG ATG TAT GGA GGT GAC ATT GGC CAC AAA TCA GAA TCC AGT      2574
Lys Val Arg Met Tyr Gly Gly Asp Ile Gly His Lys Ser Glu Ser Ser
            755                 760                 765

TCA GGG GGC ATC TTG GGA AAA CTT CGA GGG AAG GGC AGT GGA GGC CTT      2622
Ser Gly Gly Ile Leu Gly Lys Leu Arg Gly Lys Gly Ser Gly Gly Leu
            770                 775                 780

AAT CTG GGA ACA TTC TTT GCA ACG CAT AAA GGA TAT AGT AGA AAA GGC      2670
Asn Leu Gly Thr Phe Phe Ala Thr His Lys Gly Tyr Ser Arg Lys Gly
785                 790                 795

TTT GAC AGG CTG AGT ACA GAA GGA AGC GAC CAA GAG AAA GAT GAT GAT      2718
Phe Asp Arg Leu Ser Thr Glu Gly Ser Asp Gln Glu Lys Asp Asp Asp
800                 805                 810                 815

GAT GAT GGC TCA GAC TCT GAA GAA GAG TAT TCT GCC CCG CCT ATT CCA      2766
Asp Asp Gly Ser Asp Ser Glu Glu Glu Tyr Ser Ala Pro Pro Ile Pro
```

```
                   820              825               830
CCA GTA TCT TCC TCC TGA AACAGTTGAC TTCTTCCGTA CAACCTTTTG        2814
Pro Val Ser Ser Ser *
              835

CTCCATTAGC ACGTTTAAAA TGGTGTATTT AAATGTTACT GTACTAGTCT GTGGACTGTA   2874

CAATCGTCAT AGCTTTTATT TTTATTTGAA GTGCTGTTGT AGCCTTTATA TGAACATTCA   2934

GAATAATTCT ATTTGGTCAA TGACTTTGGC TTTTCCAGTG TTTGATGGCC TTCCTCTGCT   2994

TCACCAAGAG CACTTTAACT GCCAATTATT TTCAAGCCTT TAACTGAAAT CGAATCGCAT   3054

TACAACGATA CGTGCCACAT AAATGCAAAG CTGCTAAATC TCTTCTATTT TTTTAAATTA   3114

ACAACACGAT GTCGCGCTCA AGAAAGGAAA CGATAAAGAC ATAATATTTA ATGTTTCTTA   3174

TTTCTTTCTA TTTTTTTTTC ATTGTTTTTG GTGTTCTTGG GGTGTCTTCT TTTCAGATGG   3234

TTCCGCGGTT TAGAACACTA TTTTCAGGAA CTGAATGTAC TTTGTGTAAT AAAGTGTTCG   3294

CAGCCCCCCC CCCCCCTGCA G                                           3315
```

(2) INFORMATION FOR SEQ ID NO:63:

(i) SEQUENCE CHARACTERISTICS:
        (A) LENGTH: 400 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:63:

```
Met Ala Ser Leu Ser Ser Phe Leu Val Leu Phe Leu Phe Gln
1               5                   10                  15

Asn Ser Cys Tyr Cys Phe Arg Ser Pro Leu Ser Val Phe Lys Arg Tyr
                20                  25                  30

Glu Glu Ser Thr Arg Ser Leu Ser Asn Asp Cys Leu Gly Thr Thr Arg
            35                  40                  45

Pro Val Met Ser Pro Gly Ser Ser Asp Tyr Thr Leu Asp Ile Arg Met
    50                  55                  60

Pro Gly Val Thr Pro Thr Glu Ser Asp Thr Tyr Leu Cys Lys Ser Tyr
65                  70                  75                  80

Arg Leu Pro Val Asp Asp Glu Ala Tyr Val Val Asp Phe Arg Pro His
                85                  90                  95

Ala Asn Met Asp Thr Ala His His Met Leu Leu Phe Gly Cys Asn Ile
            100                 105                 110

Pro Ser Ser Thr Asp Asp Tyr Trp Asp Cys Ser Ala Gly Thr Cys Met
        115                 120                 125

Asp Lys Ser Ser Ile Met Tyr Ala Trp Ala Lys Asn Ala Pro Pro Thr
    130                 135                 140

Lys Leu Pro Glu Gly Val Gly Phe Arg Val Gly Lys Ser Gly Ser
145                 150                 155                 160

Arg Tyr Phe Val Leu Gln Val His Tyr Gly Asn Val Lys Ala Phe Gln
                165                 170                 175

Asp Lys His Lys Asp Cys Thr Gly Val Thr Val Arg Val Thr Pro Glu
            180                 185                 190

Lys Gln Pro Gln Ile Ala Gly Ile Tyr Leu Ser Met Ser Val Asp Thr
        195                 200                 205

Val Ile Pro Pro Gly Glu Glu Ala Val Asn Ser Asp Ile Ala Cys Leu
    210                 215                 220
```

-continued

```
Tyr Asn Arg Pro Thr Ile His Pro Phe Ala Tyr Arg Val His Thr His
225                 230                 235                 240

Gln Leu Gly Gln Val Val Ser Gly Phe Arg Val Arg His Gly Lys Trp
            245                 250                 255

Ser Leu Ile Gly Arg Gln Ser Pro Gln Leu Pro Gln Ala Phe Tyr Pro
            260                 265                 270

Val Glu His Pro Val Glu Ile Ser Pro Gly Asp Ile Ile Ala Thr Arg
            275                 280                 285

Cys Leu Phe Thr Gly Lys Gly Arg Thr Ser Ala Thr Tyr Ile Gly Gly
            290                 295                 300

Thr Ser Asn Asp Glu Met Cys Asn Leu Tyr Ile Met Tyr Met Asp
305                 310                 315                 320

Ala Ala His Ala Thr Ser Tyr Met Thr Cys Val Gln Thr Gly Glu Pro
            325                 330                 335

Lys Leu Phe Gln Asn Ile Pro Glu Ile Ala Asn Val Pro Ile Pro Val
            340                 345                 350

Ser Pro Asp Met Met Met Met Met Gly His Gly His His His Thr Glu
            355                 360                 365

Ala Glu Pro Glu Lys Asn Thr Gly Leu Gln Gln Pro Lys Arg Glu Glu
            370                 375                 380

Glu Glu Val Leu Asp Gln Gly Leu Ile Thr Leu Gly Asp Ser Ala Val
385                 390                 395                 400
```

(2) INFORMATION FOR SEQ ID NO:64:

(i) SEQUENCE CHARACTERISTICS:
        (A) LENGTH: 405 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:64:

```
Asn Met Asp Met Ala Ser Leu Ile Ser Ser Leu Leu Val Leu Phe Leu
1               5                   10                  15

Ile Phe Gln Asn Ser Cys Tyr Cys Phe Arg Ser Pro Leu Ser Val Phe
            20                  25                  30

Lys Arg Tyr Glu Glu Ser Thr Arg Ser Leu Ser Asn Asp Cys Leu Gly
            35                  40                  45

Thr Thr Arg Pro Val Met Ser Pro Gly Ser Ser Asp Tyr Thr Leu Asp
50                  55                  60

Ile Arg Met Pro Gly Val Thr Pro Thr Glu Ser Asp Thr Tyr Leu Cys
65                  70                  75                  80

Lys Ser Tyr Arg Leu Pro Val Asp Asp Glu Ala Tyr Val Val Asp Tyr
            85                  90                  95

Arg Pro His Ala Asn Met Asp Thr Ala His His Met Leu Leu Phe Gly
            100                 105                 110

Cys Asn Val Pro Ser Ser Thr Asp Asp Tyr Trp Asp Cys Ser Ala Gly
            115                 120                 125

Thr Cys Asn Asp Lys Ser Ser Ile Met Tyr Ala Trp Ala Lys Asn Ala
130                 135                 140

Pro Pro Thr Lys Leu Pro Glu Gly Val Gly Phe Gln Val Gly Gly Lys
145                 150                 155                 160

Ser Gly Ser Arg Tyr Phe Val Leu Gln Val His Tyr Gly Asp Val Lys
            165                 170                 175
```

```
Ala Phe Gln Asp Lys His Lys Asp Cys Thr Gly Val Thr Val Arg Ile
            180                 185                 190

Thr Pro Glu Lys Gln Pro Leu Ile Ala Gly Ile Tyr Leu Ser Met Ser
            195                 200                 205

Leu Asn Thr Val Val Pro Pro Gly Gln Glu Val Val Asn Ser Asp Ile
            210                 215                 220

Ala Cys Leu Tyr Asn Arg Pro Thr Ile His Pro Phe Ala Tyr Arg Val
225                 230                 235                 240

His Thr His Gln Leu Gly Gln Val Val Ser Gly Phe Arg Val Arg His
                245                 250                 255

Gly Lys Trp Thr Leu Ile Gly Arg Gln Ser Pro Gln Leu Pro Gln Ala
            260                 265                 270

Phe Tyr Pro Val Glu His Pro Leu Glu Ile Ser Pro Gly Asp Ile Ile
            275                 280                 285

Ala Thr Arg Cys Leu Phe Thr Gly Lys Gly Arg Met Ser Ala Thr Tyr
            290                 295                 300

Ile Gly Gly Thr Ala Lys Asp Glu Met Cys Asn Leu Tyr Ile Met Tyr
305                 310                 315                 320

Tyr Met Asp Ala Ala His Ala Thr Ser Tyr Met Thr Cys Val Gln Thr
                325                 330                 335

Gly Asn Pro Lys Leu Phe Glu Asn Ile Pro Glu Ile Ala Asn Val Pro
            340                 345                 350

Ile Pro Val Ser Pro Asp Met Met Met Met Met Met Gly His Gly
            355                 360                 365

His His His Thr Glu Ala Glu Ala Glu Thr Asn Thr Ala Leu Gln Gln
            370                 375                 380

Pro Lys Arg Glu Glu Glu Val Leu Asn Gln Asp Val His Leu Glu
385                 390                 395                 400

Glu Asp Thr Asp Trp
                405

(2) INFORMATION FOR SEQ ID NO:65:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..12

(xi) SEQUENCE DESCRIPTION: SEQ ID NO:65:

ATG GGG ATC CTC                                                    12
Met Gly Ile Leu
        840

(2) INFORMATION FOR SEQ ID NO:66:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
```

(B) LOCATION: 1..21

(xi) SEQUENCE DESCRIPTION: SEQ ID NO:66:

CTG CAG GCA TGC TTA ATT AAT                                              21
Leu Gln Ala Cys Leu Ile Asn
 5                       10

(2) INFORMATION FOR SEQ ID NO:67:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..33

(xi) SEQUENCE DESCRIPTION: SEQ ID NO:67:

GGG GAT CCT CTA GAG TCG ACC TGC AGG CAT GCT                              33
Gly Asp Pro Leu Glu Ser Thr Cys Arg His Ala
         10                  15

(2) INFORMATION FOR SEQ ID NO:68:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..33

(xi) SEQUENCE DESCRIPTION: SEQ ID NO:68:

GGG GAT CCT CTA GAG TCG ACC TGC AGG CAT GCT                              33
Gly Asp Pro Leu Glu Ser Thr Cys Arg His Ala
 1           5                   10

(2) INFORMATION FOR SEQ ID NO:69:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:69:

GTCATTGGAA AGTGACATGA ATTCTTCCTC ATACCTCTT                                39

(2) INFORMATION FOR SEQ ID NO:70:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:70:

CTTAATTAAT TAAGCA                                                        16

(2) INFORMATION FOR SEQ ID NO:71:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:71:

GTACGAATTA ATTAATTCGT TCGA                                            24

(2) INFORMATION FOR SEQ ID NO:72:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Protein
        (B) LOCATION: 1
        (D) OTHER INFORMATION: /note= "Amino acid at position 7 is
            Xaa wherein Xaa = Ala or Pro."

(ix) FEATURE:
        (A) NAME/KEY: Protein
        (B) LOCATION: 3
        (D) OTHER INFORMATION: /note= "Amino acid 9 is Xaa wherein
            Xaa = Thr or Lys."

(ix) FEATURE:
        (A) NAME/KEY: Protein
        (B) LOCATION: 6
        (D) OTHER INFORMATION: /note= "Amino acid 12 is Xaa
            wherein Xaa = Ala or Gly."

(xi) SEQUENCE DESCRIPTION: SEQ ID NO:72:

His His Thr Glu Ala Glu Xaa Glu Xaa Asn Thr Xaa Leu Gln Gln Pro
1             5                     10                   15

Lys (2) INFORMATION FOR SEQ ID NO:73:

(i) SEQUENCE CHARACTERISTICS:
        (A) LENGTH: 490 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:73:

Arg Glu Glu Glu Val Leu Asn Gln Asp Val His Leu Glu Glu Asp
1             5                    10                 15

Thr Asp Trp Pro Gly Val Asn Leu Lys Val Gly Gln Val Ser Gly Leu
            20                    25                   30

Ala Leu Asp Pro Lys Asn Asn Leu Val Ile Phe His Arg Gly Asp His
            35                    40                   45

Val Trp Asp Glu Asn Ser Phe Asp Arg Asn Phe Val Tyr Gln Gln Arg
            50                    55                   60

Gly Ile Gly Pro Ile Gln Glu Ser Thr Ile Leu Val Val Asp Pro Asn
65                  70                    75                   80

```
Thr Ser Lys Val Leu Lys Ser Thr Gly Gln Asn Leu Phe Phe Leu Pro
                85                  90                  95
His Gly Leu Thr Ile Asp Arg Asp Gly Asn Tyr Trp Val Thr Asp Val
            100                 105                 110
Ala Leu His Gln Val Phe Lys Val Gly Ala Glu Lys Glu Thr Pro Leu
        115                 120                 125
Leu Val Leu Gly Arg Ala Phe Gln Pro Gly Ser Asp Arg Lys His Phe
    130                 135                 140
Cys Gln Pro Thr Asp Val Ala Val Asp Pro Ile Thr Gly Asn Phe Phe
145                 150                 155                 160
Val Ala Asp Gly Tyr Cys Asn Ser Arg Ile Met Gln Phe Ser Pro Asn
                165                 170                 175
Gly Met Phe Ile Met Gln Trp Gly Glu Glu Thr Ser Ser Asn Leu Pro
            180                 185                 190
Arg Pro Gly Gln Phe Arg Ile Pro His Ser Leu Thr Met Ile Ser Asp
        195                 200                 205
Gln Gly Gln Leu Cys Val Ala Asp Arg Glu Asn Gly Arg Ile Gln Cys
    210                 215                 220
Phe His Ala Lys Thr Gly Glu Phe Val Lys Gln Ile Lys His Gln Glu
225                 230                 235                 240
Phe Gly Arg Glu Val Phe Ala Val Ser Tyr Ala Pro Gly Gly Val Leu
                245                 250                 255
Tyr Ala Val Asn Gly Lys Pro Tyr Tyr Gly Asp Ser Thr Pro Val Gln
            260                 265                 270
Gly Phe Met Leu Asn Phe Ser Asn Gly Asp Ile Leu Asp Thr Phe Ile
        275                 280                 285
Pro Ala Arg Lys Asn Phe Glu Met Pro His Asp Ile Ala Ala Gly Asp
    290                 295                 300
Asp Gly Thr Val Tyr Val Gly Asp Ala His Ala Asn Ala Val Trp Lys
305                 310                 315                 320
Phe Ser Pro Ser Lys Ala Glu His Arg Ser Val Lys Lys Ala Gly Ile
                325                 330                 335
Glu Val Glu Glu Ile Thr Glu Thr Glu Ile Phe Glu Thr His Met Arg
            340                 345                 350
Ser Arg Pro Lys Thr Asn Glu Ser Val Gly Gln Gln Thr Gln Glu Lys
        355                 360                 365
Pro Ser Val Val Gln Glu Ser Ser Ala Gly Val Ser Phe Val Leu Ile
    370                 375                 380
Ile Thr Leu Leu Ile Ile Pro Val Val Leu Ile Ala Ile Ala Ile
385                 390                 395                 400
Phe Ile Arg Trp Arg Lys Val Arg Met Tyr Gly Gly Asp Ile Gly His
                405                 410                 415
Lys Ser Glu Ser Ser Gly Gly Ile Leu Gly Lys Leu Arg Gly Lys
            420                 425                 430
Gly Ser Gly Gly Leu Asn Leu Gly Thr Phe Phe Ala Thr His Lys Gly
        435                 440                 445
Tyr Ser Arg Lys Gly Phe Asp Arg Leu Ser Thr Glu Gly Ser Asp Gln
    450                 455                 460
Glu Lys Asp Asp Asp Asp Gly Ser Asp Glu Glu Tyr Ser
465                 470                 475                 480
Ala Pro Pro Ile Pro Pro Val Ser Ser
                485                 490
```

(2) INFORMATION FOR SEQ ID NO:74:

(i) SEQUENCE CHARACTERISTICS:
        (A) LENGTH: 347 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:74:

```
Arg Glu Glu Glu Val Leu Asn Gln Asp Val His Leu Glu Asp
  1               5                  10                  15

Thr Asp Trp Pro Gly Val Asn Leu Lys Val Gly Gln Val Ser Gly Leu
             20                  25                  30

Ala Leu Asp Pro Lys Asn Asn Leu Val Ile Phe His Arg Gly Asp His
             35                  40                  45

Val Trp Asp Glu Asn Ser Phe Asp Arg Asn Phe Val Tyr Gln Gln Arg
 50                  55                  60

Gly Ile Gly Pro Ile Gln Glu Ser Thr Ile Leu Val Val Asp Pro Asn
 65                  70                  75                  80

Thr Ser Lys Val Leu Lys Ser Thr Gly Gln Asn Leu Phe Phe Leu Pro
             85                  90                  95

His Gly Leu Thr Ile Asp Arg Asp Gly Asn Tyr Trp Val Thr Asp Val
            100                 105                 110

Ala Leu His Gln Val Phe Lys Val Gly Ala Glu Lys Glu Thr Pro Leu
            115                 120                 125

Leu Val Leu Gly Arg Ala Phe Gln Pro Gly Ser Asp Arg Lys His Phe
130                 135                 140

Cys Gln Pro Thr Asp Val Ala Val Asp Pro Ile Thr Gly Asn Phe Phe
145                 150                 155                 160

Val Ala Asp Gly Tyr Cys Asn Ser Arg Ile Met Gln Phe Ser Pro Asn
            165                 170                 175

Gly Met Phe Ile Met Gln Trp Gly Glu Glu Thr Ser Ser Asn Leu Pro
            180                 185                 190

Arg Pro Gly Gln Phe Arg Ile Pro His Ser Leu Thr Met Ile Ser Asp
            195                 200                 205

Gln Gly Gln Leu Cys Val Ala Asp Arg Glu Asn Gly Arg Ile Gln Cys
210                 215                 220

Phe His Ala Lys Thr Gly Glu Phe Val Lys Gln Ile Lys His Gln Glu
225                 230                 235                 240

Phe Gly Arg Glu Val Phe Ala Val Ser Tyr Ala Pro Gly Gly Val Leu
            245                 250                 255

Tyr Ala Val Asn Gly Lys Pro Tyr Tyr Gly Asp Ser Thr Pro Val Gln
            260                 265                 270

Gly Phe Met Leu Asn Phe Ser Asn Gly Asp Ile Leu Asp Thr Phe Ile
            275                 280                 285

Pro Ala Arg Lys Asn Phe Glu Met Pro His Asp Ile Ala Ala Gly Asp
            290                 295                 300

Asp Gly Thr Val Tyr Val Gly Asp Ala His Ala Asn Ala Val Trp Lys
305                 310                 315                 320

Phe Ser Pro Ser Lys Ala Glu His Arg Ser Val Lys Lys Ala Gly Ile
            325                 330                 335

Glu Val Glu Glu Ile Thr Glu Thr Glu Ile Leu
            340                 345
```

(2) INFORMATION FOR SEQ ID NO:75:

(i) SEQUENCE CHARACTERISTICS:
        (A) LENGTH: 209 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:75:

```
Arg Glu Glu Glu Glu Val Leu Asn Gln Asp Val His Leu Glu Glu Asp
  1               5                  10                  15

Thr Asp Trp Pro Gly Val Asn Leu Lys Val Gly Gln Val Ser Gly Leu
                20                  25                  30

Ala Leu Asp Pro Lys Asn Asn Leu Val Ile Phe His Arg Gly Asp His
            35                  40                  45

Val Trp Asp Glu Asn Ser Phe Asp Arg Asn Phe Val Tyr Gln Gln Arg
 50                  55                  60

Gly Ile Gly Pro Ile Gln Glu Ser Thr Ile Leu Val Val Asp Pro Asn
 65                  70                  75                  80

Thr Ser Lys Val Leu Lys Ser Thr Gly Gln Asn Leu Phe Phe Leu Pro
                85                  90                  95

His Gly Leu Thr Ile Asp Arg Asp Gly Asn Tyr Trp Val Thr Asp Val
               100                 105                 110

Ala Leu His Gln Val Phe Lys Val Gly Ala Glu Lys Glu Thr Pro Leu
           115                 120                 125

Leu Val Leu Gly Arg Ala Phe Gln Pro Gly Ser Asp Arg Lys His Phe
130                 135                 140

Cys Gln Pro Thr Asp Val Ala Val Asp Pro Ile Thr Gly Asn Phe Phe
145                 150                 155                 160

Val Ala Asp Gly Tyr Cys Asn Ser Arg Ile Met Gln Phe Ser Pro Asn
               165                 170                 175

Gly Met Phe Ile Met Gln Trp Gly Glu Glu Thr Ser Ser Asn Leu Pro
           180                 185                 190

Arg Pro Gly Gln Phe Arg Ile Pro His Ser Leu Thr Met Met Gly Ile
       195                 200                 205

Leu
```

(2) INFORMATION FOR SEQ ID NO:76:

(i) SEQUENCE CHARACTERISTICS:
        (A) LENGTH: 160 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:76:

```
Arg Glu Glu Glu Glu Val Leu Asn Gln Asp Val His Leu Glu Glu Asp
  1               5                  10                  15

Thr Asp Trp Pro Gly Val Asn Leu Lys Val Gly Gln Val Ser Gly Leu
                20                  25                  30

Ala Leu Asp Pro Lys Asn Asn Leu Val Ile Phe His Arg Gly Asp His
            35                  40                  45

Val Trp Asp Glu Asn Ser Phe Asp Arg Asn Phe Val Tyr Gln Gln Arg
 50                  55                  60
```

```
Gly Ile Gly Pro Ile Gln Glu Ser Thr Ile Leu Val Val Asp Pro Asn
 65                  70                  75                  80

Thr Ser Lys Val Leu Lys Ser Thr Gly Gln Asn Leu Phe Phe Leu Pro
                 85                  90                  95

His Gly Leu Thr Ile Asp Arg Asp Gly Asn Tyr Trp Val Thr Asp Val
                100                 105                 110

Ala Leu His Gln Val Phe Lys Val Gly Ala Glu Lys Glu Thr Pro Leu
                115                 120                 125

Leu Val Leu Gly Arg Ala Phe Gln Pro Gly Ser Asp Arg Lys His Phe
130                 135                 140

Cys Gln Pro Thr Asp Val Ala Val Asp Leu Gln Ala Cys Leu Ile Asn
145                 150                 155                 160

(2) INFORMATION FOR SEQ ID NO:77:

(i) SEQUENCE CHARACTERISTICS:
        (A) LENGTH: 329 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

Ser Leu Ser Asn Asp Cys Leu Gly Thr Thr Arg Pro Val Met Ser Pro
  1               5                  10                  15

Gly Ser Ser Asp Tyr Thr Leu Asp Ile Arg Met Pro Gly Val Thr Pro
                 20                  25                  30

Thr Glu Ser Asp Thr Tyr Leu Cys Lys Ser Tyr Arg Leu Pro Val Asp
                 35                  40                  45

Asp Glu Ala Tyr Val Val Asp Tyr Arg Pro His Ala Asn Met Asp Thr
 50                  55                  60

Ala His His Met Leu Leu Phe Gly Cys Asn Val Pro Ser Ser Thr Asp
 65                  70                  75                  80

Asp Tyr Trp Asp Cys Ser Ala Gly Thr Cys Asn Asp Lys Ser Ser Ile
                 85                  90                  95

Met Tyr Ala Trp Ala Lys Asn Ala Pro Pro Thr Lys Leu Pro Glu Gly
                100                 105                 110

Val Gly Phe Gln Val Gly Gly Lys Ser Gly Ser Arg Tyr Phe Val Leu
                115                 120                 125

Gln Val His Tyr Gly Asp Val Lys Ala Phe Gln Asp Lys His Lys Asp
                130                 135                 140

Cys Thr Gly Val Thr Val Arg Ile Thr Pro Glu Lys Gln Pro Leu Ile
145                 150                 155                 160

Ala Gly Ile Tyr Leu Ser Met Ser Leu Asn Thr Val Val Pro Pro Gly
                165                 170                 175

Gln Glu Val Val Asn Ser Asp Ile Ala Cys Leu Tyr Asn Arg Pro Thr
                180                 185                 190

Ile His Pro Phe Ala Tyr Arg Val His Thr His Gln Leu Gly Gln Val
                195                 200                 205

Val Ser Gly Phe Arg Val Arg His Gly Lys Trp Thr Leu Ile Gly Arg
                210                 215                 220

Gln Ser Pro Gln Leu Pro Gln Ala Phe Tyr Pro Val Glu His Pro Leu
225                 230                 235                 240

Glu Ile Ser Pro Gly Asp Ile Ile Ala Thr Arg Cys Leu Phe Thr Gly
                245                 250                 255
```

```
Lys Gly Arg Met Ser Ala Thr Tyr Ile Gly Gly Thr Ala Lys Asp Glu
            260                 265                 270

Met Cys Asn Leu Tyr Ile Met Tyr Tyr Met Asp Ala Ala His Ala Thr
        275                 280                 285

Ser Tyr Met Thr Cys Val Gln Thr Gly Asn Pro Lys Leu Phe Glu Asn
    290                 295                 300

Ile Pro Glu Ile Ala Asn Val Pro Ile Pro Val Ser Pro Asp Met Met
305                 310                 315                 320

Met Met Met Met Met Gly His Gly His
                325
```

What is claimed is:

1. A process for the production of a C-terminal α-amidated peptide or protein comprising reacting a C-terminal α-amidating enzyme of *Xenopus laevis* produced by a recombinant DNA technique with a peptide or protein having a glycine residue at a C-terminal thereof, wherein said C-terminal α-amidating enzyme has the following amino acid sequence (IV):

```
                                              (SEQ ID NO:77)
A'-Ser Leu Ser Asn Asp Cys Leu Gly Thr Thr

Arg Pro Val Met Ser Pro Gly Ser Ser Asp

Tyr Thr Leu Asp Ile Arg Met Pro Gly Val

Thr Pro Thr Glu Ser Asp Thr Tyr Leu Cys

Lys Ser Tyr Arg Leu Pro Val Asp Asp Glu

Ala Tyr Val Val Asp Tyr Arg Pro His Ala

Asn Met Asp Thr Ala His His Met Leu Leu

Phe Gly Cys Asn Val Pro Ser Ser Thr Asp

Asp Tyr Trp Asp Cys Ser Ala Gly Thr Cys

Asn Asp Lys Ser Ser Ile Met Tyr Ala Trp

Ala Lys Asn Ala Pro Pro Thr Lys Leu Pro

Glu Gly Val Gly Phe Gln Val Gly Gly Lys

Ser Gly Ser Arg Tyr Phe Val Leu Gln Val

His Tyr Gly Asp Val Lys Ala Phe Gln Asp

Lys His Lys Asp Cys Thr Gly Val Thr Val

Arg Ile Thr Pro Glu Lys Gln Pro Leu Ile

Ala Gly Ile Tyr Leu Ser Met Ser Leu Asn

Thr Val Val Pro Pro Gly Gln Glu Val Val

Asn Ser Asp Ile Ala Cys Leu Tyr Asn Arg

Pro Thr Ile His Pro Phe Ala Tyr Arg Val

His Thr His Gln Leu Gly Gln Val Val Ser

Gly Phe Arg Val Arg His Gly Lys Trp Thr

Leu Ile Gly Arg Gln Ser Pro Gln Leu Pro

Gln Ala Phe Tyr Pro Val Glu His Pro Leu

Glu Ile Ser Pro Gly Asp Ile Ile Ala Thr

Arg Cys Leu Phe Thr Gly Lys Gly Arg Met

Ser Ala Thr Tyr Ile Gly Gly Thr Ala Lys

Asp Glu Met Cys Asn Leu Tyr Ile Met Tyr

Tyr Met Asp Ala Ala His Ala Thr Ser Tyr

Met Thr Cys Val Gln Thr Gly Asn Pro Lys

Leu Phe Glu Asn Ile Pro Glu Ile Ala Asn

Val Pro Ile Pro Val Ser Pro Asp Met Met

Met Met Met Met Met Gly His Gly His-C
``` wherein A' is absent or represents the following amino acid sequence (XXI):

```
Met Asp Met Ala Ser Leu Ile Ser Ser Leu

Leu Val Leu Phe Leu Ile Phe Gln Asn Ser

Cys Tyr Cys Phe Arg Ser Pro Leu Ser Val

Phe Lys Arg Tyr Glu Glu Ser Thr Arg (amino acids 2–40 of SEQ ID NO:64);
```

C represents the following amino acid sequence (V):
Gly Asp Pro Leu Glu Ser Thr Cys Arg His Ala (SEQ ID NO:17), or
the following amino acid sequence (VI):
His His Thr Glu Ala Glu-X-Glu-Y-Asn Thr-Z-Leu Gln Gln Pro Lys-D (SEQ ID NO:72)
wherein D is absent or represents the following amino acid sequence (VI), (VIII), (IX) or (X):

```
                                              (SEQ ID NO:73)
(VII):  Arg Glu Glu Glu Glu Val Leu Asn

Gln Asp Val His Leu Glu Glu Asp Thr Asp

Trp Pro Gly Val Asn Leu Lys Val Gly Gln

Val Ser Gly Leu Ala Leu Asp Pro Lys Asn

Asn Leu Val Ile Phe His Arg Gly Asp His

Val Trp Asp Glu Asn Ser Phe Asp Arg Asn
```

-continued

Phe Val Tyr Gln Gln Arg Gly Ile Gly Pro
Ile Gln Glu Ser Thr Ile Leu Val Val Asp
Pro Asn Thr Ser Lys Val Leu Lys Ser Thr
Gly Gln Asn Leu Phe Phe Leu Pro His Gly
Leu Thr Ile Asp Arg Asp Gly Asn Tyr Trp
Val Thr Asp Val Ala Leu His Gln Val Phe
Lys Val Gly Ala Glu Lys Glu Thr Pro Leu
Leu Val Leu Gly Arg Ala Phe Gln Pro Gly
Ser Asp Arg Lys His Phe Cys Gln Pro Thr
Asp Val Ala Val Asp Pro Ile Thr Gly Asn
Phe Phe Val Ala Asp Gly Tyr Cys Asn Ser
Arg Ile Met Gln Phe Ser Pro Asn Gly Met
Phe Ile Met Gln Trp Gly Glu Glu Thr Ser
Ser Asn Leu Pro Arg Pro Gly Gln Phe Arg
Ile Pro His Ser Leu Thr Met Ile Ser Asp
Gln Gly Gln Leu Cys Val Ala Asp Arg Glu
Asn Gly Arg Ile Gln Cys Phe His Ala Lys
Thr Gly Glu Phe Val Lys Gln Ile Lys His
Gln Glu Phe Gly Arg Glu Val Phe Ala Val
Ser Tyr Ala Pro Gly Gly Val Leu Tyr Ala
Val Asn Gly Lys Pro Tyr Tyr Gly Asp Ser
Thr Pro Val Gln Gly Phe Met Leu Asn Phe
Ser Asn Gly Asp Ile Leu Asp Thr Phe Ile
Pro Ala Arg Lys Asn Phe Glu Met Pro His
Asp Ile Ala Ala Gly Asp Asp Gly Thr Val
Tyr Val Gly Asp Ala His Ala Asn Ala Val
Trp Lys Phe Ser Pro Ser Lys Ala Glu His
Arg Ser Val Lys Lys Ala Gly Ile Glu Val
Glu Glu Ile Thr Glu Thr Glu Ile Phe Glu
Thr His Met Arg Ser Arg Pro Lys Thr Asn
Glu Ser Val Gly Gln Gln Thr Gln Glu Lys
Pro Ser Val Val Gln Glu Ser Ser Ala Gly
Val Ser Phe Val Leu Ile Ile Thr Leu Leu
Ile Ile Pro Val Val Leu Ile Ala Ile
Ala Ile Phe Ile Arg Trp Arg Lys Val Arg
Met Tyr Gly Gly Asp Ile Gly His Lys Ser
Glu Ser Ser Ser Gly Gly Ile Leu Gly Lys
Leu Arg Gly Lys Gly Ser Gly Gly Leu Asn
Leu Gly Thr Phe Phe Ala Thr His Lys Gly
Tyr Ser Arg Lys Gly Phe Asp Arg Leu Ser
Thr Glu Gly Ser Asp Gln Glu Lys Asp Asp

-continued

Asp Asp Asp Gly Ser Asp Ser Glu Glu Glu
Tyr Ser Ala Pro Pro Ile Pro Pro Val Ser
Ser Ser;

(SEQ ID NO:74)
(VIII): Arg Glu Glu Glu Glu Val Leu Asn
Gln Asp Val His Leu Glu Glu Asp Thr Asp
Trp Pro Gly Val Asn Leu Lys Val Gly Gln
Val Ser Gly Leu Ala Leu Asp Pro Lys Asn
Asn Leu Val Ile Phe His Arg Gly Asp His
Val Trp Asp Glu Asn Ser Phe Asp Arg Asn
Phe Val Tyr Gln Gln Arg Gly Ile Gly Pro
Ile Gln Glu Ser Thr Ile Leu Val Val Asp
Pro Asn Thr Ser Lys Val Leu Lys Ser Thr
Gly Gln Asn Leu Phe Phe Leu Pro His Gly
Leu Thr Ile Asp Arg Asp Gly Asn Tyr Trp
Val Thr Asp Val Ala Leu His Gln Val Phe
Lys Val Gly Ala Glu Lys Glu Thr Pro Leu
Leu Val Leu Gly Arg Ala Phe Gln Pro Gly
Ser Asp Arg Lys His Phe Cys Gln Pro Thr
Asp Val Ala Val Asp Pro Ile Thr Gly Asn
Phe Phe Val Ala Asp Gly Tyr Cys Asn Ser
Arg Ile Met Gln Phe Ser Pro Asn Gly Met
Phe Ile Met Gln Trp Gly Glu Glu Thr Ser
Ser Asn Leu Pro Arg Pro Gly Gln Phe Arg
Ile Pro His Ser Leu Thr Met Ile Ser Asp
Gln Gly Gln Leu Cys Val Ala Asp Arg Glu
Asn Gly Arg Ile Gln Cys Phe His Ala Lys
Thr Gly Glu Phe Val Lys Gln Ile Lys His
Gln Glu Phe Gly Arg Glu Val Phe Ala Val
Ser Tyr Ala Pro Gly Gly Val Leu Tyr Ala
Val Asn Gly Lys Pro Tyr Tyr Gly Asp Ser
Thr Pro Val Gln Gly Phe Met Leu Asn Phe
Ser Asn Gly Asp Ile Leu Asp Thr Phe Ile
Pro Ala Arg Lys Asn Phe Glu Met Pro His
Asp Ile Ala Ala Gly Asp Asp Gly Thr Val
Tyr Val Gly Asp Ala His Ala Asn Ala Val
Trp Lys Phe Ser Pro Ser Lys Ala Glu His

-continued

Arg Ser Val Lys Lys Ala Gly Ile Glu Val

Glu Glu Ile Thr Glu Thr Gru Ile Leu;

(SEQ ID NO:75)
(IX): Arg Glu Glu Glu Val Leu Asn

Gln Asp Val His Leu Glu Glu Asp Thr Asp

Trp Pro Gly Val Asn Leu Lys Val Gly Gln

Val Ser Gly Leu Ala Leu Asp Pro Lys Asn

Asn Leu Val Ile Phe His Arg Gly Asp His

Val Trp Asp Glu Asn Ser Phe Asp Arg Asn

Phe Val Tyr Gln Gln Arg Gly Ile Gly Pro

Ile Gln Glu Ser Thr Ile Leu Val Val Asp

Pro Asn Thr Ser Lys Val Leu Lys Ser Thr

Gly Gln Asn Leu Phe Phe Leu Pro His Gly

Leu Thr Ile Asp Arg Asp Gly Asn Tyr Trp

Val Thr Asp Val Ala Leu His Gln Val Phe

Lys Val Gly Ala Glu Lys Glu Thr Pro Leu

Leu Val Leu Gly Arg Ala Phe Gln Pro Gly

Ser Asp Arg Lye His Phe Cys Gln Pro Thr

Asp Val Ala Val Asp Pro Ile Thr Gly Asn

Phe Phe Val Ala Asp Gly Tyr Cys Asn Ser

Arg Ile Met Gln Phe Ser Pro Asn Gly Met

Phe Ile Met Gln Trp Gly Glu Glu Thr Ser

-continued

Ser Asn Leu Pro Arg Pro Gly Gln Phe Arg

Ile Pro His Ser Leu Thr Met Met Gly Ile

Leu;

(SEQ ID NO:76)
(X): Arg Glu Glu Glu Val Leu Asn

Gln Asp Val His Leu Glu Glu Asp Thr Asp

Trp Pro Gly Val Asn Leu Lys Val Gly Gln

Val Ser Gly Leu Ala Leu Asp Pro Lys Asn

Asn Leu Val Ile Phe His Arg Gly Asp His

Val Trp Asp Glu Asn Ser Phe Asp Arg Asn

Phe Val Tyr Gln Gln Arg Gly Ile Gly Pro

Ile Gln Glu Ser Thr Ile Leu Val Val Asp

Pro Asn Thr Ser Lys Val Leu Lys Ser Thr

Gly Gln Asn Leu Phe Phe Leu Pro His Gly

Leu Thr Ile Asp Arg Asp Gly Asn Tyr Trp

Val Thr Asp Val Ala Leu His Gln Val Phe

Lys Val Gly Ala Glu Lys Glu Thr Pro Leu

Leu Val Leu Gly Arg Ala Phe Gln Pro Gly

Ser Asp Arg Lys His Phe Cys Gln Pro Thr

Asp Val Ala Val Asp Leu Gln Ala Cys Leu

Ile Asn;

X represents Ala or Pro; Y represents Thr or Lys; and Z represents Ala or Gly; with the proviso that if A' and D are absent, the case wherein X is Ala, Y is Thr, and Z is Ala is excluded.

\* \* \* \* \*